United States Patent
Routier et al.

(10) Patent No.: US 10,202,372 B2
(45) Date of Patent: Feb. 12, 2019

(54) TRISUBSTITUTED PYRIDO[2,3-D]PYRIMIDINES, METHODS FOR PREPARING SAME AND THERAPEUTIC USES THEREOF

(71) Applicants: CENTRE NATIONAL DE LA RECHERCHE SCIENTIFIQUE (C.N.R.S), Paris (FR); UNIVERSITE D'ORLEANS, Orleans (FR)

(72) Inventors: Sylvain Routier, Tigy (FR); Hélène Benedetti, Saint-Jean-de-Bray (FR); Frédéric Buron, Olivet (FR); Marie-Aude Hiebel, Olivet (FR); Thibault Saurat, Orleans (FR); Gérald Guillaumet, Saint-Jean-le-Blanc (FR)

(73) Assignees: CENTRE NATIONAL DE LA RECHERCHE SCIENTIFIQUE (C.N.R.S), Paris (FR); UNIVERSITE D'ORLEANS, Orleans (FR)

( * ) Notice: Subject to any disclaimer, the term of this patent is extended or adjusted under 35 U.S.C. 154(b) by 0 days.

(21) Appl. No.: 14/421,402

(22) PCT Filed: Aug. 16, 2013

(86) PCT No.: PCT/EP2013/067129
§ 371 (c)(1),
(2) Date: Feb. 12, 2015

(87) PCT Pub. No.: WO2014/027081
PCT Pub. Date: Feb. 20, 2014

(65) Prior Publication Data
US 2015/0203489 A1    Jul. 23, 2015

(30) Foreign Application Priority Data
Aug. 17, 2012 (FR) .................... 12 57856

(51) Int. Cl.
*C07D 471/04* (2006.01)
*C07D 413/14* (2006.01)

(52) U.S. Cl.
CPC ......... *C07D 471/04* (2013.01); *C07D 413/14* (2013.01)

(58) Field of Classification Search
CPC ................ C07D 413/14; C07D 471/04
See application file for complete search history.

(56) References Cited

FOREIGN PATENT DOCUMENTS

| WO | WO 2006/135993 A1 | 12/2006 |
| WO | WO 2008/024977 A2 | 2/2008 |
| WO | WO 2011/101429 A1 | 8/2011 |
| WO | WO 2011/135259 A1 | 11/2011 |
| WO | WO 2012/058671 A1 | 5/2012 |

OTHER PUBLICATIONS

Li et al., J. Mol. Model (2010) 16: 1449-1460.*
De Carcer, G. et al. 2007 "Targeting cell cycle kinases for cancer therapy" Current Medicinal Chemistry 14: 969-985.

* cited by examiner

*Primary Examiner* — Rebecca L Anderson
(74) *Attorney, Agent, or Firm* — Knobbe, Martens, Olson & Bear, LLP

(57) ABSTRACT

The present invention relates to compounds of the following general formula (I):

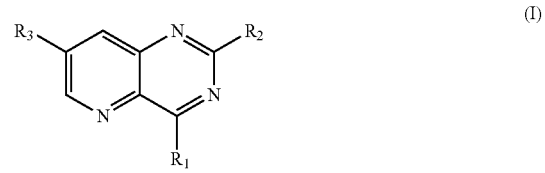

wherein:
$R_1$ is notably a group —$NR_aR_b$, $R_a$ and $R_b$ forming together with the nitrogen atom onto which they are bound, a heterocycle comprising from 5 to 30 atoms,
$R_2$ is notably an aryl comprising from 5 to 30 atoms, and
$R_3$ is notably an alkenyl comprising from 1 to 20 carbon atoms.

8 Claims, No Drawings

TRISUBSTITUTED PYRIDO[2,3-D]PYRIMIDINES, METHODS FOR PREPARING SAME AND THERAPEUTIC USES THEREOF

FIELD OF THE INVENTION

The present invention relates to novel derivatives of the pyrido[3,2-d]pyrimidine type and to their preparation methods. It also relates to the therapeutic uses of said novel derivatives notably as inhibitors of kinases.

BACKGROUND OF THE INVENTION

Inhibition of the enzymes making up cell signalling cascades have been the subject of intense efforts. Among them, one of the most universally over regulated ones is the PI3K-Akt-mTor cascade.

The "mammalian target of rapamycin" (mTOR) is a member of the family of PIKK kinases. It appears as a non-conventional family of serine/threonine kinase with a high molecular weight, the sequences of which are similar to that of PI3K. In cancer, mTOR is frequently over activated thus validating this enzyme as a therapeutic target. Two alkaloids of natural origin are presently used as a clinical drug. These are temsirolimus and everolimus.

The "phosphatidyl-inositol 3-kinase" (PI3K), as for it, is an ubiquitous enzyme which phosphorylates the hydroxyl group located in position 3 of phosphatidyl-inositol 4,5 biphosphate (PIP2). This reaction, which generates phosphatidyl-inositol 3,4,5 triphosphate (PIP3), will subsequently trigger a cascade of reactions which will favour apoptosis, cell proliferation, angiogenesis or progression of the cell cycle. PI3K is a heterodimer consisting of a catalytic sub-unit p110 and of a regulatory sub-unit p85. There are four types of isoforms α, β, γ and δ for the sub-unit p110. However, each isoform of the catalytic sub-unit will have a more or less predominant role depending on certain types of pathologies. PI3K α will be involved in many cancers, while PI3K β seems to be only involved in specific cancers and also in thrombosis phenomena. The isoforms PI3K γ and PI3K δ are involved in immune responses i.e. inflammatory mechanisms and auto-immune diseases.

SUMMARY OF THE INVENTION

Simultaneously inhibiting both of these two enzymes may give rise to efficient treatments against cancer.

The object of the present invention is to provide novel PI3K inhibitors.

The object of the present invention is to provide novel inhibitors of mTOR.

The object of the present invention is to provide simultaneous novel inhibitors of PI3K and mTOR.

The object of the present invention is to provide novel inhibitors of PI3K and mTOR kinases directly and selectively targeting said kinases.

The present invention relates to compounds of the following general formula (I):

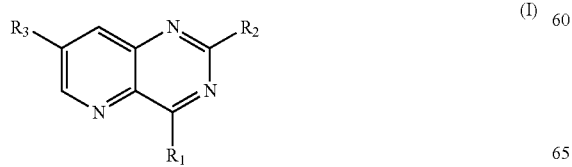

wherein:
R$_1$ is selected from the group consisting of:
(hetero)aryls comprising from 5 to 30 atoms, optionally substituted, and
groups —NR$_a$R$_b$, R$_a$ and R$_b$ forming together with the nitrogen atom to which they are bound, a heterocycle comprising from 5 to 30 atoms, optionally comprising a —SO$_2$— radical or another heteroatom selected from N, O and S, said heterocycle being optionally substituted;
R$_2$ is selected from the group consisting of:
halogen atoms,
(hetero)aryls comprising from 5 to 30 atoms, optionally substituted,
groups —NR'$_a$R'$_b$, R'$_a$ and R'$_b$ forming together with the nitrogen atom to which they are bound, a heterocycle comprising from 5 to 30 atoms, optionally comprising an —SO$_2$— radical or another heteroatom selected from N, O and S, said heterocycle being optionally substituted; and
R$_3$ is selected from the group consisting of:
halogen atoms;
alkenyls comprising from 1 to 20 carbon atoms optionally substituted,
groups —C(O)R$_c$, R$_c$ being selected from the group consisting of a hydrogen atom or of an alkyl group comprising from 1 to 10 carbon atoms, said alkyl group being optionally substituted,
groups —C(O)OR'$_c$, R'$_c$ being selected from the group consisting of a hydrogen atom or of an alkyl group comprising from 1 to 10 carbon atoms, said alkyl group being optionally substituted,
groups —C(R$_e$)=N—(OR$_d$), R$_d$ and R$_e$ being independently selected from the group consisting of a hydrogen atom and of an alkyl group comprising from 1 to 10 carbon atoms,
heterocycloalkyls comprising from 3 to 20 atoms, optionally substituted,
alkyls, comprising from 1 to 20 carbon atoms, optionally substituted with at least one substituent;
provided that at least one of R$_1$ and R$_2$ represents a group —NR$_a$R$_b$ or a group —NR'$_a$R'$_b$, respectively,
as well as its pharmaceutically acceptable salts, notably hydrochlorides, its hydrates or its polymorphic crystalline structures, its racemates, diastereoisomers or enantiomers.

The present invention relates to compounds of the following general formula (I):

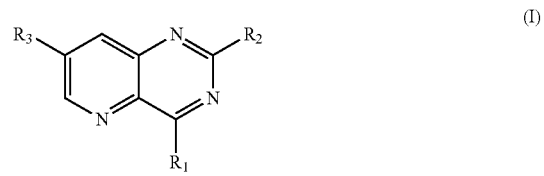

wherein:
R$_1$ is selected from the group consisting of:
(hetero)aryls comprising from 5 to 30 atoms, optionally substituted, and
groups —NR$_a$R$_b$, R$_a$ and R$_b$ forming together with the nitrogen atom to which they are bound, a heterocycle comprising from 5 to 30 atoms, optionally comprising a —SO$_2$— radical or another heteroatom selected from N, O and S, said heterocycle being optionally substituted;

$R_2$ is selected from the group consisting of:
halogen atoms selected from F, Br and I,
aryls comprising from 5 to 30 atoms, optionally substituted,
groups —NR'$_a$R'$_b$, R'$_a$ and R'$_b$ forming together with the nitrogen atom to which they are bound, a heterocycle comprising from 5 to 30 atoms, optionally comprising a —SO$_2$— radical or another heteroatom selected from N, O and S, said heterocycle being optionally substituted; and $R_3$ is selected from the group consisting of:
halogen atoms selected from F, Cl and I,
alkenyls comprising from 1 to 20 carbon atoms, optionally substituted,
groups —C(O)R$_c$, R$_c$ being selected from the group consisting of a hydrogen atom and of an alkyl group comprising from 1 to 10 carbon atoms, said alkyl group being optionally substituted,
groups —C(O)OR'$_c$, R'$_c$ being selected from the group consisting of a hydrogen atom and of an alkyl group comprising from 1 to 10 carbon atoms, said alkyl group being optionally substituted,
groups —C(R$_e$)=N—(OR$_d$), R$_d$ and R$_e$ being independently selected from the group consisting of a hydrogen atom and of an alkyl group comprising from 1 to 10 carbon atoms,
heterocycloalkyls comprising from 3 to 20 atoms, optionally substituted,
alkyls, comprising from 1 to 20 carbon atoms, optionally substituted with at least one substituent;
provided that at least one of $R_1$ and $R_2$ represents a group —NR$_a$R$_b$ or a group —NR'$_a$R'$_b$, respectively,
as well as its pharmaceutically acceptable salts, notably hydrochlorides, its hydrates or its polymorphic crystalline structures, its racemates, diastereoisomers or enantiomers.

In particular, the compounds of formula (I) of the invention are used in free form or in a salified form, notably hydrochlorides.

According to an embodiment, the present invention relates to compounds with the following general formula (I):

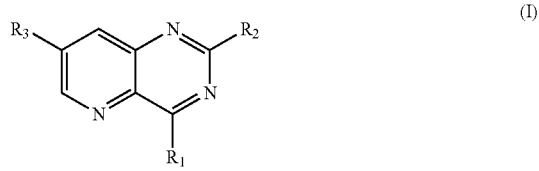

wherein:
$R_1$ is selected from the group consisting of:
(hetero)aryls comprising from 5 to 30 atoms, optionally substituted, and
groups —NR$_a$R$_b$, R$_a$ and R$_b$ forming together with the nitrogen atom to which they are bound, a heterocycle comprising from 5 to 30 atoms, optionally comprising a —SO$_2$— radical or another heteroatom selected from N, O and S, said heterocycle being optionally substituted;

$R_2$ is selected from the group consisting of:
aryls comprising from 5 to 30 carbon atoms, optionally substituted,
groups —NR'$_a$R'$_b$, R'$_a$ and R'$_b$ forming together with the nitrogen atom to which they are bound, a heterocycle comprising from 5 to 30 atoms, optionally comprising a —SO$_2$— radical or another heteroatom selected from N, O and S, said heterocycle being optionally substituted; and $R_3$ is selected from the group consisting of:
alkenyls comprising from 1 to 20 carbon atoms, optionally substituted,
groups —C(O)R$_c$, R$_c$ being selected from the group consisting of a hydrogen atom or an alkyl group comprising from 1 to 10 carbon atoms, said alkyl group being optionally substituted,
groups —C(O)OR'$_c$, R'$_c$ being selected from the group consisting of a hydrogen atom or of an alkyl group comprising from 1 to 10 carbon atoms, said alkyl group being optionally substituted,
groups —C(R$_e$)=N—(OR$_d$), R$_d$ and R$_e$ being independently selected from the group consisting of a hydrogen atom or an alkyl group comprising from 1 to 10 carbon atoms,
heterocycloalkyls comprising from 3 to 20 atoms, optionally substituted,
alkyls, comprising from 1 to 20 carbon atoms, optionally substituted with at least one substituent;
provided that at least one of $R_1$ and $R_2$ represents a group —NR$_a$R$_b$ or a group —NR'$_a$R'$_b$, respectively,
as well as its pharmaceutically acceptable salts, notably hydrochlorides, its hydrates or its polymorphic crystalline structures, its racemates, diastereoisomers or enantiomers.

According to an embodiment, the present invention relates to compounds of the following general formula (I):

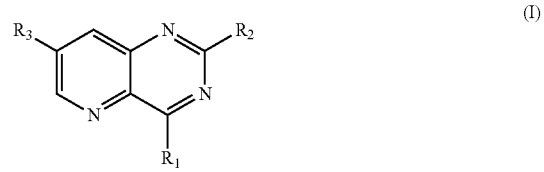

wherein:
$R_1$ is selected from the group consisting of:
(hetero)aryls comprising from 5 to 30 atoms, optionally substituted, and
groups —NR$_a$R$_b$, R$_a$ and R$_b$ forming together with the nitrogen atom to which they are bound, a heterocycle comprising from 5 to 30 atoms, optionally comprising another heteroatom selected from N, O and S, said heterocycle being optionally substituted;

$R_2$ is selected from the group consisting of:
halogen atoms selected from F, Br and I,
aryls comprising from 5 to 30 carbon atoms, optionally substituted,
groups —NR'$_a$R'$_b$, R'$_a$ and R'$_b$ forming together with the nitrogen atom to which they are bound, a heterocycle comprising from 5 to 30 atoms, optionally comprising another heteroatom selected from N, O and S, said heterocycle being optionally substituted; and $R_3$ is selected from the group consisting of:
halogen atoms selected from F, Cl and I,
alkenyls comprising from 1 to 20 carbon atoms, optionally substituted, groups —C(O)$R_c$, $R_c$ being selected from the group consisting of a hydrogen atom or of an alkyl group comprising from 1 to 10 carbon atoms, said alkyl group being optionally substituted, groups —C(O)O$R'_c$, $R'_c$ being selected from the group consisting of a hydrogen atom or of an alkyl group comprising from 1 to 10 carbon atoms, said alkyl group being optionally substituted, groups —C($R_e$)=N—(O$R_d$), $R_d$ and $R_e$ being independently selected from the group consisting of a hydrogen atom or of an alkyl group comprising from 1 to 10 carbon atoms, heterocycloalkyls comprising from 3 to 20 carbon atoms, optionally substituted, alkyls, comprising from 1 to 20 carbon atoms, optionally substituted with at least one substituent;

provided that at least one of $R_1$ and $R_2$ represents a group —N$R_a R_b$ or a group —N$R'_a R'_b$ respectively, as well as its pharmaceutically acceptable salts, its hydrates or its polymorphic crystalline structures, its racemates, diastereoisomers or enantiomers.

According to an embodiment, the present invention relates to compounds of the following general formula (I):

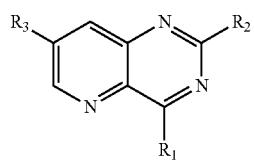

(I)

wherein:
$R_1$ is selected from the group consisting of:
(hetero)aryls comprising from 5 to 30 atoms, optionally substituted, and
groups —N$R_a R_b$, $R_a$ and $R_b$ forming together with the nitrogen atom to which they are bound, a heterocycle comprising from 5 to 30 atoms, optionally comprising another heteroatom selected from N, O and S, said heterocycle being optionally substituted;

—$R_2$ is selected from the group consisting of:
aryls comprising from 5 to 30 carbon atoms, optionally substituted,
groups —N$R'_a R'_b$, $R'_a$ and $R'_b$ forming together with the nitrogen atom to which they are bound, a heterocycle comprising from 5 to 30 atoms, optionally comprising another heteroatom selected from N, O and S, said heterocycle being optionally substituted; and $R_3$ is selected from the group consisting of:
alkenyls comprising from 1 to 20 carbon atoms, optionally substituted,
groups —C(O)$R_c$, $R_c$ being selected from the group consisting of a hydrogen atom or of an alkyl group comprising from 1 to 10 carbon atoms, said alkyl group being optionally substituted,
groups —C(O)O$R'_c$, $R'_c$ being selected from the group consisting of a hydrogen atom or of an alkyl group comprising from 1 to 10 carbon atoms, said alkyl group being optionally substituted,
groups —C($R_e$)=N—(O$R_d$), $R_d$ and $R_e$ being independently selected from the group consisting of a hydrogen atom or of an alkyl group comprising from 1 to 10 carbon atoms, heterocycloalkyls comprising from 3 to 20 atoms, optionally substituted,
alkyls, comprising from 1 to 20 carbon atoms, optionally substituted with at least one substituent;

provided that at least one of $R_1$ and $R_2$ represents a group —N$R_a R_b$ or a group —N$R'_a R'_b$, respectively, as well as its pharmaceutically acceptable salts, its hydrates or its polymorphic crystalline structures, its racemates, diastereoisomers or enantiomers.

According to an embodiment, in the group —N$R_a R_b$, $R_a$ and $R_b$ form together with the nitrogen atom to which they are bound, a heterocycle comprising from 5 to 30 atoms, optionally comprising a radical $SO_2$ or another heteroatom selected from N, O and S, said heterocycle not being substituted.

Preferably, in the group —N$R_a R_b$, $R_a$ and $R_b$ form together with the nitrogen atom to which they are bound, a non-substituted morpholine and notably the following group:

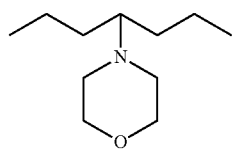

According to an embodiment, in the group —N$R'_a R'_b$, $R'_a$ and $R'_b$ form together with the nitrogen atom to which they are bound, a heterocycle comprising from 5 to 30 atoms, optionally comprising a radical $SO_2$ or another heteroatom selected from N, O and S, said heterocycle not being substituted.

Preferably, in the group —N$R'_a R'_b$, $R'_a$ and $R'_b$ form together with the nitrogen atom to which they are bound, a non-substituted morpholine and notably the following group:

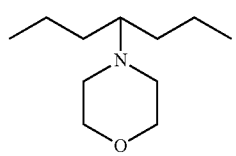

According to an embodiment, from the compounds of formula (I), mention may be made of those for which $R_3$ represents a halogen, and notably a chlorine.

According to an embodiment, among the compounds of formula (I), mention may be made of those for which $R_3$ represents an alkenyl, and preferably an allyl.

According to an embodiment, from among the compounds of formula (I), mention may be made of those for which $R_3$ represents a group —C(O)H.

According to another embodiment, from among the compounds of formula (I), mention may be made of those for which $R_3$ represents a group —C(O)OH.

According to another embodiment, from among the compounds of formula (I), mention may be made of those for which $R_3$ represents a group —C(O)O$R'_c$, wherein $R'_c$ represents an alkyl comprising from 1 to 10 carbon atoms.

According to another embodiment, from among the compounds of formula (I), mention may be made of those for which $R_3$ represents a heterocycloalkyl comprising from 3 to 20 carbon atoms, optionally substituted. In particular, $R_3$ represents a heterocycloalkyl comprising from 3 to 5 atoms, optionally substituted with at least one alkyl group, and notably two methyl groups.

According to another embodiment, from among the components of formula (I), mention may be made of those for which $R_3$ represents a group selected from —CH=N—(OH) or a group —CH=N—(OCH$_3$).

According to an embodiment, the present invention relates to the compounds of formula (I) wherein $R_3$ represents an alkyl group comprising from 1 to 20 carbon atoms, said alkyl group being optionally substituted with at least one substituent selected from the group consisting of:

OR$_f$, R$_f$ representing a group selected from a hydrogen atom or an alkyl comprising from 1 to 10 carbon atoms,
NHR$_g$, R$_g$ representing a cycloalkyl group comprising from 3 to 12 carbon atoms, optionally substituted,
NR$_h$R$_i$, with R$_h$ and R$_i$ forming a heterocycle, comprising from 5 to 30 atoms, with the nitrogen atom to which they are bound, said heterocycle optionally comprising another heteroatom selected from N, O and S, and being optionally substituted with at least one substituent selected from the group consisting of: methyl, cyclohexyl, phenyl and —SO$_2$Me;
a halogen, such as F, Cl, Br or I;
a group C(O)H,
—N$_3$,
—CN, and
a (hetero)aryl group comprising from 5 to 30 atoms, such as an isoxazole or triazole, said (hetero)aryl group being optionally substituted with at least one substituent selected from the group consisting of: —CH$_2$OH, —CH$_2$OMe, —CH$_2$NMe$_2$, —CH$_2$F, —CH$_2$OCH$_2$OMe.

Preferably, in the compounds of formula (I), $R_3$ represents an alkyl group comprising from 1 to 20 carbon atoms, preferably from 1 to 5 carbon atoms. In particular, $R_3$ represents a methyl group.

Preferably, in the compounds of formula (I), $R_3$ represents an alkyl group comprising from 1 to 20 carbon atoms, preferably from 1 to 5 carbon atoms, said alkyl group being substituted with at least one substituent selected from the group consisting of:

OH;
NH-cyclopropyl;
NH-cyclohexyl;
N-morpholine;
N-piperazine, optionally substituted with at least one substituent selected from the group consisting of: methyl, —SO$_2$Me, cyclohexyl and phenyl;
OMe;
N$_3$;
heteroaryl, and notably 1,2,3-triazole or isoxazole, substituted with at least one substituent selected from the group consisting of: —CH$_2$OH, —CH$_2$OMe, —CH$_2$NMe$_2$, —CH$_2$F, —CH$_2$OCH$_2$OMe;
CN; and
C(O)H.

DETAILED DESCRIPTION OF THE PREFERRED EMBODIMENT

According to the present invention, the "alkyl" radicals represent straight or branched chain saturated hydrocarbon radicals, comprising from 1 to 20 carbon atoms, preferably from 1 to 10 carbon atoms, and preferentially from 1 to 5 carbon atoms (they may typically be illustrated by the formula $C_nH_{2n+1}$, n representing the number of carbon atoms). Mention may notably be made, when they are linear, of the methyl, ethyl, propyl, butyl, pentyl, hexyl, octyl, nonyl, decyl and dodecyl radicals. Mention may notably be made, when they are branched or substituted with one or several alkyl radicals, of the isopropyl, tert-butyl, 2-ethylhexyl, 2-methylbutyl, 2-methylpentyl, 1-methylpentyl and 3-methylheptyl radicals.

According to the present invention, the "alkenyl" radicals represent hydrocarbon radicals with a straight or branched chain, comprising one or several ethylenic unsaturations. When they comprise a single double bond, they may typically be illustrated by the formula $C_nH_{2n}$, n representing the number of carbon atoms. From among the alkenyl radicals, mention may notably be made of allyl or vinyl radicals.

According to the present invention, the "cycloalkyl" radical is a non-aromatic saturated or partly unsaturated mono- or bi-cyclic hydrocarbon radical comprising from 3 to 20 carbon atoms, and preferably from 3 to 12 carbon atoms, such as notably cyclopropyl, cyclopentyl or cyclohexyl.

According to the present invention, the "heterocycloalkyl" or "heterocycle" radicals designate non-aromatic, saturated or partly unsaturated mono- or bicyclic systems, comprising from 3 to 20 carbon atoms, preferably from 3 to 8, comprising one or several heteroatoms, preferably from 1 to 2 heteroatoms, selected from N, O or S. As a heterocycloalkyl, mention may notably be made of morpholine, dioxolane or piperazine. When the heterocycle is substituted, mention may notably be made of N-methylpiperazine, N-methylsulfonylpiperazine, N-cyclohexylpiperazine, N-phenylpiperazine and 2.2-dimethyl-[1,3]dioxolane.

According to the present invention, by "halogen", is meant an atom selected from the group consisting of F, Cl, Br and I.

The term of "aryl" refers to a mono- or bicyclic hydrocarbon aromatic system comprising from 5 to 30, preferably from 6 to 10 carbon atoms. From among aryl radicals, mention may notably be made of the phenyl or naphthyl radical.

When the aryl radical comprises at least one heteroatom, this is referred to as a "heteroaryl" radical. Thus, the term of "heteroaryl" refers to an aromatic system comprising one or several heteroatoms selected from nitrogen, oxygen or sulphur, either mono- or bicyclic, comprising from 5 to 30, and preferably from 5 to 10, atoms. Among the heteroaryl radicals, mention may be made of 1,3,4-oxadiazolyl, isoxazole, triazolyl, 4-H-[1,2,4]triazolyl, tetrazolyl, 2H-tetrazolyl, 1,3,4-thiadiazolyl, 1,2,3-triazolyl, 1H-[1,2,3]-triazolyl, indolyl, indolizinyl, pyrimidinyl, as well as the corresponding groups derived from their fusion or from fusion with the phenyl ring.

The aforementioned "alkyl", "aryl", "heteroaryl", "alkenyl", "heterocycle", "heterocycloalkyl" and "cycloalkyl" radicals may be substituted with one or several substituents, preferably with one to five substituents, and preferentially with one to two. Among these substituents, mention may notably made of the following groups: —N$_3$, CHO, amino, amine, hydroxy, halogen, carboxyl, alkyl (optionally substituted such as with a halogen), CH$_2$OH, CH$_2$F, CF$_3$, SO$_2$alkyl, CH$_2$OMe, alkaryl, alkoxy, alkylcarbonyl, aryl (optionally substituted), aminocarbonyl, alkylcarboxyl, alkylamino, —NH-heterocycloalkyl, heterocycloalkyl (optionally substituted with a group Me, SO$_2$Me, cyclohexyl or phenyl), heteroaryl (optionally substituted with a group —CH$_2$NMe$_2$, CH$_2$F, CH$_2$OCH$_2$OMe or CH$_2$OMe), aryloxy, arylalkoxy, cyano, trifluoromethyl, —NHC(O)NH-aryl (with aryl optionally substituted for example with —CH$_2$OH), —NHC(O)NH-alkyl (with alkyl optionally substituted with a halogen), carboxyalkyl, alkoxyalkoxy or nitro.

The "alkoxy" radicals according to the present invention are radicals of formula —O-alkyl, the alkyl group being as defined earlier.

The "alkoxyalkoxy" radicals according to the present invention are radicals of formula —O-alkyl-O-alkyl, the alkyl group being as defined earlier.

The term of "alkylamino" refers to a group —NH-alkyl, the alkyl group being as defined above.

The term of "alkylcarbonyl" refers to a group —CO-alkyl, the alkyl group being as defined above.

The term of "alkylcarboxyl" designates a group —COO-alkyl, the alkyl group being defined as above.

Among halogen atoms, mention may more particularly be made of fluorine, chlorine, bromine or iodine atoms.

The term of "aryloxy" refers to a group —O-aryl, the aryl group being as defined above.

The term of "arylalkoxy" refers to an aryl-alkoxy group, the aryl and alkoxy groups being as defined above.

The term of "carboxyalkyl" refers to a group HOOC-alkyl, the alkyl group being as defined above. As an example of carboxyalkyl groups, mention may notably be made of carboxymethyl or carboxyethyl.

When an alkyl radical is substituted with an aryl group, this will be referred to as an "arylalkyl" or "aralkyl" radical. The "arylalkyl" or "aralkyl" radicals are aryl-alkyl-radicals, the aryl and alkyl groups being as defined above. From among arylalkyl radicals, mention may notably be made of the benzyl or phenethyl radical.

From among the aryl or heteroaryl groups, either substituted or not, mention may more particularly be made of the following groups:

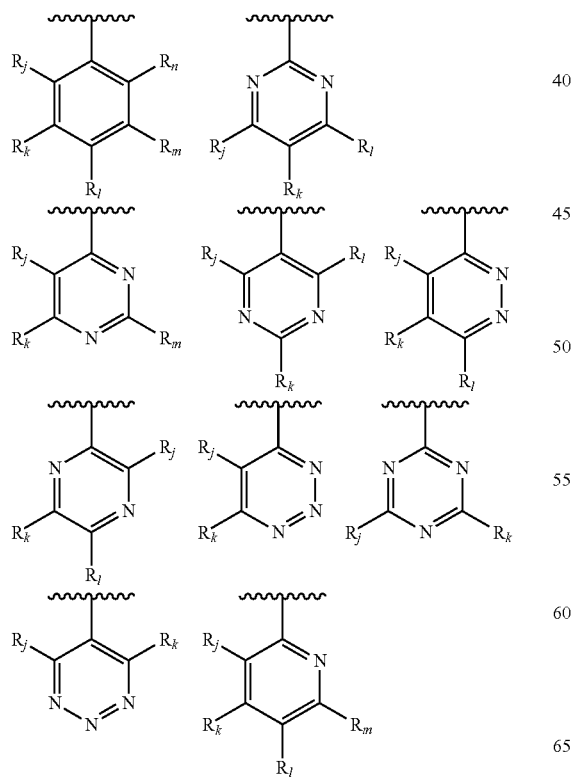
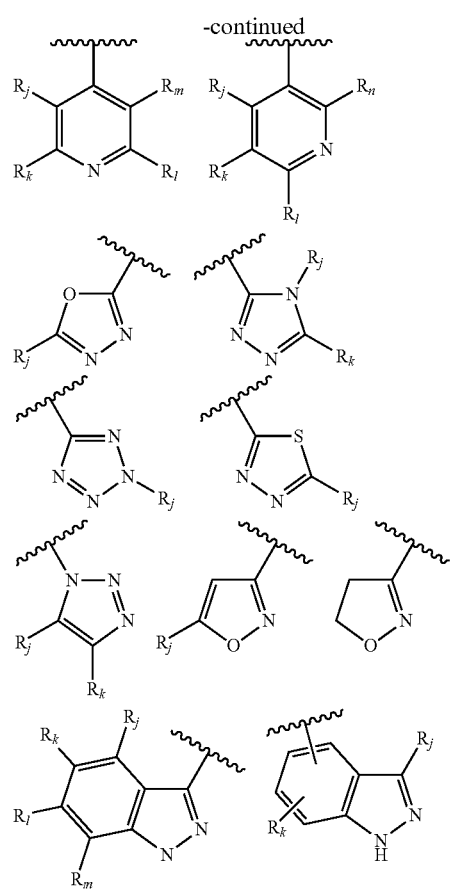

the groups $R_j$, $R_k$, $R_l$, $R_m$, and $R_n$, being selected independently of each other from the group consisting of the following substituents:
a hydrogen atom,
a halogen atom,
an alkyl group comprising from 1 to 10 carbon atoms, and preferably being a methyl group,
  said alkyl group being optionally substituted, notably with one or several substituents selected from the group consisting of:
    a halogen atom,
    a group OR'$_\alpha$, R'$_\alpha$ representing a hydrogen atom or an alkyl group comprising from 1 to 10 carbon atoms, preferably from 1 to 5 carbon atoms,
    a group NR'$_\beta$R'$_\gamma$, R'$_\beta$ and R'$_\gamma$ representing an alkyl group comprising from 1 to 10 carbon atoms,
    a group NR$_a$R$_b$, R$_a$ and R$_b$ being as defined earlier,
    a group COR'$_\alpha$, R'$_\alpha$ being as defined above,
    a group COOR'$_\alpha$, R'$_\alpha$ being as defined above,
a group —NO$_2$,
a group OR'$_\alpha$, R'$_\alpha$ being as defined above,
a group —O—(CH$_2$)$_n$—O—R'$_\alpha$, R'$_\alpha$ being as defined above, and preferably representing an alkyl group, and n representing an integer comprised from 1 to 10, preferably equal to 1, notably a group —OCH$_2$OCH$_3$,
a group —NR'$_\beta$R'$_\gamma$, R'$_\beta$ and R'$_\gamma$ being as defined above, notably a group NH$_2$,
a group —NH—C(O)—NHR'$_\lambda$, wherein R'$_\lambda$ may be selected from the group consisting of the hydrogen atom, alkyl groups comprising from 1 to 10 carbon atoms, aryl groups comprising from 5 to 30 carbon atoms and heteroaryls comprising from 5 to 30 atoms, said alkyl, aryl and heteroaryl groups being optionally substituted;

a group —SO$_2$NHR"$_\gamma$, R"$_\gamma$ being such that it may be selected from the group consisting of the hydrogen atom, alkyl groups comprising from 1 to 10 carbon atoms, aryl groups comprising from 5 to 30 carbon atoms and heteroaryls comprising from 5 to 30 atoms, said alkyl, aryl and heteroaryl groups being optionally substituted.

According to an embodiment, the radical R'$_\lambda$ is selected from the group consisting of aryl groups, such as a phenyl, and alkyl groups, such as a methyl or an ethyl; said aryl and alkyl groups being optionally substituted with a halogen or a group —CH$_2$OH.

According to an embodiment, the radical R'$_\lambda$ is selected from the group consisting of:

an alkyl such as methyl, —CH$_2$CF$_3$,

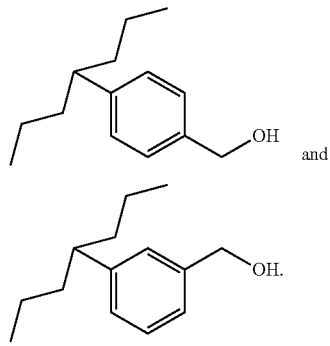

and

From among the aryl groups, mention may be made of:

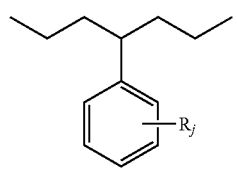

R$_j$ being as defined above, and being preferably selected from the group consisting of: H, OCH$_2$OCH$_3$, OH, OMe, CH$_2$OH, NO$_2$, NH$_2$ and NH—C(O)NHR'$_\lambda$, R'$_\lambda$ being as defined above. In particular, R$_j$ represents one of the following groups:

—NH—C(O)NHalkyl, NH—C(O)NHCH$_2$CF$_3$,

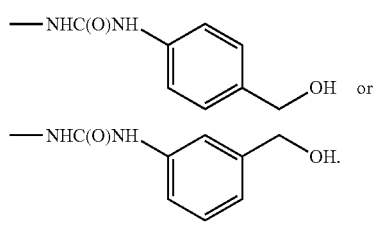

or

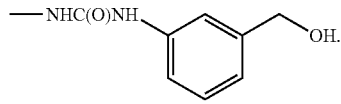

From among heteroaryl groups, mention may be made of:

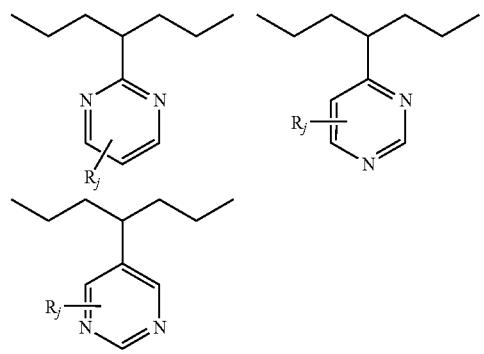

R$_j$ being as defined above, and being preferably selected from the group consisting of: a hydrogen atom; a halogen, preferably a chlorine or fluorine atom; CF$_3$; a group NR'$_\beta$R'$_\gamma$, R'$_\beta$ and R'$_\gamma$ being as defined above, notably a group NH$_2$; a group —O—(CH$_2$)$_n$—O—R'$_\alpha$, n and R'$_\alpha$ being as defined above; a group —NH—C(O)—NHR'$_\lambda$, being as defined earlier, and notably —NH—C(O)—NH$_2$; and a group —SO$_2$NHR"$_\gamma$, R"$_\gamma$ being as defined above, and notably —SO$_2$NH$_2$.

From among heteroaryl groups, mention may be made of:

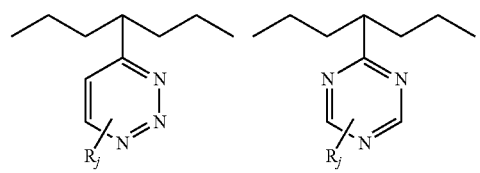

R$_j$ being as defined above, and being preferably selected from the group consisting of: a hydrogen atom; a halogen, preferably a chlorine or fluorine atom; CF$_3$; a group NR'$_\beta$R'$_\gamma$, R'$_\beta$ and R'$_\gamma$ being as defined above, notably a group NH$_2$; a group —O—(CH$_2$)$_n$—O—R'$_\alpha$, R'$_\alpha$ being as defined above; a group —NH—C(O)—NHR'$_\lambda$, R'$_\lambda$ being as defined earlier, and notably —NH—C(O)—NH$_2$; and a group —SO$_2$NHR"$_\gamma$, R"$_\gamma$ being as defined above, and notably —SO$_2$NH$_2$.

From among heteroaryl groups, mention may be made of:

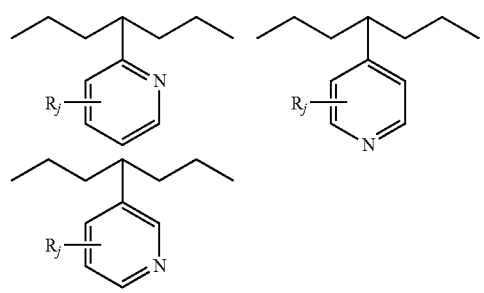

R$_j$ being as defined above, and being preferably selected from the group consisting of: a hydrogen atom; a halogen, preferably a chlorine or fluorine atom; CF$_3$; a group NR'$_\beta$R'$_\gamma$, R'$_\beta$ and R'$_\gamma$ being as defined above, notably a group NH$_2$; a group —O—(CH$_2$)$_n$—O—R'$_\alpha$, R'$_\alpha$ being as defined above; a group —NH—C(O)—NHR'$_\lambda$, R'$_\lambda$ being as defined earlier, and notably —NH—C(O)—NH$_2$; and a group —SO$_2$NHR"$_\gamma$, R"$_\gamma$ being as defined above, and notably —SO$_2$NH$_2$.

From among heteroaryl groups, mention may be also be made of:

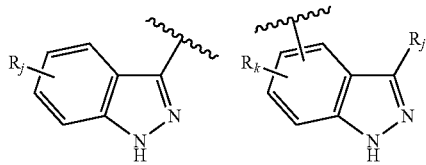

R$_j$ and R$_k$ being as defined above, and being preferably selected independently of each other in the group consisting of: a hydrogen atom; a halogen, preferably a chlorine or fluorine atom; CF$_3$; a group NR'$_\beta$R'$_\gamma$, R'$_\beta$ and R'$_\gamma$ being as defined above, notably a group NH$_2$; a group —O—(CH$_2$)$_n$—O—R'$_\alpha$, R'$_\alpha$ being as defined above; a group —NH—C(O)—NHR'$_\lambda$, R'$_\lambda$ being as defined earlier, and notably —NH—C(O)—NH$_2$; and a group —SO$_2$NHR"$_\gamma$, R"$_\gamma$ being as defined above, and notably —SO$_2$NH$_2$.

From among heteroaryls, mention may also be made of:

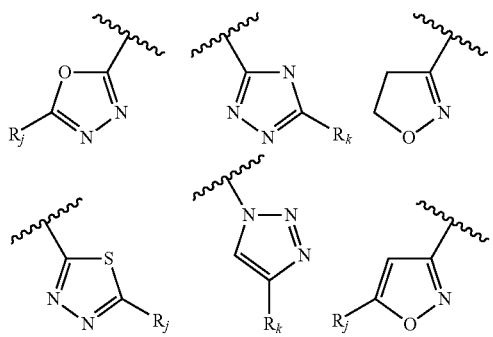

R$_j$ and R$_k$ being as defined above, and preferably R$_j$ and R$_k$ represent independently of each other a hydrogen atom or an alkyl group comprising from 1 to 10 carbon atoms, optionally substituted, preferably with a substituent selected from the following group:
a halogen atom, such as F;
a group OR'$_\alpha$, R'$_\alpha$ being as defined above, preferably OH or OCH$_3$, a group NR$_a$R$_b$, R$_a$ and R$_b$ being as defined earlier, preferably selected from a morpholine, a piperidine, a N-methylpiperidine, a piperazine or a N-methylpiperazine,
a group COOH or COOCH$_3$;
a group NR'$_\beta$R'$_\gamma$, with R'$_\beta$ and R'$_\gamma$ being as defined earlier, preferably R'$_\beta$ and R'$_\gamma$ representing Me;
a group —O—(CH$_2$)$_n$—OR'$_\alpha$, with n and R'$_\alpha$ being as defined earlier.

From among heteroaryls, mention may also be made of:

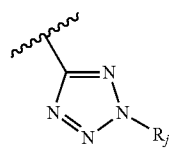

R$_j$ being as defined above, and preferably R$_j$ represents an alkyl group.

The expression "pharmaceutical acceptable salts" refers to relatively non-toxic, inorganic and organic acid addition salts, and base addition salts of the compounds of the present invention. These salts may be prepared in situ during the final isolation and purification of the compounds. In particular, the acid addition salts may be prepared by reacting separately the purified compound in its purified form with an organic or inorganic acid and by isolating the thereby formed salt. Among the examples of acid addition salts, are found hydrobromide, hydrochloride, sulphate, bisulphate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lactobionate, salts, sulfamates, malonates, salicylates, propionates, methylenebis-b-hydroxynaphthoates, gentisic acid, isethionates, di-p-toluoyltartrates, methanesulfonates, ethanesulfonates, benzenesulfonates, p-toluenesulfonates, cyclohexylsulfamates and quinateslaurylsulfonate, and the like (see for example S. M. Berge et al. "Pharmaceutical Salts" *J. Pharm. Sci,* 66: p. 1-19 (1977)). The acid addition salts may also be prepared by reacting separately the purified compound in its acid form with an organic or inorganic base and by isolating the thereby formed salt. Acid addition salts comprise amine and metal salts. Suitable metal salts comprise the salts of sodium, potassium, calcium, barium, zinc, magnesium and aluminium. Sodium and potassium salts are preferred. Suitable inorganic base addition salts are prepared from metal bases which comprise sodium hydride, sodium hydroxide, potassium hydroxide, calcium hydroxide, aluminium hydroxide, lithium hydroxide, magnesium hydroxide, zinc hydroxide. Suitable base addition amine salts are prepared from amines which have sufficient alkalinity in order to form a stable salt, and preferably comprise amines which are often used in medicinal chemistry because of their low toxicity and of their acceptability for medical use: ammonia, ethylenediamine, N-methyl-glucamine, lysine, arginine, ornithine, choline, N,N'-dibenzylethylenediamine, chloroprocaine, diethanolamine, procaine, N-benzyl-phenethylamine, diethylamine, piperazine, tris(hydroxymethyl)-aminomethane, tetramethyl-ammonium hydroxide, triethylamine, dibenzylamine, ephenamine, dehydroabietylamine, N-ethylpiperidine, benzylamine, tetra-methylammonium, tetraethylammonium, methylamine, dimethylamine, trimethylamine, ethylamine, basic amino acids, for example lysine and arginine, and dicyclohexylamine, and the like.

The invention also relates to tautomeric forms, to enantiomers, diastereoisomers, epimers and to organic or mineral salts of the compounds of general formula (I).

A family according to the present invention consists of compounds of formula (I) in which R$_1$ represents a (hetero) aryl comprising from 5 to 30 carbon atoms optionally substituted.

According to an embodiment, the present invention relates to compounds of formula (I) as defined above, wherein R$_1$ represents a heteroaryl comprising from 5 to 30 atoms, optionally substituted.

Preferably, R$_1$ represents an indazole or a pyrimidine, optionally substituted with a substituent selected from the group consisting of a halogen atom, notably a chlorine atom, or a group —NR'$_\beta$R'$_\gamma$, R'$_\beta$ and R'$_\gamma$ being as defined above, notably a group NH$_2$.

Preferentially, R$_1$ represents one of the following heteroaryls:

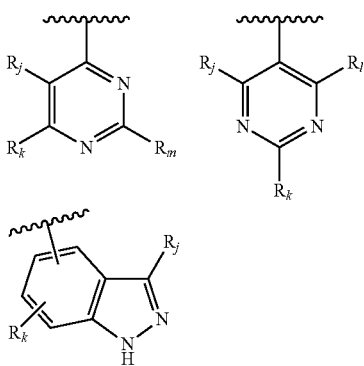

wherein, $R_j$, $R_k$, $R_l$ and $R_m$ are as defined above.

In particular, $R_j$, $R_k$, $R_l$ and $R_m$ are independently selected from a hydrogen atom, a chlorine and a group —NH$_2$.

Preferably, $R_1$ represents a pyridazine or a pyrazine optionally substituted. In particular, the pyridazines and pyrazines are substituted with a substituent selected from the group consisting of a halogen atom, notably a chlorine atom, or a group —NR'$_\beta$R'$_\gamma$, R'$_\beta$ and R'$_\gamma$ being as defined above, notably a group NH$_2$.

Preferentially, $R_1$ represents one of the following heteroaryls:

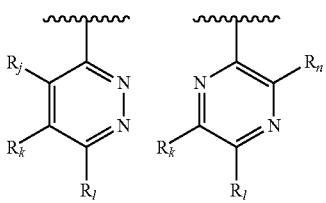

wherein, $R_j$, $R_k$, $R_l$ and $R_m$ are as defined above.

Preferably, $R_1$ represents a triazine or a pyridine, optionally substituted. In particular, the triazines and pyridines are substituted with a substituent selected from the group consisting of a halogen atom, notably a chlorine atom, or of a group —NR'$_\beta$R'$_\gamma$, R'$_\beta$ and R'$_\gamma$ being as defined above, notably a group NH$_2$.

Preferentially, $R_1$ represents one of the following heteroaryls:

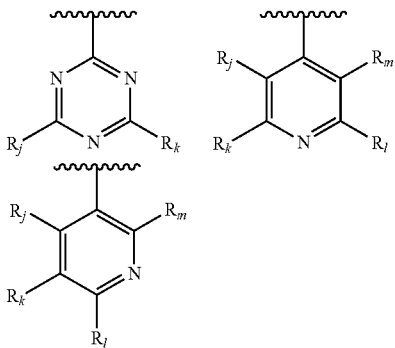

wherein, $R_j$, $R_k$, $R_l$ and $R_m$, are as defined above. In particular, $R_j$, $R_k$, $R_l$ and $R_m$, are independently selected from a hydrogen atom, a chlorine and a group —NH$_2$.

According to another embodiment, the present invention relates to the compounds of formula (I) as defined above, wherein $R_1$ represents an aryl comprising from 5 to 30 carbon atoms, optionally substituted.

Preferably, in formula (I), $R_1$ represents a phenyl group, optionally substituted. In particular, $R_1$ represents a phenyl group, substituted with at least one substituent selected from the group consisting of:
- an alkyl group comprising from 1 to 10 carbon atoms, and being preferably a methyl group, said alkyl group being optionally substituted notably with one or several substituents OR'$_\alpha$, R'$_\alpha$ notably representing a hydrogen atom or a methyl group,
- a group —NO$_2$,
- a group OR'$_\alpha$, R'$_\alpha$ being as defined above, and preferably representing a hydrogen atom or a methyl,
- a group —O—(CH$_2$)$_n$—O—R'$_\alpha$, R'$_\alpha$ and n being as defined above, and R'$_\alpha$ preferably representing a methyl group, and n preferably representing 1,
- a group —NR'$_\beta$R'$_\gamma$, R'$_\beta$ and R'$_\gamma$ being as defined above, notably a group NH$_2$,
- a group —NH—C(O)—NHR'$_\lambda$, R'$_\lambda$, being as defined above.

In particular, the present invention relates to the compounds of formula (I), wherein $R_1$ represents a following aryl group:

(E)

$R_j$ being as defined above, and being preferably selected from the group consisting of: H, OCH$_2$OCH$_3$, OH, OMe, CH$_2$OH, NO$_2$, NH$_2$ and NH—C(O)NHR'$_\lambda$, R'$_\lambda$ being as defined above.

From among the compounds according to the invention, mention may be made of those for which $R_1$ represents a group (E), wherein $R_j$ represents an —OH group, preferably in a meta position.

Among the compounds according to the invention, mention may be made of those for which $R_1$ represents a group (E), wherein $R_j$ represents an —OH group, preferably in an ortho position.

Among the compounds according to the invention, mention may be made of those for which $R_1$ represents a group (E), wherein $R_j$ represents an —OH group, preferably in a para position.

Among the compounds according to the invention, mention may be made of those for which $R_1$ represents a group (E), wherein $R_j$ represents a —CH$_2$OH group, preferably in a meta position.

Among the compounds according to the invention, mention may be made of those for which $R_1$ represents a group (E), wherein $R_j$ represents a —CH$_2$OH group, preferably in a para position.

Among the compounds according to the invention, mention may be made of those for which $R_1$ represents a group (E), wherein $R_j$ represents a group —NHC(O)NHR'$_\lambda$, preferably in a para position.

Among the compounds according to the invention, mention may be made of those for which $R_1$ represents a group (E), wherein $R_j$ represents a —NO$_2$ group, preferably in a para position.

Among the compounds according to the invention, mention may be made of those for which $R_1$ represents a group (E), wherein $R_j$ represents a —$NH_2$ group, preferably in a para position.

According to a particular embodiment, $R_1$ represents one of the following aryl groups:

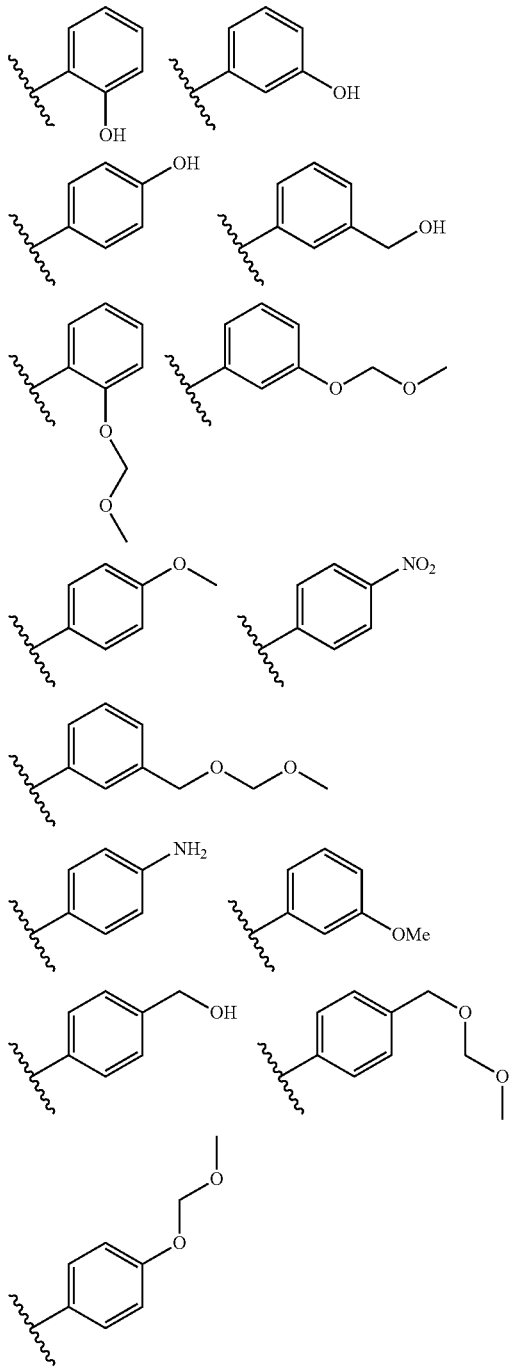

According to a particular embodiment, $R_1$ represents the following aryl group:

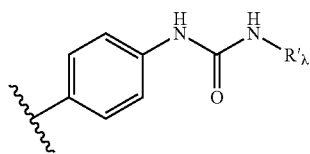

$R'_\lambda$ being as defined above. Preferably, $R'_\lambda$ represents an aryl group and notably a phenyl, optionally substituted with a $CH_2OH$ group.

In particular, $R_1$ represents the following aryl group:

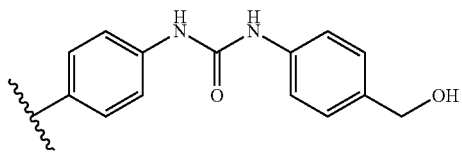 [SMILES: *c1ccc(NC(=O)Nc2ccc(CO)cc2)cc1]

Another family according to the present invention consists of compounds of formula (I) wherein $R_1$ represents groups —$NR_aR_b$, $R_a$ and $R_b$ being as defined above.

According to an embodiment, the present invention relates to the compounds of formula (I) as defined above, wherein $R_1$ represents one of the following groups:

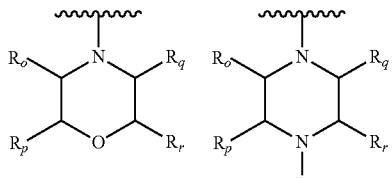

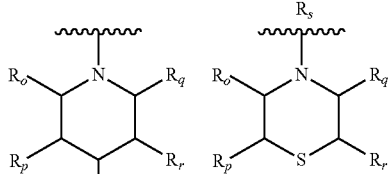

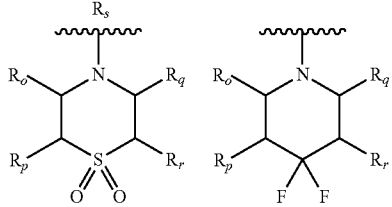

wherein, $R_o$, $R_p$, $R_q$, $R_r$ and $R_s$ represent independently of each other a substituent selected from the group consisting of: a hydrogen atom, an alkyl group comprising from 1 to 10 carbon atoms, a group —$OR'_\alpha$—$R'_\alpha$, being as defined above and a group —$NR'_\beta R'_\gamma$, $R'_\beta$ and $R'_\gamma$ being as defined above, or $R_r$ and $R_p$ form together a ring comprising from 2 to 3 carbon atoms.

In particular, among the compounds of formula (I), mention may be made of those for which $R_o$, $R_p$, $R_q$, $R_r$ and $R_s$ represent a hydrogen atom.

Preferably, $R_1$ represents the following group:

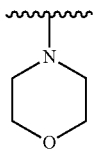

A family according to the present invention consists of compounds of formula (I) wherein $R_2$ represents a heteroaryl comprising from 5 to 30 atoms, optionally substituted.

Preferably, $R_2$ represents an indazole or a pyrimidine, optionally substituted with a substituent selected from the group consisting of a halogen atom, notably a chlorine atom, or of a group —$NR'_\beta R'_\gamma$, $R'_\beta$ and $R'_\gamma$ being as defined above, notably a group $NH_2$.

Preferentially, $R_2$ represents one of the following heteroaryls:

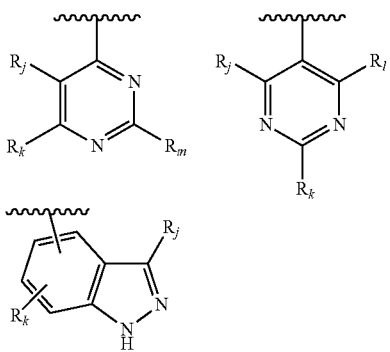

wherein, $R_j$, $R_k$, $R_l$ and $R_m$, are as defined above. In particular, $R_j$, $R_k$, $R_l$ and $R_m$, are independently selected from a hydrogen atom, a chlorine and a group —$NH_2$.

Preferably, $R_2$ represents a pyridazine or a pyrazine optionally substituted. In particular, the pyridazines and pyrazines are substituted with a substituent selected from the group consisting of a halogen atom, notably a chlorine atom, or a group —$NR'_\beta R'_\gamma$, $R'_\beta$ and $R'_\gamma$ being as defined above, notably a group $NH_2$.

Preferentially, $R_2$ represents one of the following heteroaryls:

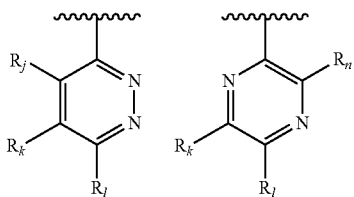

wherein, $R_j$, $R_k$, $R_l$ and $R_m$ are as defined above.

Preferably, $R_2$ represents a triazine or a pyridine, optionally substituted. In particular, the triazines and pyridines are substituted with a substituent selected from the group consisting of a halogen atom, notably a chlorine atom, or of a group —$NR'_\beta R'_\gamma$, $R'_\beta$ and $R'_\gamma$ being as defined above, notably a group $NH_2$.

Preferentially, $R_2$ represents one of the following heteroaryls:

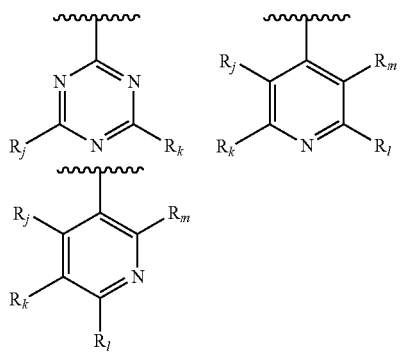

wherein, $R_j$, $R_k$, $R_l$ and $R_m$, are as defined above. In particular, $R_j$, $R_k$, $R_l$ and $R_m$, are independently selected from a hydrogen atom, a chlorine and a group —$NH_2$.

According to another embodiment, the present invention relates to the compounds of formula (I) as defined above, wherein $R_2$ represents aryls comprising from 5 to 30 carbon atoms, optionally substituted.

Preferably, in formula (I), $R_2$ represents a phenyl group, optionally substituted. In particular, $R_2$ represents a phenyl group, substituted with a substituent selected from the group consisting of:
- an alkyl group comprising from 1 to 10 carbon atoms, and being preferably a methyl group, said alkyl group being optionally substituted notably with one or several substituents $OR'_\alpha$, $R'_\alpha$ notably representing a hydrogen atom or a methyl group,
- a group —$NO_2$,
- a group $OR'_\alpha$, $R'_\alpha$ being as defined above, and preferably representing a hydrogen atom or a methyl,
- a group —O—$(CH_2)_n$—O—$R'_\alpha$, $R'_\alpha$ and n being as defined above, and $R'_\alpha$ preferably representing a methyl group, and n preferably representing 1,
- a group —$NR'_\beta R'_\gamma$, $R'_\beta$ and $R'_\gamma$ being as defined above, notably a group $NH_2$,
- a group —NH—C(O)—$NHR'_\lambda$, $R'_\lambda$ being as defined above.

In particular, the present invention relates to the compounds of formula (I), wherein $R_2$ represents a following aryl group:

(E)

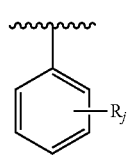

$R_j$ being as defined above, and being preferably selected from the group consisting of: H, $OCH_2OCH_3$, OH, OMe, $CH_2OH$, $NO_2$, $NH_2$ and NH—C(O)$NHR'_\lambda$, $R'_\lambda$ being as defined above.

From among the compounds according to the invention, mention may be made of those for which $R_2$ represents a group (E), wherein $R_j$ represents an —OH group, preferably in the meta position.

From among the compounds according to the invention, mention may be made of those for which $R_2$ represents a group (E), wherein $R_j$ represents an —OH group, preferably in the ortho position.

From among the compounds according to the invention, mention may be made of those for which $R_2$ represents a group (E), wherein $R_j$ represents an —OH group, preferably in the para position.

From among the compounds according to the invention, mention may be made of those for which $R_2$ represents a group (E), wherein $R_j$ represents a —CH$_2$OH group, preferably in the meta position.

From among the compounds according to the invention, mention may be made of those for which $R_2$ represents a group (E), wherein $R_j$ represents a —CH$_2$OH group, preferably in the para position.

From among the compounds according to the invention, mention may be made of those for which $R_2$ represents a group (E), wherein $R_j$ represents a group —NHC(O)NHR'$_\lambda$, preferably in the para position. Mention may notably be made of compounds for which $R_2$ represents a group (E), wherein $R_j$ represents a group —NHC(O)NHR'$_\lambda$, with R'$_\lambda$ representing an alkyl or aryl optionally substituted. Preferably, $R_j$ represents one of the following groups:

NH—C(O)NHCH$_2$CF$_3$,

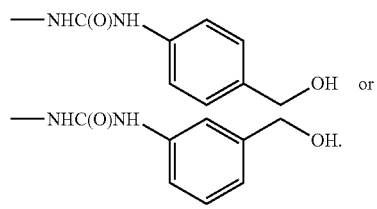

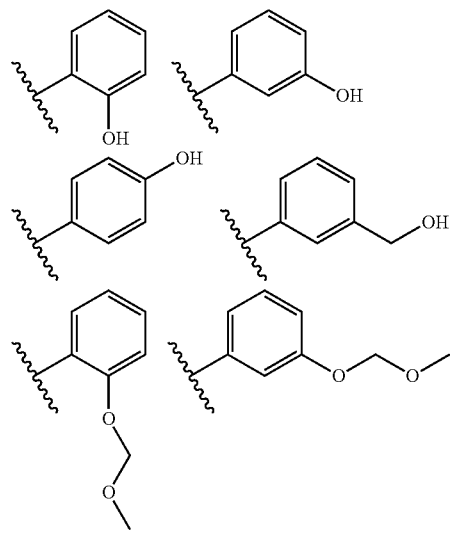

From among the compounds according to the invention, mention may be made of those for which $R_2$ represents a group (E), wherein $R_j$ represents a —NO$_2$ group, preferably in the para position.

From among the compounds according to the invention, mention may be made of those for which $R_2$ represents a group (E), wherein $R_j$ represents a —NH$_2$ group, preferably in the para position.

According to a particular embodiment, $R_2$ represents one of the following aryl groups:

-continued

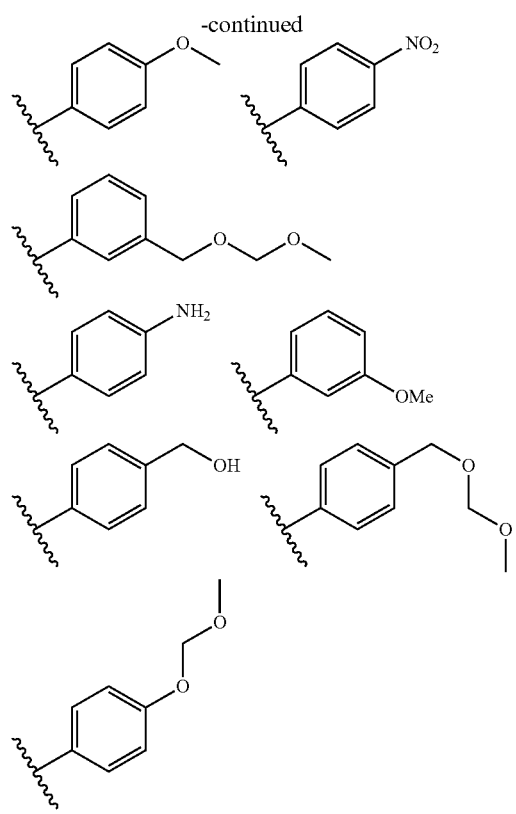

According to a particular embodiment, $R_2$ represents the following aryl group:

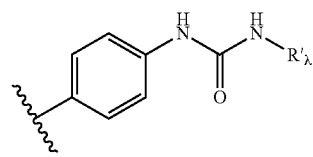

R'$_\lambda$ being as defined above.

Preferably, R'$_\lambda$ represents an aryl group, and notably a phenyl, optionally substituted with a CH$_2$OH group.

In particular, $R_2$ represents the following aryl group:

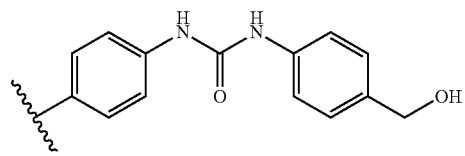 [SMILES: *c1ccc(NC(=O)Nc2ccc(CO)cc2)cc1]

In particular, $R_2$ represents the following aryl group:

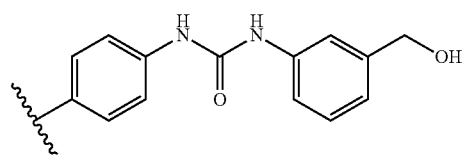 [SMILES: *c1ccc(NC(=O)Nc2cccc(CO)c2)cc1]

Preferably, R'$_\lambda$ represents an alkyl group, and notably a methyl or an ethyl, optionally substituted with a halogen. In particular, R'$_\lambda$ represents —CH$_2$CF$_3$.

In particular, R$_2$ represents the following aryl group:

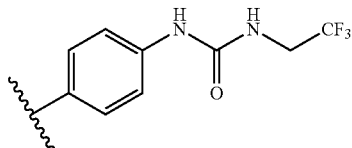 [SMILES: *c1ccc(NC(=O)NCC(F)(F)F)cc1]

Another family according to the present invention consists of compounds of formula (I) wherein R$_2$ represents groups —NR$_a$R$_b$, R$_a$ and R$_b$ being as defined above.

According to an embodiment, the present invention relates to the compounds of formula (I) as defined above, wherein R$_2$ represents one of the following groups:

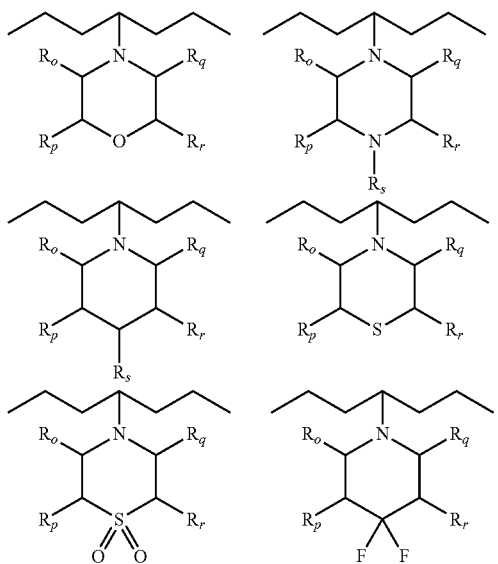

wherein, R$_o$, R$_p$, R$_q$, R$_r$ and R$_s$ represent independently of each other, a substituent selected from the group consisting of: a hydrogen atom, an alkyl group comprising from 1 to 10 carbon atoms, a group —OR'$_\alpha$, R'$_\alpha$ being as defined above and a group —NR'$_\beta$R'$_\gamma$, R'$_\beta$ and R'$_\gamma$ being as defined above, or R$_r$ and R$_p$ form together a ring comprising from 2 to 3 carbon atoms.

In particular, among the compounds of formula (I), mention may be made of those for which R$_o$, R$_p$, R$_q$, R$_r$ and R$_s$ represent a hydrogen atom.

Preferably, R$_2$ represents the following group:

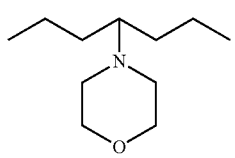

Another family according to the present invention consists of compounds of formula (I) wherein R$_2$ represents a halogen atom selected from F, Br and I.

From among the compounds of the invention, mention may notably be made of the compounds of the following formula (I-1):

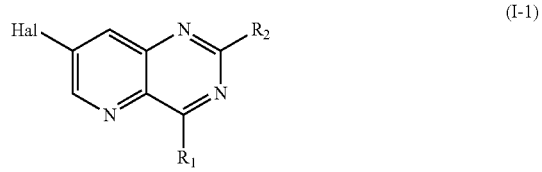

wherein Hal represents a halogen, and R$_1$ and R$_2$ being as defined earlier.

The compounds of formula (I-1) correspond to compounds of formula (I), wherein R$_3$ represents a halogen.

From among the compounds of formula (I-1), mention may notably be made of the compounds of formulae (I-1-1) and (I-1-2) which follow:

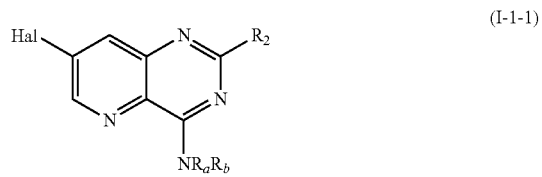

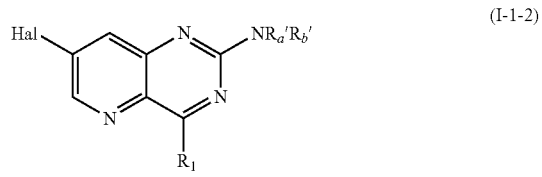

wherein Hal, R$_1$, R$_2$, R$_a$, R$_b$, R'$_a$ and R'$_b$ are as defined earlier, According to an embodiment, in the compounds of formulae (I-1), (I-1-1) and (I-1-2), Hal represents a halogen and preferably a chlorine atom.

According to another embodiment, in the compounds of formulae (I-1) and (I-1-2), R$_1$ is selected from the group consisting of (hetero)aryls comprising from 5 to 30 atoms, optionally substituted.

According to another embodiment, in the compounds of formulae (I-1) and (I-1-1), R$_2$ is selected from the group consisting of:
halogens selected from F, Br and I,
aryls comprising from 5 to 30 carbon atoms, optionally substituted.

From among the compounds of the invention, mention may also be made of the compounds of the following formula (I-2):

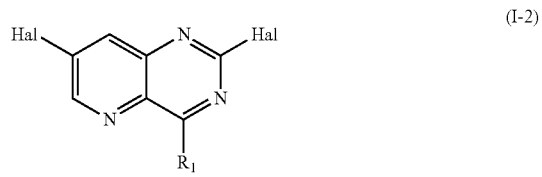

wherein R$_1$ represents a group —NR$_a$R$_b$, R$_a$ and R$_b$ being as defined above and Hal represents a halogen atom, and notably a chlorine atom.

According to an embodiment, in formula (I-2), $R_1$ is selected from one of the following groups:

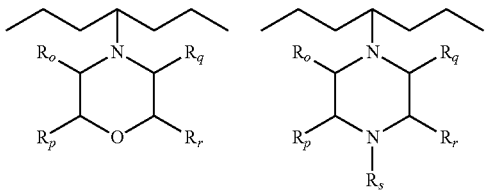
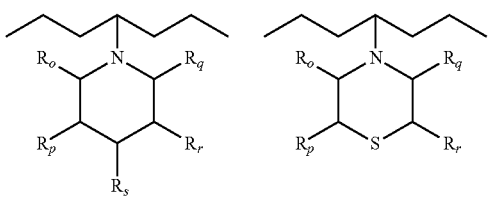
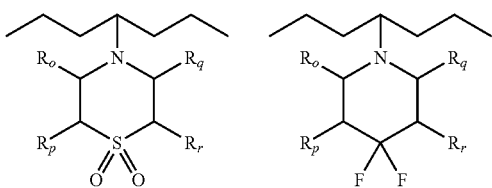

$R_o$, $R_p$, $R_q$, $R_r$ and $R_s$ are as defined above.

Compounds of the following formula (I-2-1) are described:

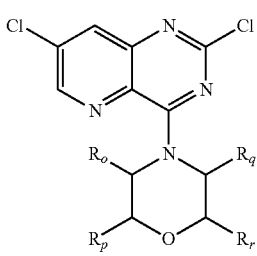

(I-2-1)

$R_o$, $R_p$, $R_q$ and $R_r$ being as defined above.

Preferably, $R_o$, $R_p$, $R_q$ and $R_r$ represent a hydrogen atom. Thus, a compound fitting the following formula is described:

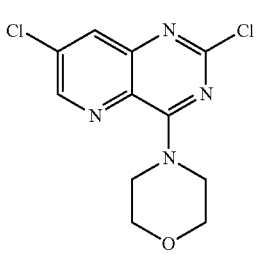 [SMILES: Clc1cnc2c(N3CCOCC3)nc(Cl)nc2c1]

A class of compounds according to the invention consists of compounds of the following formula (I-3):

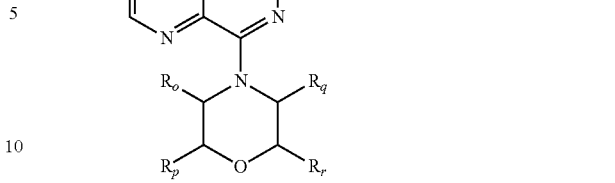

(I-3)

$R_2$, $R_3$, $R_o$, $R_p$, $R_q$ and $R_r$ being as defined above.

From among the compounds of formula (I-3), the present invention relates to compounds of the following formula (I-3-1):

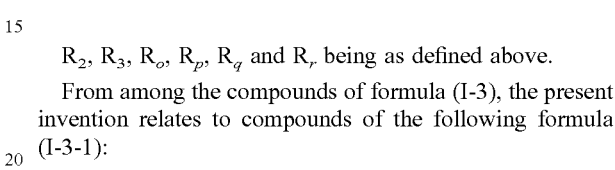

wherein, $R_2$ and $R_3$ are as defined above.

The compounds of formula (I-3-1) according to the invention, correspond to the compounds of formula (I-3) wherein $R_o$, $R_p$, $R_q$ and $R_r$ represent a hydrogen atom.

According to an embodiment, in the compounds of formulae (I-3) and (I-3-1), $R_2$ represents a halogen atom selected from F, Br and I.

According to another embodiment, in the compounds of formulae (I-3) and (I-3-1), $R_2$ represents an aryl group comprising from 5 to 30 carbon atoms, said aryl group being optionally substituted.

Preferably, the aryl group is the following group:

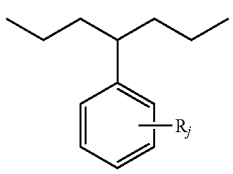

$R_j$ being as defined above, and preferably selected from: H, $OCH_2OCH_3$, OH, OMe, $CH_2OH$, $NO_2$, $NH_2$ and NH—C(O)$NHR'_\lambda$, $R'_\lambda$ being as defined above. In particular, $R'_\lambda$ represents an alkyl, aryl or heteroaryl group, said alkyl, aryl or heteroaryl groups being optionally substituted with at least one substituent selected from a —$NH_2$ group, a halogen, —OH, —$CH_2OH$, $CF_3$, alkoxy, —O—$(CH_2)_xOCH_3$, x being an integer comprised from 1 to 10, and —COOH.

According to an embodiment, in the compounds of formulae (I-3) and (I-3-1) according to the invention, $R_2$ represents one of the following groups:

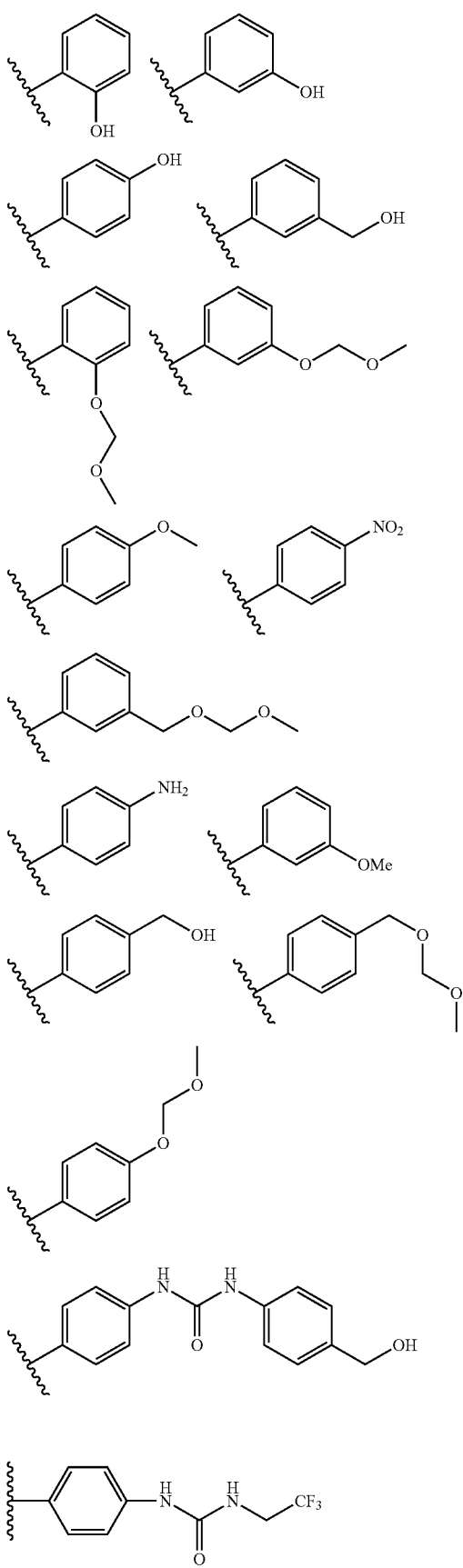

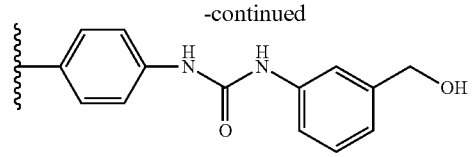

According to an embodiment, in the compounds of formulae (I-3) and (I-3-1), $R_3$ represents a halogen atom, and notably a chlorine.

According to another embodiment, in the compounds of formulae (I-3) and (I-3-1), $R_3$ represents an alkenyl group comprising from 1 to 20 carbon atoms optionally substituted. Preferably $R_3$ represents an allyl.

According to another embodiment, in the compounds of formulae (I-3) and (I-3-1), $R_3$ represents a group —C(O)$R_c$, $R_c$ preferably representing a hydrogen atom.

According to another embodiment, in the compounds of formulae (I-3) and (I-3-1), $R_3$ represents a group —C(O)OR'$_c$, R'$_c$ preferably representing a hydrogen atom.

According to another embodiment, in the compounds of formulae (I-3) and (I-3-1), $R_3$ represents a group —C($R_e$)=N—(OR$_d$), $R_d$ and $R_e$ being as defined above. Preferably, $R_e$ represents a hydrogen atom and $R_d$ represents a hydrogen atom or a methyl group.

According to another embodiment, in the compounds of formulae (I-3) and (I-3-1), $R_3$ represents a heterocycloalkyl group comprising from 3 to 20 carbon atoms, said group being optionally substituted. In particular, $R_3$ represents the following group:

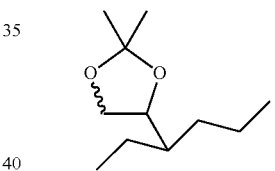

According to another embodiment, in the compounds of formulae (I-3) and (I-3-1), $R_3$ represents an alkyl group comprising from 1 to 20 carbon atoms, said alkyl group being optionally substituted with at least one substituent selected from the group consisting of:
OR$_f$, R$_f$ being as defined earlier,
NHR$_g$, R$_g$ being as defined earlier,
NR$_h$R$_i$, with R$_h$ and R$_j$ being as defined earlier,
a halogen,
$N_3$,
CN, and
a (hetero)aryl group comprising from 5 to 30 atoms, said (hetero)aryl group being optionally substituted with at least one substituent selected from the group consisting of: —CH$_2$OH, —CH$_2$OMe, —CH$_2$NMe$_2$, —CH$_2$F, —CH$_2$OCH$_2$OMe.

Preferably, in the compounds of formulae (I-3) and (I-3-1), $R_3$ represents an alkyl group comprising from 1 to 20 carbon atoms, preferably from 1 to 5 carbon atoms, such as a methyl.

Preferably, in the compounds of formulae (I-3) and (I-3-1), $R_3$ represents an alkyl group comprising from 1 to 20 carbon atoms, preferably from 1 to 5 carbon atoms, said alkyl group being substituted with at least one substituent selected from the group consisting of:

OH;

NH-cyclopropyl;

NH-cyclohexyl;

N-morpholine;

N-piperazine, optionally substituted with at least one substituent selected from the group consisting of: methyl, —SO$_2$Me, cyclohexyl and phenyl;

OMe;

N$_3$;

heteroaryl, and notably 1,2,3-triazole or isoxazole, substituted with at least one substituent selected from the group consisting of: —CH$_2$OH, —CH$_2$OMe, —CH$_2$NMe$_2$, —CH$_2$F, —CH$_2$OCH$_2$OMe;

CN; and

C(O)H.

Preferably, R$_3$ represents an alkyl group comprising from 1 to 20 carbon atoms, preferably from 1 to 5 carbon atoms, substituted with one of the following groups:

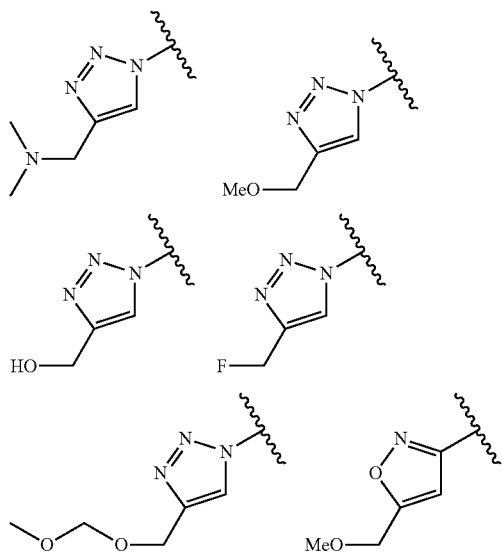

A class of compounds according to the invention consists of compounds of the following formula (I-4):

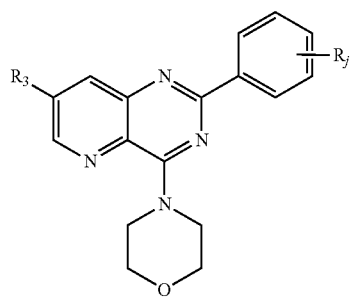

wherein R$_3$ and R$_j$ are as defined above.

Another class of compounds according to the invention consists of compounds with the following formula (I-4-A):

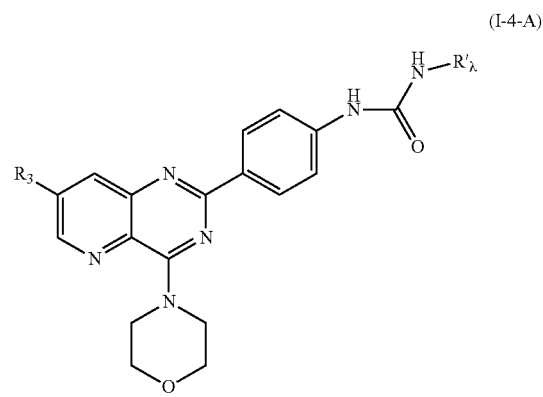

(I-4-A)

wherein R'$_\lambda$ is such as defined earlier.

According to an embodiment, R$_3$ represents an alkyl group comprising from 1 to 20 carbon atoms, said alkyl group being optionally substituted with at least one substituent selected from the group consisting of:

OR$_f$, R$_f$ being as defined earlier,

NHR$_g$, R$_g$ being as defined earlier,

NR$_h$R$_i$, with R$_h$ and R$_j$ being as defined earlier, a halogen, such as F, Cl, Br or I;

a group C(O)H,

—N$_3$,

—CN, and a (hetero)aryl group comprising from 5 to 30 atoms, such as an isoxazole or a triazole, said (hetero)aryl group being optionally substituted with at least one substituent selected from the group consisting of: —CH$_2$OH, —CH$_2$OMe, —CH$_2$NMe$_2$, —CH$_2$F, —CH$_2$OCH$_2$OMe.

Preferably, R$_3$ represents an alkyl group comprising from 1 to 20 carbon atoms, preferably from 1 to 5 carbon atoms, said alkyl group being substituted with at least one substituent selected from the group consisting of:

OH;

NH-cyclopropyl;

NH-cyclohexyl;

N-morpholine;

N-piperazine, optionally substituted with at least one substituent selected from the group consisting of methyl, —SO$_2$Me, cyclohexyl, phenyl;

OMe;

N$_3$;

heteroaryl, and notably 1,2,3-triazole or isoxazole, substituted with at least one substituent selected from the group consisting of: —CH$_2$OH, —CH$_2$OMe, —CH$_2$NMe$_2$, —CH$_2$F, —CH$_2$OCH$_2$OMe;

CN; and

C(O)H.

According to an embodiment, R'$_\lambda$ represents an aryl group, and preferably a phenyl, optionally substituted.

Thus the present invention relates to the following particular compounds:

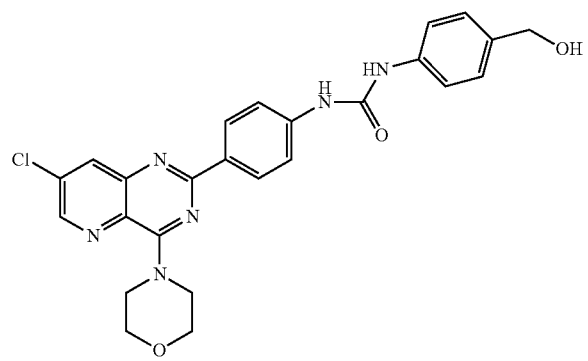

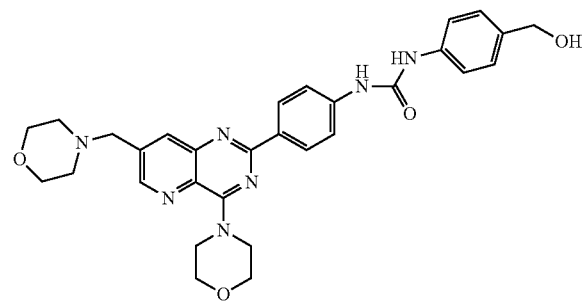

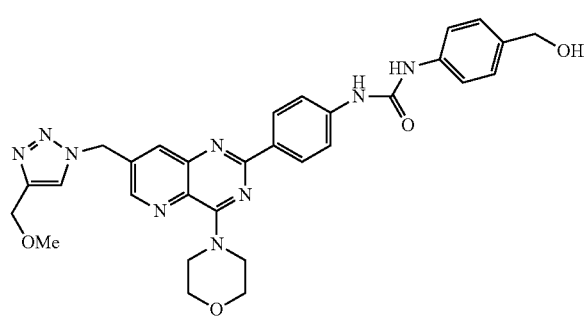

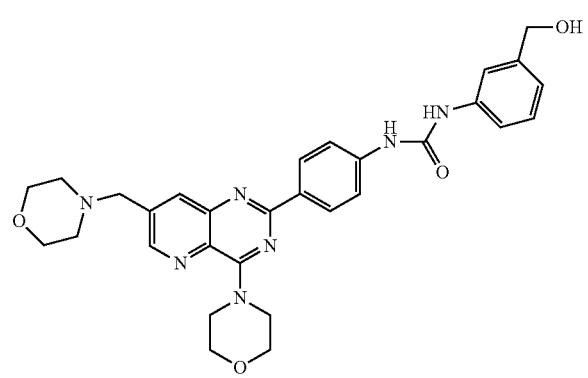

According to an embodiment, R'$_\lambda$ represents an alkyl group comprising from 1 to 20 carbon atoms, optionally substituted.

Thus, the present invention relates to the following particular compounds:

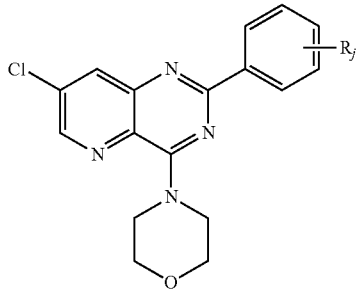

According to an embodiment, in the compounds of formulae (I-4) and (I-4-A), R$_3$ represents a halogen atom selected from F, Cl and I, and preferably a chlorine atom.

Among the compounds of formula (I-4), mention may notably be made of the compounds of the following formula (I-4-a):

(I-4-a)

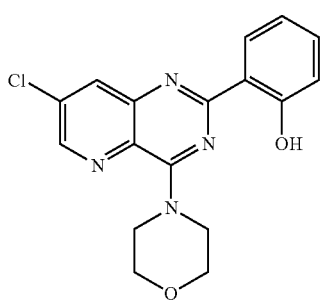

wherein R$_j$ is as defined earlier.

Thus, the present invention relates to the following particular compounds:

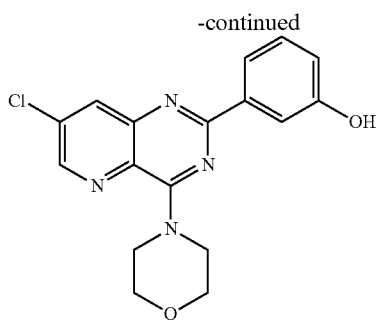

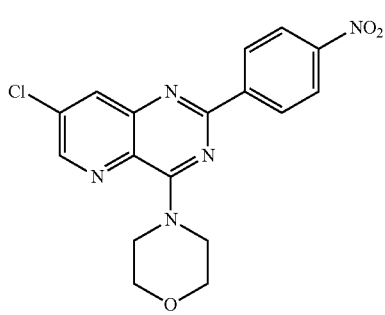 [SMILES: Nc1ccc(-c2nc(N3CCOCC3)c3ncc(Cl)cc3n2)cc1]

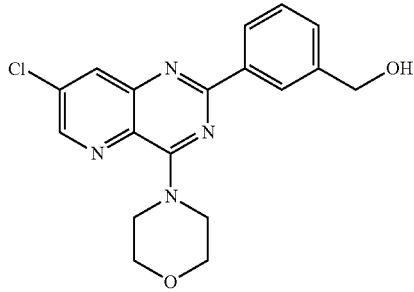

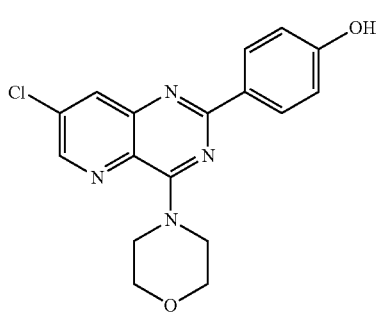

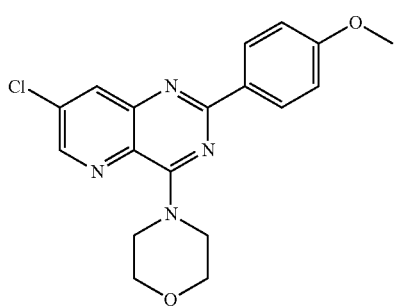

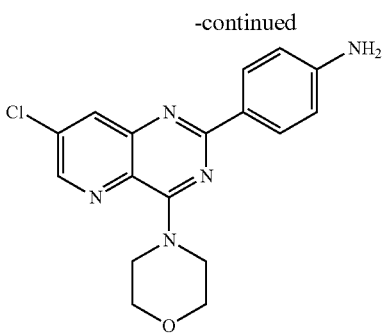

According to an embodiment, in the compounds of formula (I-4), $R_3$ represents an alkenyl group comprising from 1 to 20 carbon atoms, optionally substituted. Preferably, $R_3$ represents a non-substituted alkenyl group comprising from 1 to 5 carbon atoms, and preferentially 2 carbon atoms.

Among the compounds of formula (I-4), mention may notably be made of the compounds of the following formula (I-4-b):

(I-4-b)

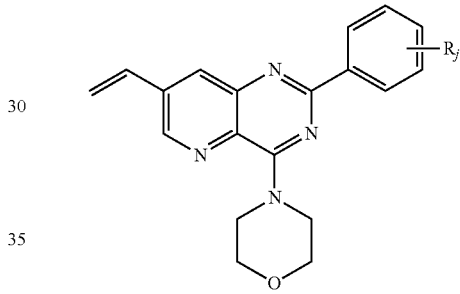

wherein $R_j$ is as defined earlier.

Thus, the present invention relates to the following particular compounds:

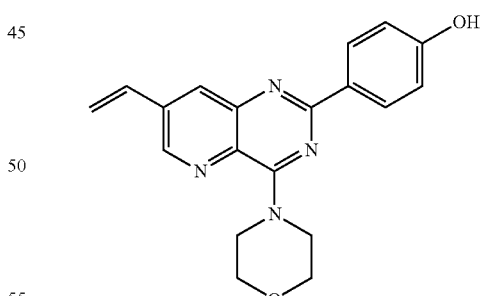

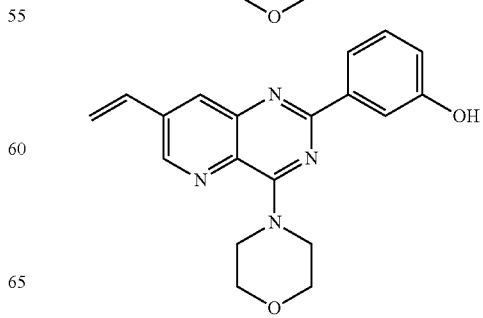

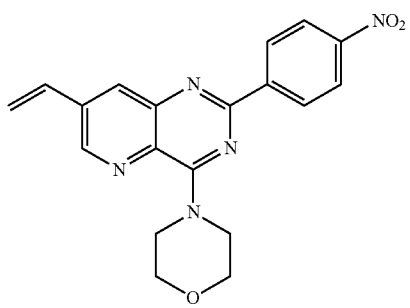

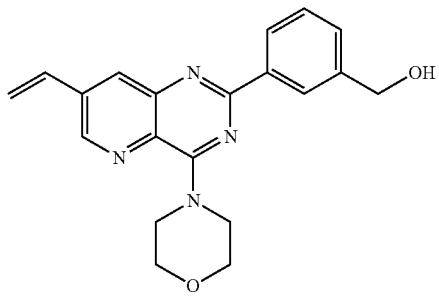

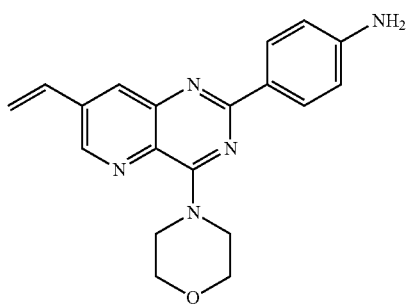

A family of compounds according to the invention consists of compounds of formula (I-4) wherein $R_3$ represents a group —C(O)$R_c$, $R_c$ being as defined above. Preferably, $R_c$ represents a hydrogen atom.

From among the compounds of formula (I-4), mention may notably be made of the compounds of the following formula (I-4-c):

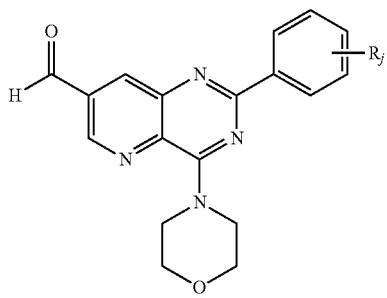

(I-4-c)

wherein $R_j$ is as defined earlier.

Thus, the present invention relates to the following particular compound:

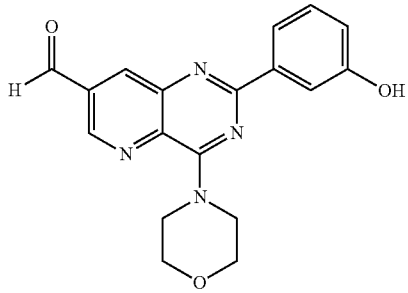 [SMILES: O=Cc1cnc2c(N3CCOCC3)nc(-c3cccc(O)c3)nc2c1]

Another family of compounds according to the invention consists of compounds of formula (I-4) wherein $R_3$ represents a group —C(O)O$R'_c$, $R'_c$ being as defined earlier. Preferably, $R'_c$ represents a hydrogen atom.

From among the compounds of formula (I-4), mention may notably be made of the compounds of the following formula (I-4-d):

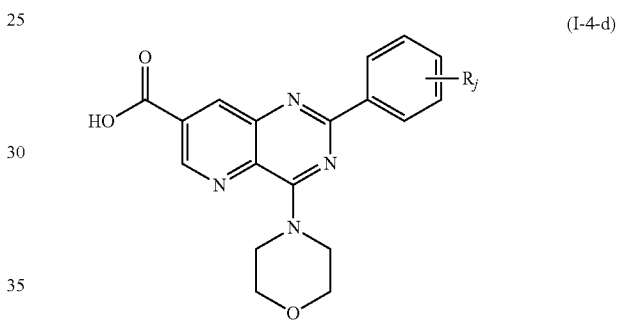

(I-4-d)

wherein $R_j$ is as defined earlier.

Thus, the present invention relates to the following particular compound:

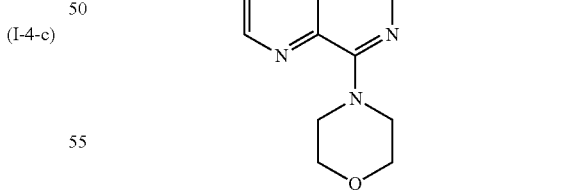

Another family of compounds according to the invention consists of compounds of formula (I-4) wherein $R_3$ represents a group —C($R_e$)=N—(O$R_d$), $R_d$ and $R_e$ being as defined above. Preferably, $R_d$ represents a hydrogen atom or a methyl group.

From among the compounds of formula (I-4), mention may notably be made of the compounds of the following formula (I-4-e):

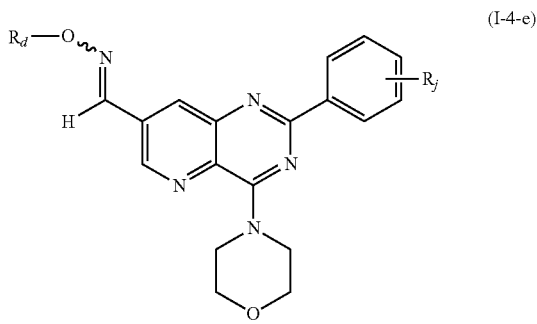
(I-4-e)

wherein $R_d$ and $R_j$ are as defined earlier.

Thus, the present invention relates to the following particular compounds:

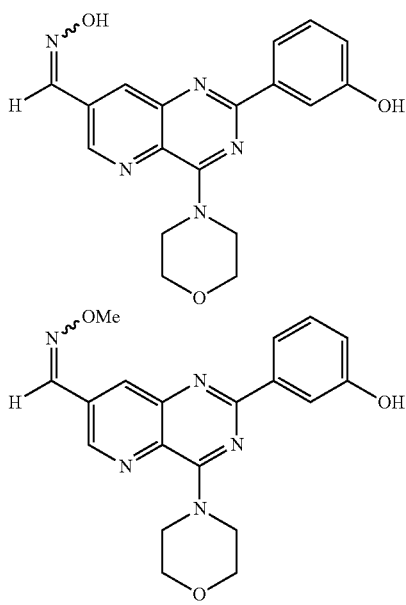

Another family of compounds according to the invention consists of compounds of formula (I-4) wherein $R_3$ represents an alkyl group comprising from 1 to 20 carbon atoms, said alkyl group being optionally substituted with at least one substituent selected from the group consisting of:

$OR_f$, $R_f$ being as defined above,
$NHR_g$, $R_g$ being as defined above,
$NR_hR_i$, with $R_h$ and $R_i$ being as defined above,
a halogen,
—$N_3$,
—CN,
a (hetero)aryl group comprising from 5 to 30 atoms, said (hetero)aryl group being optionally substituted.

According to an embodiment, from among the compounds of formula (I-4), mention may be made of the compounds for which $R_3$ represents an alkyl group comprising from 1 to 20 carbon atoms, being substituted with at least one group $OR_f$. Preferably, $R_3$ is an ethyl group substituted with two hydroxyl groups. Preferably, $R_3$ is an ethyl group substituted with two —O-methyl groups.

From among the compounds of formula (I-4), mention may notably be made of the compounds of the following formula (I-4-f):

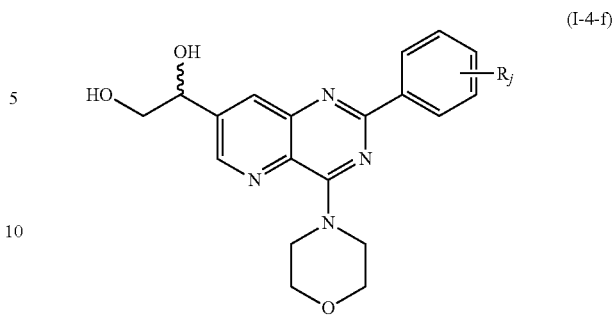
(I-4-f)

wherein $R_j$ is as defined earlier.

Thus, the present invention relates to the following particular compounds:

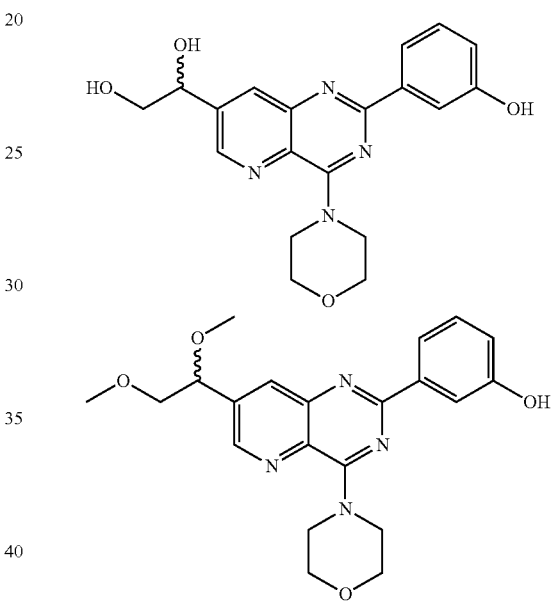

Within the scope of the invention, and unless indicated otherwise, the sign ⁓ corresponds to a bond found in front or behind the plane of the molecule.

From among the compounds of formula (I-4), mention may notably be made of the compounds of the following formula (I-4-f'):

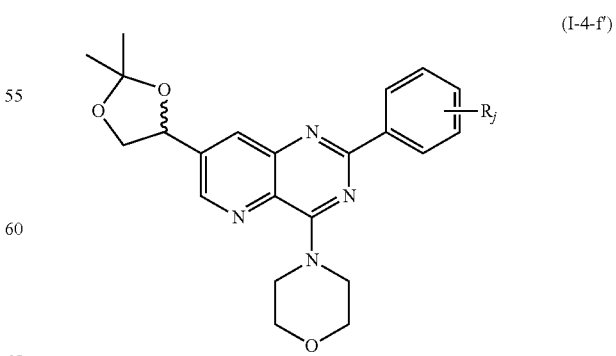
(I-4-f')

wherein $R_j$ is as defined earlier.

Thus, the present invention relates to the following particular compound:

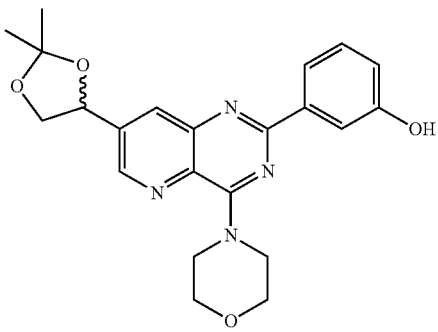 [SMILES: CC1(C)OCC(c2cnc3c(N4CCOCC4)nc(-c4cccc(O)c4)nc3c2)O1]

Within the scope of the invention, and unless indicated otherwise, the sign ⌇ corresponds to a bond found in front or behind the plane of the molecule.

From among the compounds of formula (I-4), mention may notably be made of the compounds of the following formula (I-4-1):

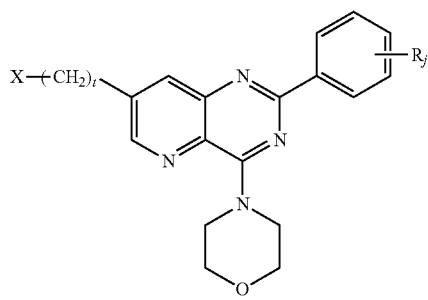

(I-4-1)

wherein:
$R_j$ is as defined earlier;
t represents an integer comprised from 1 to 12, preferably from 1 to 5;
X is selected from the group consisting of:
$OR_f$, $R_f$ being as defined above;
CN;
$N_3$;
a halogen, notably an iodine atom;
$NR_hR_i$, $R_h$ and $R_i$ being as defined above;
$NHR_g$, $R_g$ being as defined above;
C(O)H;
a (hetero)aryl group comprising from 5 to 30 atoms, said (hetero)aryl being optionally substituted with at least one substituent which may represent —$(CH_2)_uR''$, u representing an integer selected from 1 to 5, and R" representing a group selected from:
a halogen atom, notably F,
a group —$OCH_2OMe$,
an alkyl group comprising from 1 to 10 carbon atoms,
a group —$NR_4R_5$, $R_4$ and $R_5$ being independently selected from an alkyl group comprising from 1 to 10 carbon atoms or a hydrogen atom, such as $NMe_2$,
$OR_6$, $R_6$ representing a hydrogen atom or an alkyl group comprising from 1 to 10 carbon atoms, a group —C(O)H,
a group —$C(O)OR'_\alpha$, $R'_\alpha$ being as defined earlier,
a group —$OSO_2NHR''_\lambda$, $R''_\lambda$ being as defined earlier,
$NR_aR_b$, $R_a$ and $R_b$ being as defined earlier,
$NHCOOR'_\alpha$, $R'_\alpha$ being as defined earlier.
In particular, u represents 1.

From among the compounds according to the invention, mention may be made of the compounds of formula (I-4-1) for which X represents OH.

From among the compounds of formula (I-4), mention may notably be made of the compounds of the following formula (I-4-1-a):

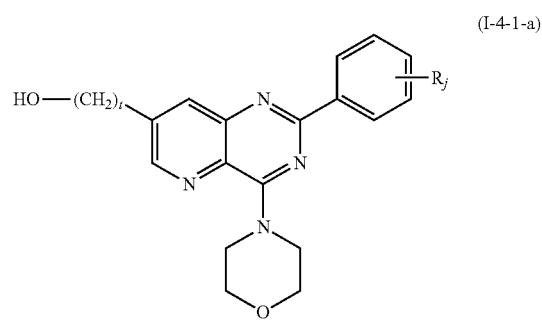

(I-4-1-a)

wherein $R_j$ and t are as defined earlier.

Thus, the present invention relates to the following particular compound:

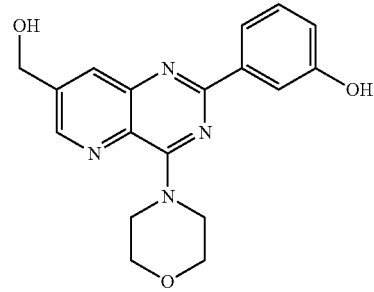

From among the compounds according to the invention, mention may be made of the compounds of formula (I-4-1) for which X represents OMe.

From among the compounds of formula (I-4), mention may notably be made of the compounds of the following formula (I-4-1-b):

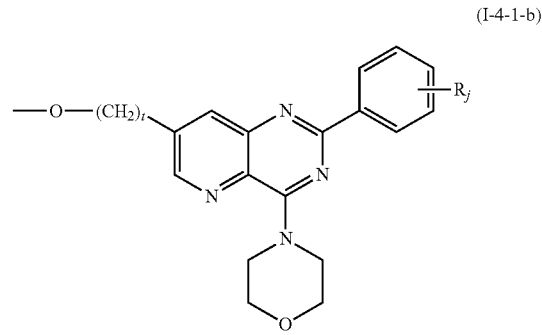

(I-4-1-b)

wherein $R_j$ and t are as defined earlier.

Thus, from among the compounds according to the invention, mention may be made of the following particular compound:

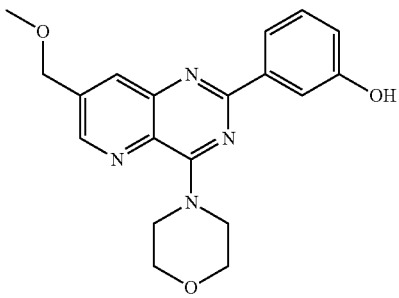 [SMILES: COCc1cnc2c(N3CCOCC3)nc(-c3cccc(O)c3)nc2c1]

From among the compounds according to the invention, mention may be made of the compounds of formula (I-4-1) for which X represents a halogen, and notably an iodine atom.

From among the compounds of formula (I-4), mention may notably be made of the compounds of the following formula (I-4-1-c):

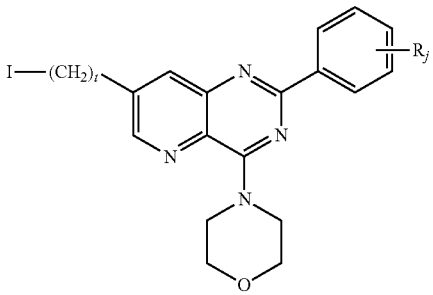

(I-4-1-c)

wherein $R_j$ and t are as defined earlier.

Thus, the present invention relates to the following particular compound:

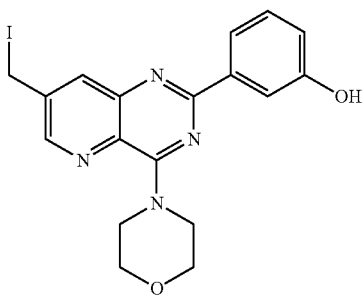 [SMILES: Oc1cccc(-c2nc(N3CCOCC3)c3ncc(CI)cc3n2)c1]

From among the compounds according to the invention, mention may be made of the compounds of formula (I-4-1) for which X represents $N_3$.

From among the compounds of formula (I-4), mention may notably be made of the compounds of the following formula (I-4-1-d):

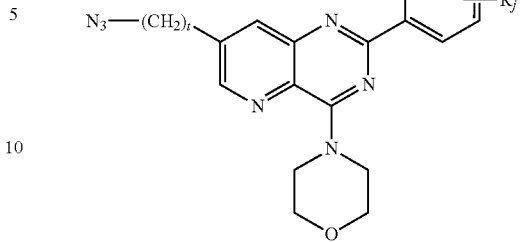

(I-4-1-d)

wherein $R_j$ and t are as defined earlier.

Thus, the present invention relates to the following particular compound:

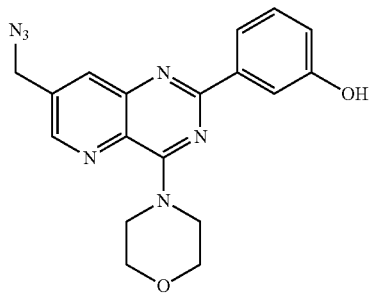 [SMILES: [N-]=[N+]=NCc1cnc2c(N3CCOCC3)nc(-c3cccc(O)c3)nc2c1]

From among the compounds according to the invention, mention may be made of the compounds of formula (I-4-1) for which X represents CN.

From among the compounds of formula (I-4), mention may notably be made of the compounds of the following formula (I-4-1-d):

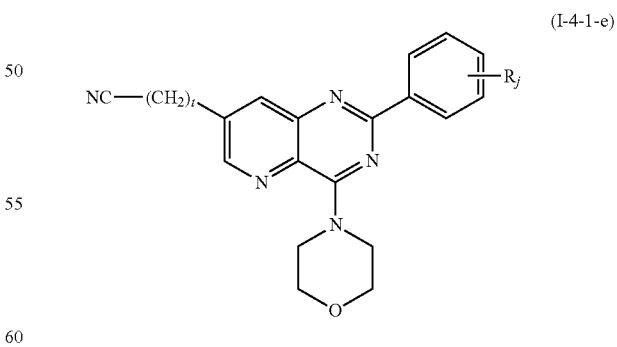

(I-4-1-e)

wherein $R_j$ and t are as defined earlier.

Thus, the present invention relates to the following particular compound:

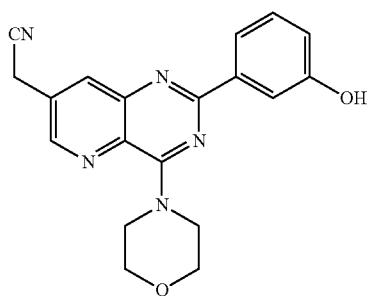

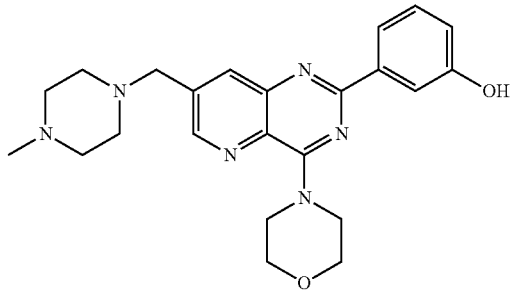

From among the compounds according to the invention, mention may be made of the compounds of formula (I-4-1) for which X represents:

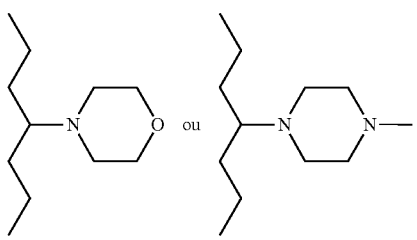

From among the compounds of formula (I-4), mention may notably be made of the compounds of the following formula (I-4-1-f):

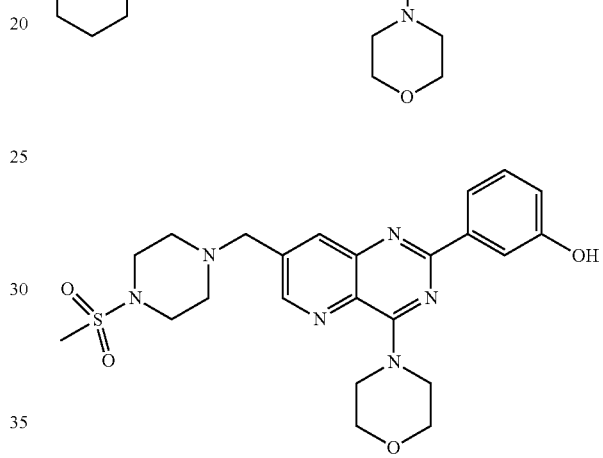

(I-4-1-f)

wherein $R_j$ and t are as defined earlier and Z represents —O—, —S—, —S(O$_2$)—, —C(F$_2$)—, —CH(CH$_2$OH), —NMe-, —N(SO$_2$Me), —N(cyclohexyl), —N(phenyl), —CH(CH$_3$)—, —N[C(O)R'$_\alpha$], R'$_\alpha$ being as defined earlier, or —N[S(O)$_2$NHR'$_\lambda$]—, R'$_\lambda$ being as defined earlier.

Preferably, $R_j$ represents —OH.

Preferably, Z represents O—, —N(SO$_2$Me), —N(cyclohexyl), —N(phenyl) or —N(Me).

Thus, the present invention relates to the following particular compounds:

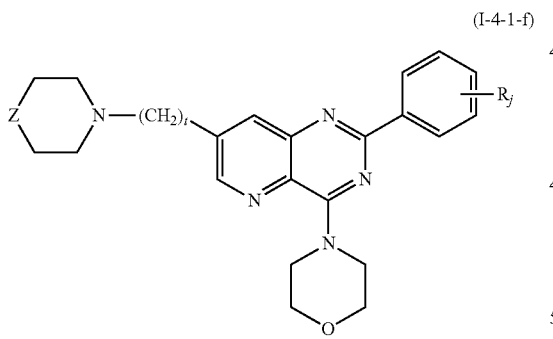

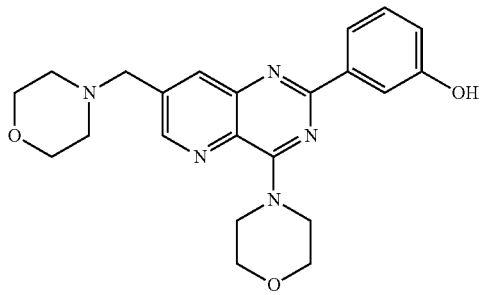

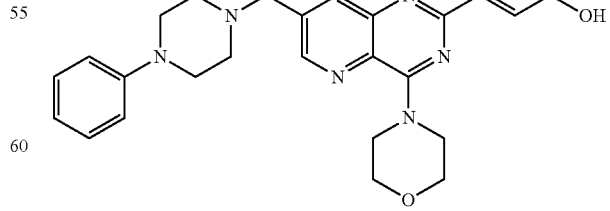

From among the compounds according to the invention, mention may be made of the compounds of formula (I-4-1) for which X represents a group selected from:

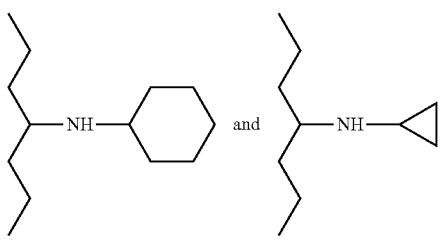 and

From among the compounds of formula (I-4), mention may notably be made of the compounds of the following formula (I-4-1-g):

(I-4-1-g)

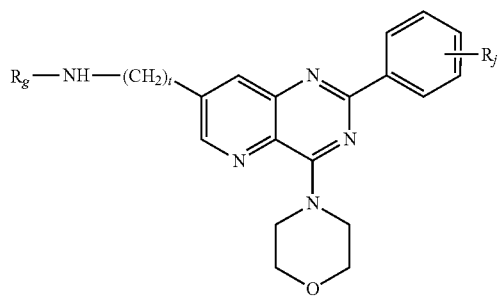

wherein $R_g$, $R_j$ and t are as defined earlier.

Thus, the present invention relates to the following particular compounds:

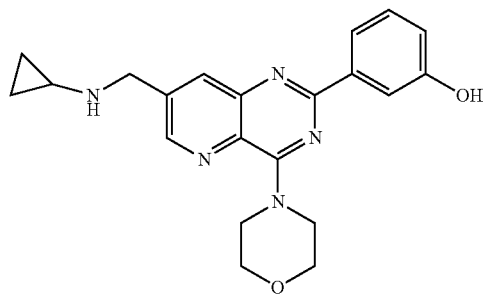

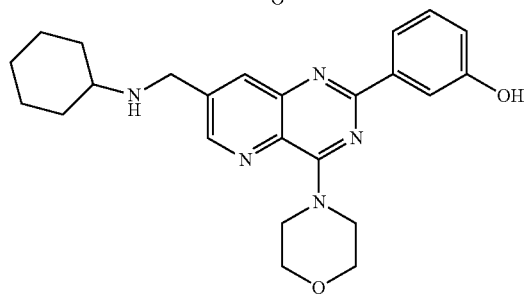

From among the compounds according to the invention, mention may be made of the compounds of formula (I-4-1) for which X represents —C(O)H.

From among the compounds of formula (I-4), mention may notably be made of the compounds of the following formula (I-4-1-h):

(I-4-1-h)

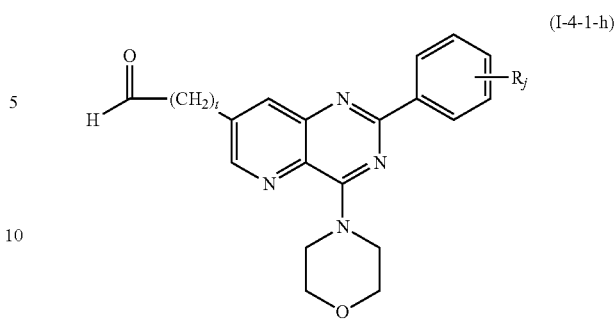

wherein $R_j$ and t are as defined earlier.

Thus, the present invention relates to the following particular compound:

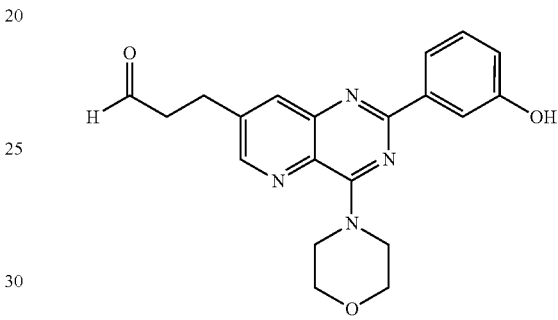

From among the compounds according to the invention, mention may also be made of the compounds of formula (I-4-1) for which X represents a heteroaryl group comprising from 5 to 30 atoms, preferably from 5 to 10 atoms, selected from the group consisting of:

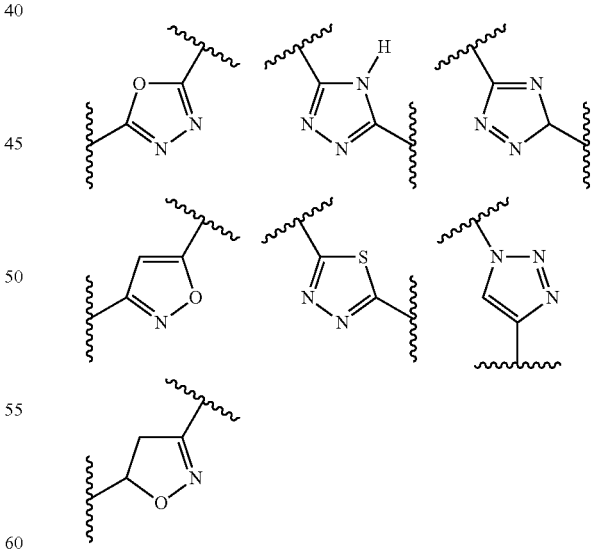

and said heteroaryl being preferably substituted with a group —(CH$_2$)$_u$R", u and R" being as defined earlier.

From among the compounds of formula (I-4), mention may notably be made of the compounds of the following formula (I-4-1-i):

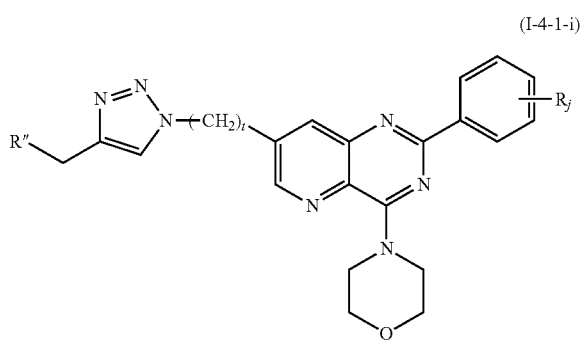

wherein R", $R_j$ and t are as defined earlier.

Thus, the present invention relates to the following particular compounds:

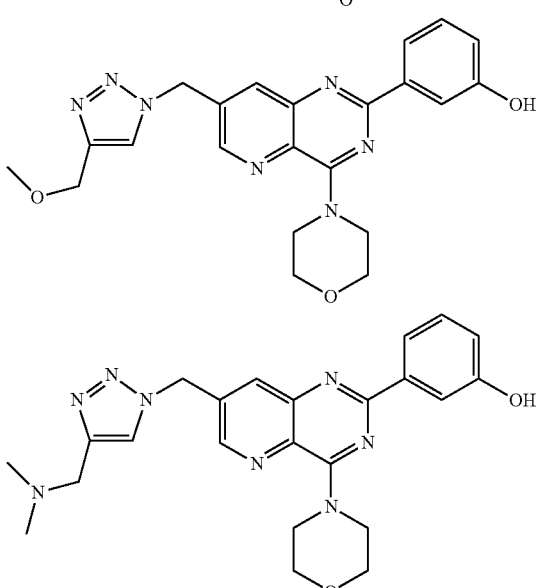

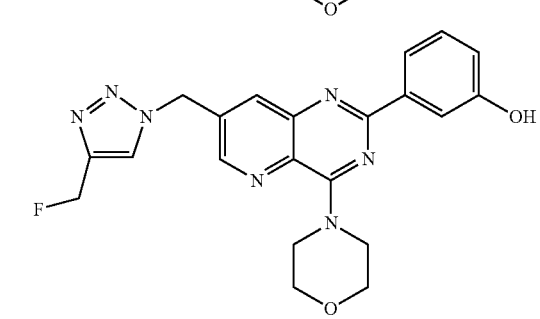

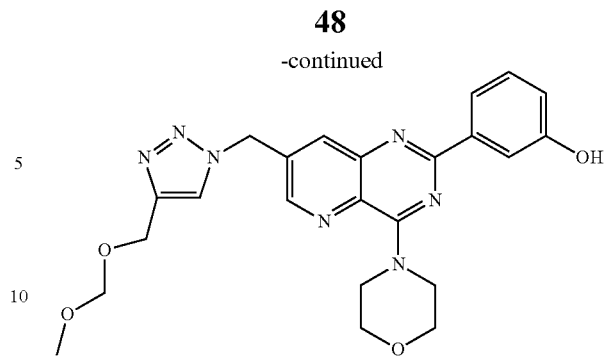

From among the compounds of formula (I-4), mention may notably be made of the compounds of the following formula (I-4-1-j):

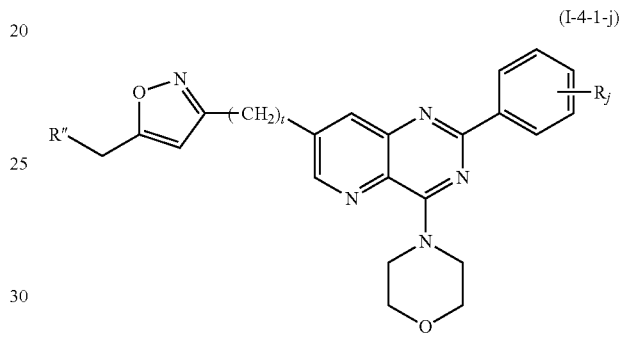

wherein R", $R_j$ and t are as defined earlier.

Thus, the present invention relates to the following particular compound:

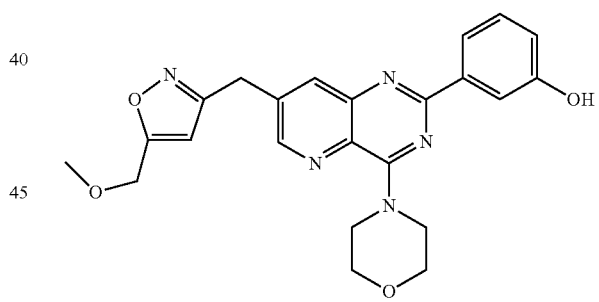

Another class of compounds according to the invention consists of compounds of the following formula (I-5):

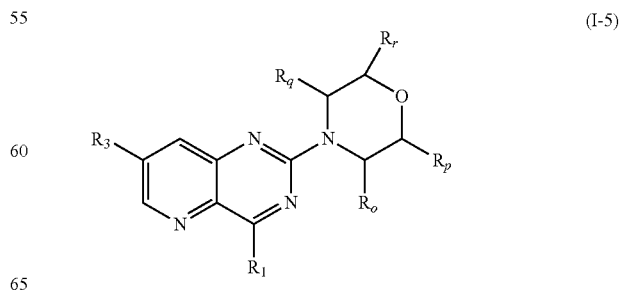

$R_1$, $R_3$, $R_o$, $R_p$, $R_q$ and $R_r$ being as defined above.

From among the compounds of formula (I-5), the present invention relates to the compounds of the following formula (I-5-a):

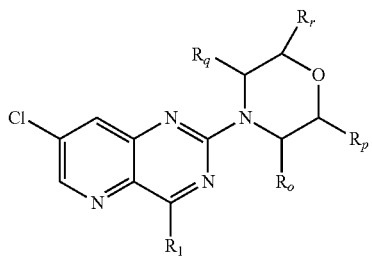

(I-5-a)

$R_1$, $R_3$, $R_o$, $R_p$, $R_q$ and $R_r$ being as defined above.

From among the compounds of formula (I-5), the present invention relates to the compounds of the following formula (I-5-1):

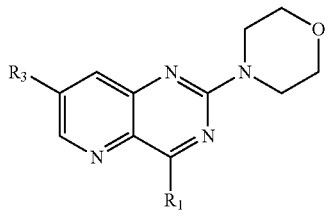

(I-5-1)

wherein, $R_1$ and $R_3$ are as defined above.

The compounds of formula (I-5-1) according to the invention, correspond to the compounds of formula (I-5) wherein $R_o$, $R_p$, $R_q$ and $R_r$ represent a hydrogen atom.

According to an embodiment, in the compounds of formulae (I-5) and (I-5-1), $R_1$ represents a heteroaryl group comprising from 5 to 30 atoms, said heteroaryl group being optionally substituted.

Preferably, in the compounds of formulae (I-5) and (I-5-1), $R_1$ represents a heteroaryl group selected from:

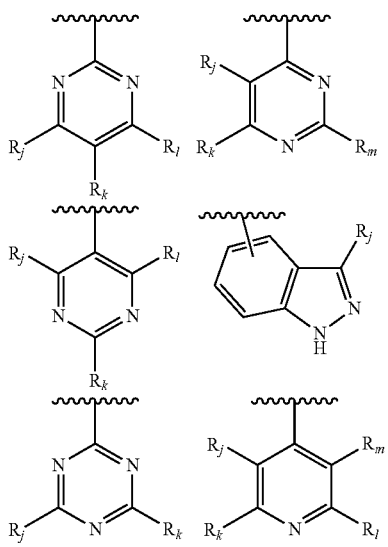

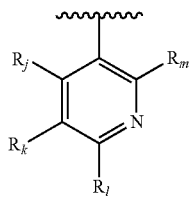

$R_j$, $R_k$, $R_l$ and $R_j$ being as defined above.

According to another embodiment, in the compounds of formulae (I-5) and (I-5-1), $R_1$ represents an aryl group comprising from 5 to 30 carbon atoms, said aryl group being optionally substituted.

Preferably, the aryl group is the following group:

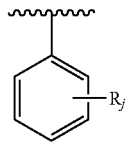

Rj being as defined above, and preferably selected from: H, $OCH_2OCH_3$, OH, OMe, $CH_2OH$, $NO_2$, $NH_2$ and $NH-C(O)NHR'_\lambda$, $R'_\lambda$ being as defined above. In particular, $R'_\lambda$ represents an alkyl, aryl or heteroaryl group, said alkyl, aryl or heteroaryl being optionally substituted with at least one substituent selected from a group $-NH_2$, $-OH$, alkoxy, $-O-(CH_2)_xOCH_3$, x being an integer comprised from 1 to 10, and $-COOH$.

A class of compounds according to the invention consists of compounds of the following formula (I-6):

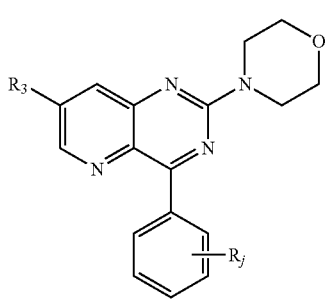

(I-6)

wherein $R_3$ and $R_j$ are as defined above.

According to an embodiment, the present invention relates to the compounds of formula (I-6), wherein $R_3$ represents a halogen, and notably a chlorine atom.

Thus, the present invention relates to the following particular compound:

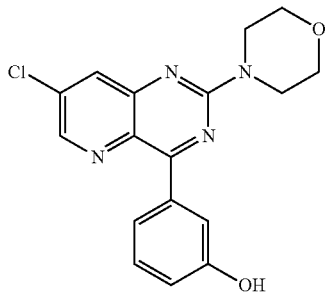 [SMILES: Oc1cccc(-c2nc(N3CCOCC3)nc3cc(Cl)cnc23)c1]

The present invention also relates to a pharmaceutical composition comprising a compound of formula (I) as defined above or one of its pharmaceutically acceptable salts, or any compound as mentioned above, associated with a pharmaceutically acceptable carrier.

The present invention therefore relates to a compound as defined above of formula (I) for its use as a drug.

The pharmaceutical compositions according to the invention may appear in forms intended for administration via a parenteral, oral, rectal, permucosal or percutaneous route.

The pharmaceutical compositions including these compounds of general formula (I) will therefore appear as solutes or injectable suspensions or multi-dose flasks, as naked or coated tablets, dragees, capsules, gelatin capsules, pills, wafers, powders, suppositories or rectal capsules, solutions or suspensions, for percutaneous use in a polar solvent, for permucosal use.

The excipients which are suitable for such administrations are derivatives of cellulose or of microcrystalline cellulose, earth-alkaline carbonates, magnesium phosphate, starches, modified starches, lactose for solid forms.

For rectal use, cocoa butter or polyethylene glycol stearates are the preferred excipients.

For parenteral use, water, aqueous solutes, saline, isotonic solutes are the carriers which are used the most conveniently.

The dosage may vary within large limits (0.5 mg to 1,000 mg) depending on the therapeutic indication and on the administration route, as well as on the age and weight of the subject.

The present invention also relates to a compound as defined above of formula (I), or any compound as mentioned above, for its use as an inhibitor of PI3K and/or mTOR enzymes.

The present invention also relates to a compound as defined above of formula (I), or any compound as mentioned above, for its use within the scope of treating or preventing diseases related to deregulation of PI3K and/or mTOR enzymes.

More particularly, said diseases (pathologies) are selected from the group consisting of cancers, such as cancers of the lungs, of the kidneys, of the ovaries, of the pancreas, of the skin, of the colon, of the prostate, leukemias, non-degenerative diseases, such as arthritis, inflammation, sclerosis, glomerular nephrites, psoriasis, allergies, asthma, diabetes, thrombo-embolic diseases and auto-immune diseases.

The present invention also relates to the use of a compound of the invention as defined above, for preparing a drug intended for treating or preventing diseases related to deregulation of the PI3K and/or mTOR enzymes, and more particularly for treating and preventing the aforementioned diseases.

The present invention also relates to a method for treating the aforementioned pathologies comprising administration to a patient of a pharmaceutically acceptable dose of a compound of formula (I) as defined earlier.

The present invention also relates to a method for preparing a compound of the following formula (I-1):

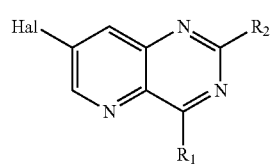

(I-1)

$R_1$, $R_2$, $R_o$, $R_p$, $R_q$ and $R_r$ being as defined above, said method comprising the following steps:
a) a step for aromatic nucleophilic substitution (regioselective in position 4) of the following compound (3):

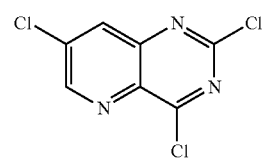

(3)

in the presence of the following compound (3a):

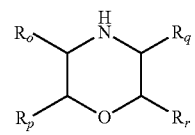

(3a)

$R_o$, $R_p$, $R_q$ and $R_r$ being as defined above, and of a base, in order to obtain the intermediate compound of formula (I-2-1), as defined earlier; and b) a Suzuki coupling step (regioselective in position 2) of the compound of the aforementioned formula (I-2-1), in the presence of the compound $R_2B(OH)_2$, $R_2$ being as defined above, in order to obtain the compound of the aforementioned formula (I-1), wherein Hal represents a chlorine.

Preferably, the aforementioned step a) is carried out in the presence of $Et_3N$. It is also carried out in a solvent such as THF at room temperature for 12 hours.

Preferably, the aforementioned step b) is carried out in the presence of $K_2CO_3$. It is also carried out in the presence of a catalyst such as $Pd(PPh_3)_4$, in a solvent such as dimethylether (DME), at 150° C. In particular, the reaction is conducted under microwave activation for one hour.

The present invention also relates to a method for preparing a compound of formula (I-5) as defined earlier, said method comprising the following steps:
a) a Suzuki coupling step (regioselective in position 4) for the compound (3) as defined above, in the presence of the $R_1BF_3K$ compound, wherein $R_1$ represents a (hetero)aryl group comprising from 5 to 30 atoms, in order to obtain the intermediate compound of the following formula (X):

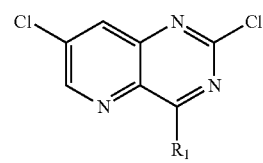

(X)

wherein $R_1$ represents a (hetero)aryl group optionally substituted as defined above, and
b) a step for palladium coupling of the Suzuki-Myaura type the aforementioned compound of formula (X), with a compound of formula (3a) as defined above, in order to lead to a compound of formula (I-5-a) as defined earlier, in order to lead to a compound of the aforementioned formula (I-5).

In an embodiment, the method for preparing a compound of the aforementioned formula (I-5) comprises a deprotection step c), when $R_1$ representing a substituted (hetero)aryl group comprises a hydroxyl substituent provided with a protective group, such as MOM (methoxymethylether).

Step a) is preferably carried out in the presence of a catalyst $Pd(PPh_3)_4$, in a solvent such as toluene, at 100° C. for about two hours. In particular, the reaction is conducted in the presence of $K_2CO_3$.

Step b) is preferably carried out in the presence of a catalyst $Pd(OAc)_2$, and of the ligand Xantphos, in a solvent such as dioxane. In particular, the reaction is conducted at 170° C. for about one hour.

The optional step c) is preferably conducted in the presence of a strong acid, notably hydrochloric acid, in a solvent such as dioxane. In particular, step c) is carried out at room temperature.

The present invention also relates to a method for preparing a compound of formula (I-4-b) as defined above, said method comprising a step a) for Suzuki coupling of a compound of formula (I-4-a) as defined earlier, with a compound of formula ($X_1$):

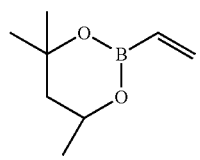

in order to lead to a compound of formula (I-4-b).

Step a) is preferably carried out in the presence of a catalyst $Pd(PPh_3)_4$, and of $K_2CO$, in a solvent such as the toluene/ethanol (3/1) mixture. In particular, the reaction is carried out at 150° C., for about one hour, with microwave activation.

According to an embodiment, the method for preparing a compound of the aforementioned formula (I-4-b) comprises a step a') for protecting a hydroxyl or amino function with a protective group such as MOM (methoxymethylether), when $R_j$ represents —OH or —$NH_2$. In particular, step a') is carried out in the presence of MOMCl (methoxymethylether chloride), and of a base $K_2CO_3$, Preferably, the protective reaction is conducted in a solvent, such as acetone, at room temperature for about 12 hours.

According to an embodiment, the method for preparing a compound of the aforementioned formula (I-4-b) comprises a step a") for deprotecting the protected hydroxyl or amino function during step a'). Step a") is preferably carried out in the presence of a strong acid, notably hydrochloric acid, in a solvent such as dioxane. In particular, step a") is carried out at room temperature.

The present invention also relates to a method for preparing a compound of formula (I-4-c) as defined above, said method comprising a step for oxidizing a compound of formula (I-4-b) as defined above, in the presence of $OsO_4$.

Preferably, step a) is carried out in the presence of $NaIO_4$, in a solvent such as the THF/$H_2O$ (1/1) mixture, at room temperature, for about 3 hours.

The method for preparing the compound of formula (I-4-c) may comprise a deprotection step b), when the group $R_j$ in the compound (I-4-b) corresponds to a protected hydroxy group, notably protected by a —$CH_2OCH_3$ group (-MOM). In particular, the deprotection step b) is carried out in the presence of a strong acid, notably hydrochloric acid, in a solvent such as dioxane. In particular, step c) is carried out at room temperature.

The present invention also relates to a method for preparing a compound of formula (I-4-d) as defined above, said method comprising a step a) for oxidizing a compound of formula (I-4-c), wherein $R_j$ may represent a hydroxy group optionally protected with a protective group, in the presence of an oxidizer.

Preferably, step a) is carried out in the presence of $NaH_2PO_4$ and $NaClO_2$, and of t-BuOH, of water and 2-methylbutene. In particular, step a) is carried out at room temperature, for about 3 hours.

The present invention also relates to a method for preparing a compound of formula (I-4-e) as defined above, said method comprising a step for amination of a compound of formula (I-4-c) as defined earlier in the presence of a compound $R_dO$—$NH_2$.

Preferably, the amination step is carried out in the presence of $Et_3N$, in a solvent such as dichloromethane with reflux, for about 12 hours.

The present invention also relates to a method for preparing a compound of formula (I-4-f) as defined above, said method comprises a step for oxidizing a compound of formula (I-4-b) as defined above, in the presence of $OsO_4$.

Preferably, step a) is carried out in the presence of NMO, in a solvent such as the acetone/$H_2O$ (1/1) mixture, at room temperature for about 3 hours.

The method for preparing a compound of formula (I-4-d) may optionally comprise a deprotection step b), when the group $R_j$ in the compound (I-4-b) corresponds to a protective hydroxy group, notably by a —$CH_2OCH_3$ group. In particular, the deprotection step b) is in the presence of a strong acid, notably hydrochloric acid, in a solvent such as dioxane. In particular, step c) is carried out at room temperature.

The present invention also relates to a method for preparing a compound of formula (I-4-1-a) as defined above, said method comprising a step for reducing a compound of the aforementioned formula (I-4-c).

Preferably, the reduction step is carried out in the presence of $NaBH_4$, in a solvent such as methanol, at room temperature, for about two hours.

The method for preparing a compound of formula (I-4-1-a) may comprise a deprotection step b), when the group $R_j$ in the compound (I-4-c) corresponds to a hydroxy group notably protected by a —$CH_2OCH_3$ group (-MOM). In particular, the deprotection step b) is carried out in the presence of a strong acid, notably hydrochloric acid, in a solvent such as dioxane.

The present invention also relates to a method for preparing a compound of formula (I-4-1-b) as defined above, said method comprising the following steps:
 a step a) for alkylation of a compound of the aforementioned formula (I-4-1-a), and
 an optional deprotection step b), when the group $R_j$ in the compound (I-4-1-a) corresponds to a hydroxy group notably protected by a group —$CH_2OCH_3$ (-MOM).

In particular, the deprotection step b) is carried out in the presence of a strong acid, notably hydrochloric acid, in a solvent such as dioxane.

Preferably, step a) is carried out in the presence of NaH and of an alkylating agent such as MeI, in a solvent such as methanol, at room temperature, for about two hours.

The present invention also relates to a method for preparing a compound of the aforementioned formula (I-4-1-c), said method comprising a step for substitution of a compound of the aforementioned formula (I-4-1-a).

Preferably, the substitution step is carried out in the presence of PPh₃, of I₂ and imidazole, in a solvent such as dichloromethane, at 0° C., for about seven hours.

The present invention also relates to a method for preparing a compound of formula (I-4-1-d) as defined above, said method comprising a step for substitution of a compound of the aforementioned formula (I-4-1-a), notably in the presence of NaN₃.

Preferably, the reaction is conducted in a solvent such as DMF, at a temperature of 65° C., for about six hours.

The method for preparing compounds of formula (I-4-1-d) may comprise an optional deprotection step b), when the group $R_j$ in the compound (I-4-1-a) corresponds to a protected hydroxy group, notably with a group —CH₂OCH₃ (-MOM). In particular, the deprotection step b) is carried out in the presence of a strong acid, notably hydrochloric acid, in a solvent such as dioxane.

The present invention also relates to a method for preparing a compound of the aforementioned formula (I-4-1-e), said method comprising the reacting of a compound of the aforementioned formula (I-4-c), with TosMIC (p-toluene sulfonyl methyl isocyanate).

According to an embodiment, the reaction is carried out in the presence of t-BuOK, in a solvent such as DME (dimethylether), at −50° C. for about 40 minutes, and then in methanol with reflux for about one hour.

The method for preparing compounds of formula (I-4-1-e) may comprise an optional deprotection step b), when the group $R_j$ in the compound (I-4-c) corresponds to a hydroxy group notably protected by a group —CH₂OCH₃ (-MOM). In particular, the deprotection step b) is carried out in the presence of a strong acid, notably hydrochloric acid, in a solvent such as dioxane.

The present invention also relates to a method for preparing a compound of formula (I-4-1-f) as defined earlier, said method comprising a step for amination and reduction of a compound of the aforementioned formula (I-4-c), in the presence of morpholine when Z represents O or of N-piperazine, when Z represents NMe.

According to an embodiment, the amination step is carried out in the presence of NaB(OAc)₃, of acetic acid, in a solvent such as dichloromethane. Preferably, the reaction is carried out at room temperature for about six hours.

The method for preparing compounds of formula (I-4-1-f) may comprise an optional deprotection step b), when the group $R_j$ in the compound (I-4-c) corresponds to a hydroxy group notably protected by a group —CH₂OCH₃ (-MOM). In particular, the deprotection step b) is carried out in the presence of a strong acid, notably hydrochloric acid, in a solvent such as dioxane.

The present invention also relates to a method for preparing a compound of the aforementioned formula (I-4-1-g), said method comprising a step for amination and reduction of a compound of the aforementioned formula (I-4-c), in the presence of a compound $R_gNH_2$.

According to an embodiment, the amination step is carried out in the presence of NaBH₃CN, in a solvent such as dichloromethane. Preferably, the reaction is carried out at room temperature for about 12 hours.

The method for preparing compounds of formula (I-4-1-g) may comprise an optional deprotection step b), when the group $R_j$ in the compound (I-4-c) corresponds to a hydroxy group notably protected by a group —CH₂OCH₃ (-MOM). In particular, the deprotection step b) is carried out in the presence of a strong acid, notably hydrochloric acid.

The present invention also relates to a method for preparing a compound of the aforementioned formula (I-4-1-h), said method comprising a step a) for Suzuki coupling (in position 7 of the pyridopyrimidine ring) a compound of the aforementioned formula (I-4-a), in the presence of the following compound (W):

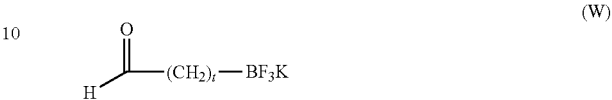

t being as defined earlier, in order to lead to a compound of the aforementioned formula (I-4-1-h).

According to an embodiment, step a) is carried out in the presence of the catalyst Pd(PPh₃)₄ and of the base K₂CO₃, in a solvent such as the toluene/ethanol mixture. Preferably, the reaction is carried out at 150° C., for about one hour, with microwave activation.

The method for preparing compounds of formula (I-4-1-h) may comprise an optional deprotection step b), when the group $R_j$ in the compound (I-4-a) corresponds to a hydroxy group notably protected by a group —CH₂OCH₃ (-MOM). In particular, the deprotection step b) is carried out in the presence of a strong acid, notably hydrochloric acid, in a solvent such as dioxane.

The present invention also relates to a method for preparing a compound of the aforementioned formula (I-4-1-i), said method comprising a [3,2]-cycloaddition step a) of the Huisgen type of a compound of the aforementioned formula (I-4-1-d), carried out in the presence of a compound (V) of the following formula:

According to an embodiment, step a) is carried out in the presence of CuI, in a solvent such as acetonitrile. Preferably, the reaction is carried out at room temperature for about 12 hours.

The present invention also relates to a method for preparing a compound of formula (I-4-A) as defined earlier, said method comprising a step for coupling in position 2 the intermediate compounds of formula (X₂):

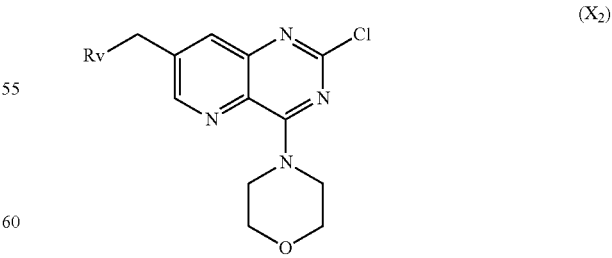

wherein Rv may represent an optionally substituted heteroaryl, as defined earlier, or a morpholine,
in the presence of boron-containing compounds of the following formula (X₃):

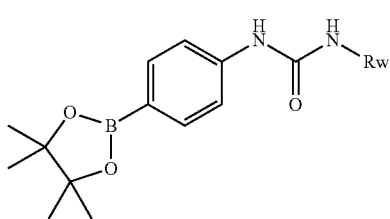

wherein Rw may represent one of the following groups:
—CH$_2$CF$_3$,

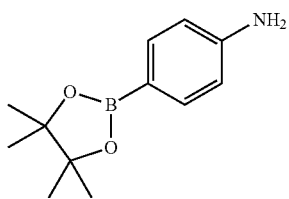

According to an embodiment, the coupling reaction is carried out in the presence of the catalyst Pd(PPh$_3$)$_4$ and of the base K$_3$PO$_4$, in a solvent such as acetonitrile. Preferably, the reaction is conducted at 120° C., for about one hour, with microwave activation.

According to an embodiment, the compounds of formula (X$_3$) may be obtained from the compound of formula (X$_4$):

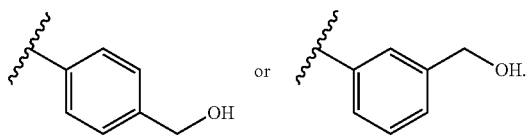 [SMILES: *c1ccc(CO)cc1 ; *c1cccc(CO)c1]

in the presence of an amine of formula Rw-NH$_2$.

According to an embodiment, the reaction is conducted in the presence of triphosgen and of triethylamine, in a solvent such as THF. In particular, the reaction is carried out for about 20 hours at room temperature.

According to an embodiment, the compounds of formula (X$_2$) may be obtained from compounds of formula (X$_5$):

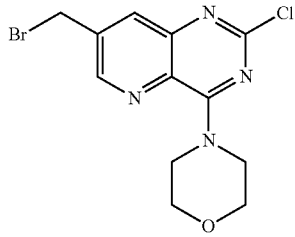

The following examples allow an illustration of the invention without however limiting it.

EXAMPLES

A. Preparation of the Compounds of the Invention

A.1. Preparation of the Synthesis Intermediate (3)

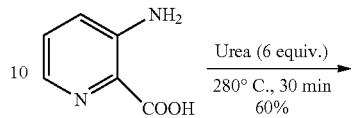

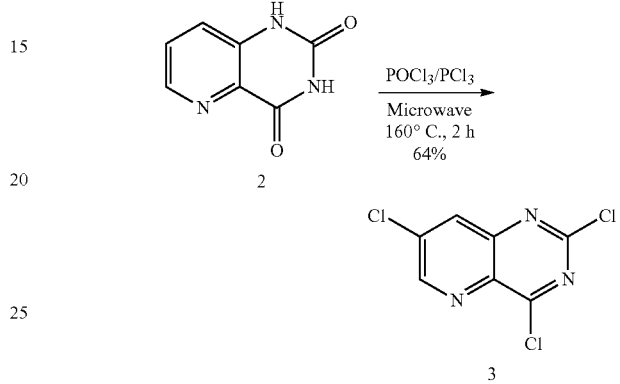

Compound (2) was synthesized according to the conditions described in Kad et al. (Synlett 2006, 12, 1938-1942).

2,4,7-Trichloropyrido[3,2-d]pyrimidine (3). In a vial of 20 mL, 1.0 g (6.13 mmol, 1 equiv.) of 1H,3H-pyrido[3,2-d]pyrimidine-2,4-dione (2) is suspended in 10 mL of phosphorus oxychloride and 7.65 g (36.7 mmol, 6.0 equiv.) of phosphorus pentachloride (PCl$_5$). The whole is heated under microwave irradiations to 160° C. After 2 hours of reaction, the excess of POCl$_3$ is evaporated under reduced pressure. The obtained residue is brought to 0° C. by means of an ice bath and then solubilized in dichloromethane, the mixture is poured into an ice/water mixture without any basification. After returning to room temperature, the aqueous phase is extracted with dichloromethane. The organic phase is then dried on MgSO$_4$, filtered, and then concentrated under reduced pressure. The thereby obtained residue is chromatographed on a silica gel (petroleum ether/CH$_2$Cl$_2$, 40/60) in order to obtain a white solid with a yield of 64%. MP: 165-166° C.; IR (ATR, Diamond, cm$^{-1}$) v: 3048, 2167, 1579, 1531, 1430, 1324, 1253, 1136, 1001, 872; $^1$H NMR (400 MHz, CDCl$_3$) δ: 8.31 (d, 1H, J=2.2 Hz, H$_8$), 9.03 (d, 1H, J=2.2 Hz, H$_6$); $^{13}$C NMR (100 MHz, CDCl$_3$) δ: 134.2 (CH), 135.1 (Cq), 138.5 (Cq), 148.8 (Cq), 152.7 (CH), 157.0 (Cq), 166.0 (Cq); HRMS (EI-MS): C$_7$H$_2$$^{35}$Cl$_3$N$_3$, calculated m/z 232.9314. found m/z 232.9323.

A.2. Suzuki coupling in position 4 of the compound (3)

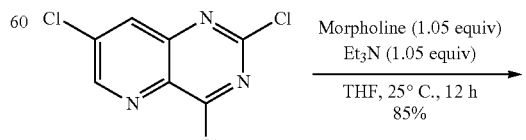

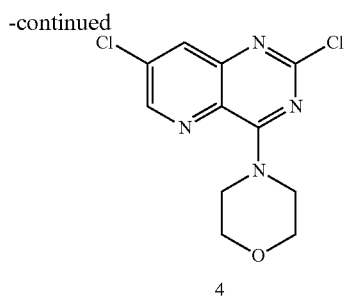

4

Under an argon atmosphere, in a 50 mL flask, 1.0 equiv. of 2,4-trichloropyrido[3,2-d]pyrimidine (3) was dissolved in 20 mL of anhydrous tetrahydrofurane. 1.05 equiv. of triethylamine and 1.05 equiv. of morpholine were then added. The mixture was stirred for 12 hours at room temperature. The solvent was then evaporated and the residue was taken up in dichloromethane (50 mL). The organic phase was washed with an aqueous solution saturated with $NaHCO_3$ (2×15 mL). The organic phase was dried on $MgSO_4$, filtered and then concentrated under reduced pressure. The reaction crude was then purified by a chromatography column on silica gel under pressure (DCM/MeOH, 99/1) in order to obtain a white solid with a yield of 85%. MP: 201° C.; Infrared (Diamand ATR, cm$^{-1}$) v: 3043, 2966, 1546, 1411, 1334, 1254, 1108, 927, 865, 686; $^1$H NMR (250 MHz, CDCl$_3$) δ: 3.87 (t, 4H, J=5.0 Hz, 2×CH$_2$(O)), 4.53 (m, 4H, 2×CH$_2$(N)), 7.99 (dd, 1H, J=2.5 Hz, H$_8$), 8.58 (dd, 1H, J=2.5 Hz, H$_6$); $^{13}$C NMR (101 MHz, CDCl$_3$) δ: 47.8 (2×CH$_2$), 67.1 (2×CH$_2$), 130.7 (Cq), 133.7 (CH), 135.2 (Cq), 145.5 (CH), 149.4 (Cq), 158.3 (Cq), 159.2 (Cq); HRMS (EI-MS): $C_{11}H_{10}Cl_2N_4O$ [M+H]$^+$, calculated m/z 286.0232. found m/z 286.0302.

A.3. Aromatic Nucleophilic Substitution in Position 2 of the Compound (4)

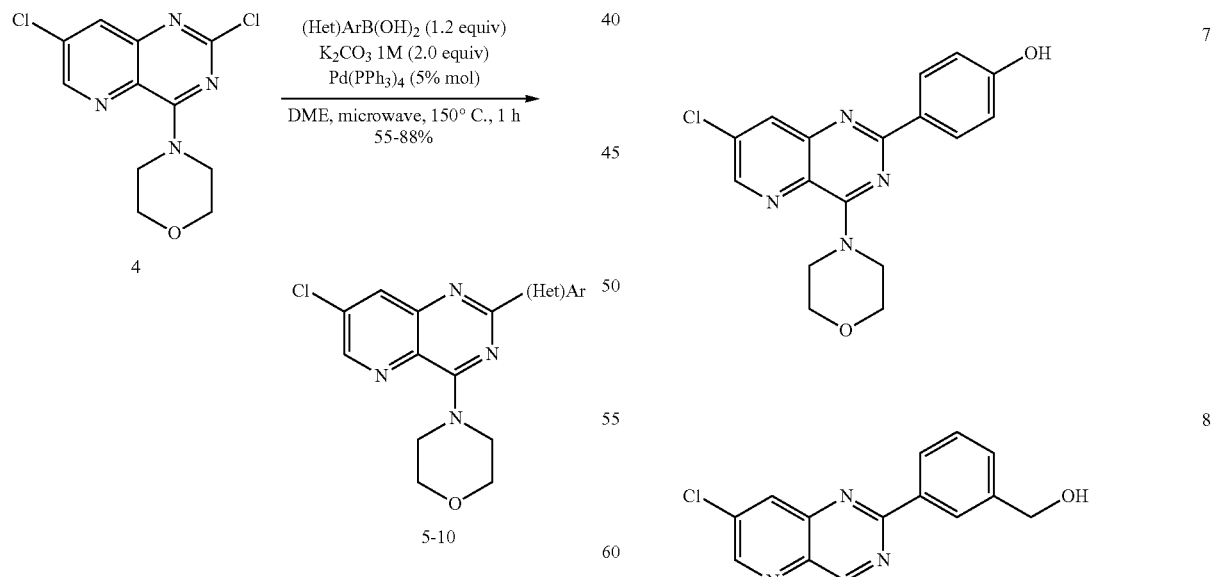

General procedure A:

Under an argon atmosphere, in a 20 mL vial, 1.0 equiv. of (4) was dissolved in dimethoxyethane (10 mL). An aqueous solution (1 mL) containing 2.0 equiv. of potassium carbonate were then added to the medium. 1.2 equiv. of boronic acid were added as well as 0.05 equiv. of tetrakis(triphenylphosphino) palladium(0). The mixture was degassed for 10 minutes before being brought to 150° C. under microwave irradiation for 1 hour. The resulting reaction medium was concentrated under reduced pressure, and then taken up in dichloromethane (30 mL) and washed with water (2×10 mL). The organic phase was dried on $MgSO_4$, filtered and then concentrated under reduced pressure. The reaction crude was then purified by a chromatography column.

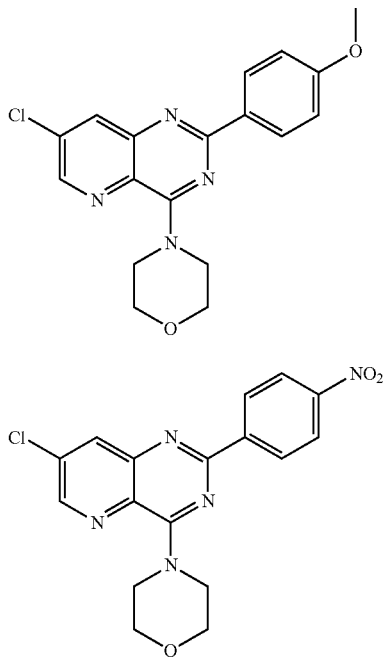

2-(7-Chloro-4-morpholinopyrido[3,2-d]pyrimidin-2-yl) phenol (5): The compound (5) was synthesized from (4) (200 mg, 0.701 mmol) by following the general procedure A and then purified by a chromatography column on silica gel under pressure (AcOEt/EP, 1/9) in the form of a yellow solid with a yield of 76%. MP: 212° C.; Infrared (Diamand ATR, cm$^{-1}$) v: 2926, 1503, 1438, 1314, 1256, 1107, 868, 755; $^1$H NMR (400 MHz, DMSO) δ: 3.93 (s, 4H, 2×CH$_2$(O)), 4.59 (s, 4H, 2×CH$_2$(N)), 6.85 (t, 1H, J=8.0 Hz, H$_{arom}$), 7.08 (d, 1H, J=8.0 Hz, H$_{arom}$), 7.38 (s, 1H, H$_{arom}$), 8.04 (s, 1H, H$_8$), 8.38 (d, 1H, J=8.0 Hz, H$_{arom}$), 8.56 (s, 1H, H$_6$), 13.91 (s, 1H, OH); $^{13}$C NMR (101 MHz, DMSO) δ: 47.6 (2×CH$_2$), 66.3 (2×CH$_2$), 116.7 (CH), 118.0 (CH), 118.8 (CH), 129.7 (CH), 130.7 (Cq), 133.2 (CH), 133.4 (Cq), 138.8 (Cq), 144.9 (CH), 148.3 (Cq), 157.4 (Cq), 158.3 (Cq), 159.8 (Cq); HRMS (EI-MS): C$_{17}$H$_{15}$ClN$_4$O$_2$ [M+H]$^+$, calculated m/z 343.0884. found m/z 343.0952.

3-(7-Chloro-4-morpholinopyrido[3,2-d]pyrimidin-2-yl) phenol (6): The compound (6) was synthesized from (4) (200 mg, 0.701 mmol) by following the general procedure A and then purified by a chromatography column on silica gel under pressure (AcOEt/EP, 3/7) in the form of a white solid with a yield of 73%. MP: 230° C.; Infrared (Diamand ATR, cm$^{-1}$) v: 3301, 2853, 1527, 1425, 1370, 1270, 1229, 1107, 1022, 948, 876, 737; $^1$H NMR (400 MHz, DMSO) δ: 3.85 (t, 4H, J=2.5 Hz, 2×CH$_2$(O)), 4.50 (m, 4H, 2×CH$_2$(N)), 6.95 (d, 1H, J=5.0 Hz, H$_{arom}$), 7.32 (dd, 1H, J=2.5 Hz, J=5.0 Hz, H$_{arom}$), 7.90 (d, 1H, J=2.5 Hz, H$_{arom}$), 7.91 (s, 1H, H$_{arom}$), 8.29 (s, 1H, H$_6$), 8.75 (s, 1H, H$_6$), 9.61 (s, 1H, OH); $^{13}$C NMR (101 MHz, DMSO) δ: 47.6 (2×CH$_2$), 66.3 (2×CH$_2$), 115.0 (CH), 117.8 (CH), 119.1 (CH), 129.3 (CH), 130.7 (Cq), 133.6 (Cq), 134.2 (CH), 138.8 (Cq), 144.9 (CH), 148.3 (Cq), 157.4 (Cq), 158.3 (Cq), 159.8 (Cq); HRMS (EI-MS): C$_{17}$H$_{16}$ClN$_4$O$_2$ [M+H]$^+$, calculated m/z 343.0884. found m/z 343.0956.

4-(7-Chloro-4-morpholinopyrido[3,2-d]pyrimidin-2-yl) phenol (7): The compound (7) was synthesized from (4) (200 mg, 0.701 mmol) by following the general procedure A and then purified by a chromatography column on silica gel under pressure (AcOEt/EP, 2/8) in the form of a yellow solid with a yield of 76%. MP: 253-254° C.; Infrared (Diamand ATR, cm$^{-1}$) v: 2852, 1503, 1413, 1347, 1266, 1151, 1110, 1021, 923, 804, 751; $^1$H NMR (400 MHz, DMSO) δ: 3.80 (d, 4H, J=3.9 Hz, 2×CH$_2$(O)), 4.44 (s, 4H, 2×CH$_2$(N)), 6.86 (m, 2H, 2×H$_{arom}$), 8.20 (s, 1H, H$_8$), 8.27 (d, 2H, J=8.4 Hz, 2×H$_{arom}$), 8.66 (s, 1H, H$_6$), 9.98 (s, 1H, OH); $^{13}$C NMR (101 MHz, DMSO) δ: 47.7 (2×CH$_2$), 66.4 (2×CH$_2$), 115.6 (2×CH), 128.4 (Cq), 130.2 (2×CH), 130.5 (Cq), 133.5 (Cq), 134.0 (CH), 144.4 (CH), 148.5 (Cq), 158.3 (Cq), 160.0 (Cq), 160.2 (Cq); HRMS (EI-MS): C$_{17}$H$_{15}$ClN$_4$O$_2$ [M+H]$^+$, calculated m/z 343.0884. found m/z 343.0968.

(3-(7-Chloro-4-morpholinopyrido[3,2-d]pyrimidin-2-yl) phenyl)methanol (8): The compound (8) was synthesized from (4) (200 mg, 0.701 mmol) by following the general procedure A and then purified by a chromatography column on silica gel under pressure (AcOEt/EP, 1/9) as a yellow solid with a yield of 88%. MP: 157° C.; Infrared (Diamand ATR, cm$^{-1}$) v: 3174, 3044, 2855, 1507, 1417, 1278, 1115, 1025, 874, 726; $^1$H NMR (400 MHz, CDCl$_3$) δ: 3.91 (d, 4H, 2×CH$_2$(O)), 4.56 (bs, 4H, 2×CH$_2$(N)), 4.79 (s, 2H, CH$_2$OH), 7.47 (m, 2H, 2×H$_{arom}$), 8.14 (d, 1H, J=2.4 Hz, H$_8$), 8.37 (d, 1H, J=6.8 Hz, H$_{arom}$), 8.43 (s, 1H, H$_{arom}$), 8.55 (d, 1H, J=2.4 Hz, H$_6$); $^{13}$C NMR (101 MHz, CDCl$_3$) δ: 47.7 (2×CH$_2$), 60.6 (CH$_2$), 66.4 (2×CH$_2$), 127.3 (CH), 128.2 (CH), 128.9 (CH), 129.5 (CH), 131.3 (Cq), 134.6 (Cq), 134.8 (CH), 138.5 (Cq), 141.3 (Cq), 145.2 (CH), 149.0 (Cq), 159.2 (Cq), 161.0 (Cq); HRMS (EI-MS): C$_{18}$H$_{17}$ClN$_4$O$_2$[M+H]$^+$, calculated m/z 357.1113. found m/z 357.1113.

4-(7-chloro-2-(4-methoxyphenyl)pyrido[3,2-d]pyrimidin-4-yl)morpholine (9): The compound (9) was synthesized from (4) (200 mg, 0.701 mmol) by following the general procedure A and then purified by a chromatography column on silica gel under pressure (AcOEt/EP, 1/9) as a yellow solid with a yield of 87%. MP: 176° C.; Infrared (Diamand ATR, cm$^{-1}$) v: 2970, 1502, 1426, 1366, 1299, 1249, 1166, 1107, 1027, 925, 796; $^1$H NMR (400 MHz, CDCl$_3$) δ: 3.88 (s, 3H, OCH$_3$), 3.92 (d, 4H, 2×CH$_2$(O)), 4.55 (s, 4H, 2×CH$_2$(N)), 6.77 (s, 1H, H$_{arom}$), 6.99 (d, 2H, J=8.8 Hz, 2×H$_{arom}$), 8.12 (d, 1H, J=2.3 Hz, H$_8$), 8.43 (d, 2H, J=8.8 Hz, 2×H$_{arom}$), 8.52 (d, 1H, J=2.3 Hz, H$_6$); $^{13}$C NMR (101 MHz, CDCl$_3$) δ: 48.3 (2×CH$_2$), 55.4 (CH$_3$), 67.2 (2×CH$_2$), 113.9 (2×CH), 130.2 (2×CH), 130.8 (Cq), 131.2 (Cq), 134.4 (CH), 134.6 (Cq), 144.7 (CH), 149.2 (Cq), 159.2 (Cq), 161.0 (Cq), 162.1 (Cq); HRMS (EI-MS): C$_{18}$H$_{17}$ClN$_4$O$_2$[M+H]$^+$, calculated m/z 357.1040. found m/z 357.1131.

4-(7-chloro-2-(4-nitrophenyl)pyrido[3,2-d]pyrimidin-4-yl)morpholine (10) The compound (10) was synthesized from (4) (200 mg, 0.701 mmol) by following the general procedure A and then purified by a chromatography column on silica gel under pressure (AcOEt/EP, 1/9) as a yellow solid with a yield of 55%. MP: 200° C.; Infrared (Diamand ATR, cm$^{-1}$) v: 3084, 2983, 2921, 2872, 1594, 1519, 1507, 1342, 1119, 1109, 867; $^1$H NMR (250 MHz, CDCl$_3$) δ: 3.92-3.95 (m, 4H, 2×CH$_2$(O)), 4.60 (bs, 4H, 2×CH$_2$(N)), 8.18 (d, 1H, J=1.5 Hz, HO, 8.32 (d, 2H, J=5.6 Hz, 2×H$_{arom}$), 8.62 (s, 1H, H$_6$), 8.63 (d, 2H, J=5.6 Hz, 2×H$_{arom}$); $^{13}$C NMR (101 MHz, CDCl$_3$) δ: HRMS (EI-MS): C$_{17}$H$_{16}$ClN$_5$O$_3$ [M+H]$^+$, calculated m/z 372.0858. found m/z 372.0859.

A.4. Protection of the hydroxyl functions with a protective group

Route A:

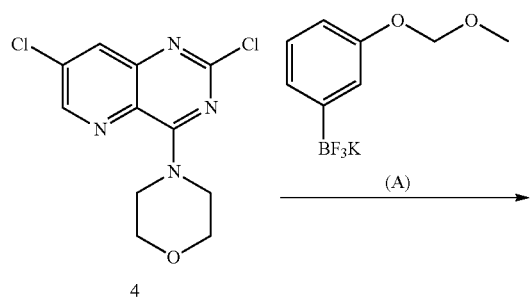

4

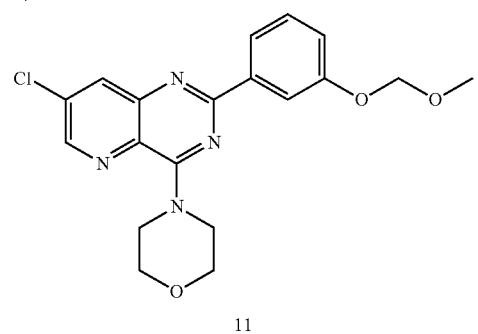

11

Route B:

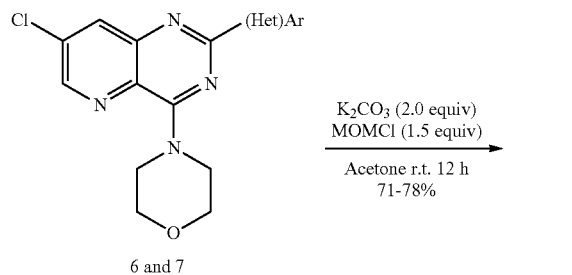

6 and 7

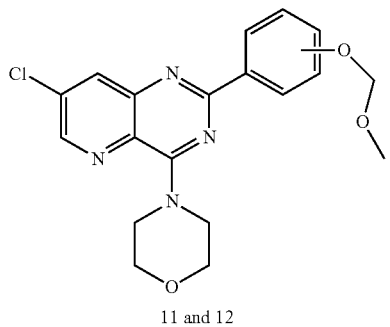

11 and 12

4-(7-chloro-2-(3-(methoxymethoxy)phenyl)pyrido[3,2-d]pyrimidin-4-yl)morpholine (11):

Route A:

The compound (11) was synthesized from (4) (200 mg, 0.701 mmol) by following the general procedure A and then purified by a chromatography column on silica gel under pressure (AcOEt/EP, 2/8) as a yellow solid with a yield of 80%.

Route B:

In a 50 mL flask, 200 mg (0.701 mmol, 1.0 equiv.) of (6) were dissolved in acetone (30 mL), 291 mg (2.1 mmol; 3.0 equiv.) of potassium carbonate and 80 µL (1.05 mmol; 1.5 equiv.) of methyl chloromethyl ether were successively added into the medium. The mixture was left with stirring at room temperature for 12 hours. After concentration under reduced pressure, the residue was taken up in 30 mL of ethyl acetate. The organic phase was washed with a solution saturated with sodium bicarbonate (2×10 mL), dried on $MgSO_4$, filtered and then concentrated under reduced pressure. The product (11) was obtained after purification by a chromatography column on silica gel under pressure (AcOEt/EP, 2/8) as a yellow solid with a yield of 71%. MP: 196° C.; Infrared (Diamond ATR, $cm^{-1}$) v: 2950, 1516, 1454, 1344, 1307, 1266, 1148, 1074, 1009, 874, 731; $^1H$ NMR (400 MHz, $CDCl_3$) δ: 3.53 (s, 3H, $CH_3$), 3.92 (d, 4H, J=4.9 Hz, 2×$CH_2$(O)), 4.57 (bs, 4H, 2×$CH_2$(N)), 5.28 (s, 2H, $CH_2OH$), 7.17 (ddd, 1H, J=1.1 Hz, J=2.4 Hz, J=8.1 Hz, $H_{arom}$), 7.40 (t, 1H, J=8.1 Hz, $H_{arom}$), 8.14 (m, 3H, 2×$H_{arom}$ and $H_6$), 8.59 (d, 1H, J=2.4 Hz, $H_6$); $^{13}C$ NMR (101 MHz, $CDCl_3$) δ: 48.3 (2×$CH_2$), 56.3 ($CH_3$), 66.6 ($CH_2$), 67.5 ($CH_2$), 94.8 ($CH_2$), 116.6 (CH), 118.7 (CH), 120.2 (Cq), 122.4 (CH), 129.6 (CH), 131.3 (Cq), 135.0 (CH), 139.8 (Cq), 145.2 (CH), 149.1 (Cq), 157.6 (Cq), 159.2 (Cq), 160.9 (Cq); HRMS (EI-MS): $C_{19}H_{19}ClN_4O_3[M+H]^+$, calculated m/z 387.1146. found m/z 387.1151.

4-(7-chloro-2-(4-(methoxymethoxy)phenyl)pyrido[3,2-d]pyrimidin-4-yl)morpholine (12): In a 50 mL flask, 200 mg (0.701 mmol, 1.0 equiv.) of (6) were dissolved in acetone (30 mL), 291 mg (2.1 mmol; 3.0 equiv.) of potassium carbonate and 80 µL (1.05 mmol; 1.5 equiv.) of methyl chloromethyl ether were added into the medium. The mixture was left with stirring at room temperature for 12 hours. After concentration under reduced pressure, the residue was taken up into 30 mL of ethyl acetate. The organic phase was washed with a solution saturated with sodium bicarbonate (2×10 mL), dried on $MgSO_4$, filtered and then concentrated under reduced pressure. The compound (12) was isolated after purification by a chromatography column on silica gel under pressure (AcOEt/EP, 2/8) as a yellow solid with a yield of 78%. MP: 138° C.; Infrared (Diamond ATR, cm-1) v: 3084, 3025, 2970, 2917, 1594, 1582, 1494, 1164, 941; $^1H$ NMR (400 MHz, $CDCl_3$) δ: 3.51 (s, 3H, $CH_3$), 3.90-3.93 (m, 4H, 2×$CH_2$(O)), 4.55 (bs, 4H, 2×$CH_2$(N)), 5.25 (s, 2H, $CH_2$), 7.13 (d, 2H, J=8.8 Hz, 2×$H_{arom}$), 8.28 (d, 1H, J=2.4 Hz, HO), 8.38 (d, 2H, J=8.8 Hz, 2×$H_{arom}$), 8.72 (d, 1H, J=2.4 Hz, $H_6$); $^{13}C$ NMR (101 MHz, $CDCl_3$) δ: 48.1 (2×$CH_2$), 56.1 ($CH_3$), 67.2 (2×$CH_2$), 94.3 ($CH_2$), 115.8 (2×CH), 130.2 (2×CH), 131.0 (Cq), 131.7 (Cq), 134.2 (Cq), 134.5 (CH), 144.5 (CH), 149.0 (Cq), 159.0 (Cq), 159.5 (Cq), 160.7 (Cq); HRMS (EI-MS): $C_{19}H_{19}ClN_4O_3[M+H]^+$, calculated m/z 387.1218. found m/z 387.1221.

(11)

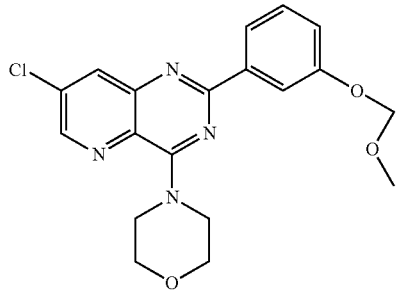

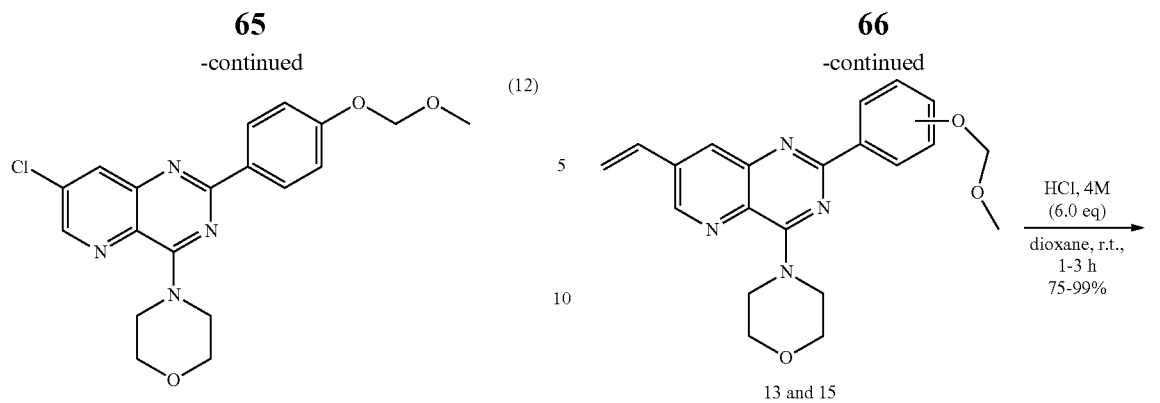

The compound 11 was also able to be synthesized from the compound 4, by means of Suzuki coupling, in the presence of the following boron derivative: poassium 3-methoxyethylether phenyl trifluoroborate (A):

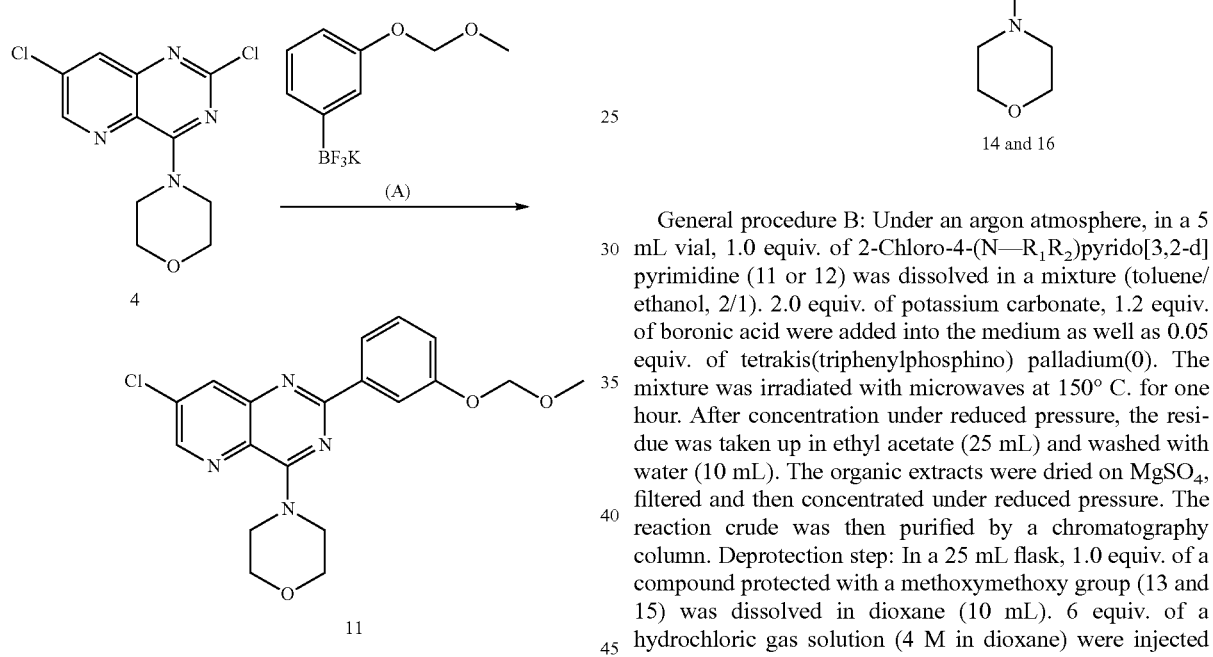

A.5. Functionalization of the Position C-7
A.5.1. Insertion of the Vinyl Function
Procedure B

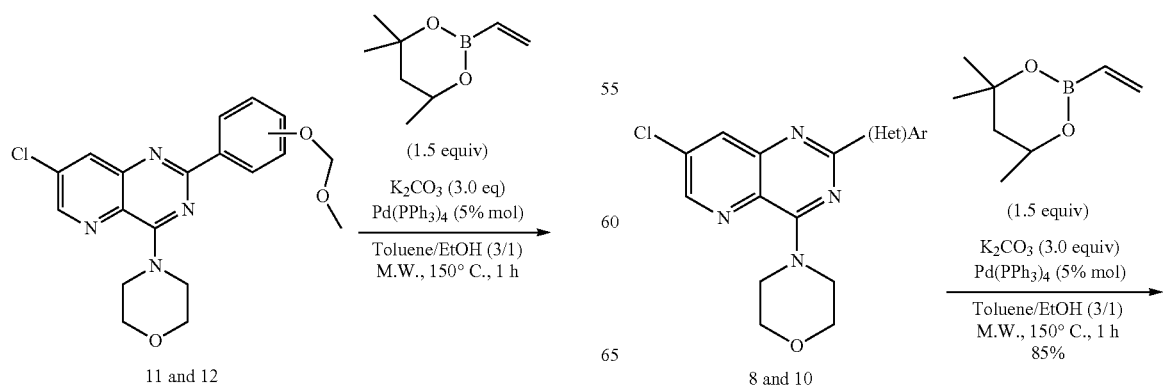

General procedure B: Under an argon atmosphere, in a 5 mL vial, 1.0 equiv. of 2-Chloro-4-(N—$R_1R_2$)pyrido[3,2-d] pyrimidine (11 or 12) was dissolved in a mixture (toluene/ethanol, 2/1). 2.0 equiv. of potassium carbonate, 1.2 equiv. of boronic acid were added into the medium as well as 0.05 equiv. of tetrakis(triphenylphosphino) palladium(0). The mixture was irradiated with microwaves at 150° C. for one hour. After concentration under reduced pressure, the residue was taken up in ethyl acetate (25 mL) and washed with water (10 mL). The organic extracts were dried on $MgSO_4$, filtered and then concentrated under reduced pressure. The reaction crude was then purified by a chromatography column. Deprotection step: In a 25 mL flask, 1.0 equiv. of a compound protected with a methoxymethoxy group (13 and 15) was dissolved in dioxane (10 mL). 6 equiv. of a hydrochloric gas solution (4 M in dioxane) were injected into the medium. The mixture was left with stirring at room temperature for one to three hours. The precipitate was washed with petroleum ether and then recovered by filtration in order to obtain the final product without any additional purification.

Procedure C

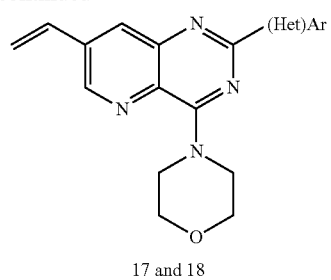

17 and 18

General procedure C:

Under an argon atmosphere, in a 5 mL vial, 1.0 equiv. of 2-Chloro-4-(N—$R_1$, $R_2$)pyrido[3,2-d]pyrimidine (8 or 10) was dissolved in a mixture (toluene/ethanol, 2/1). 2.0 equiv. of potassium carbonate, 1.2 equiv. of boronic acid were added into the medium as well as 0.05 equiv. of tetrakis (triphenylphosphino) palladium(0). The mixture was irradiated with microwaves at 150° C. for one hour. After concentration under reduced pressure, the residue was taken up in ethyl acetate (25 mL) and washed with water (10 mL). The organic extracts were dried on $MgSO_4$, filtered and then concentrated under reduced pressure. The reaction crude was then purified by a chromatography column.

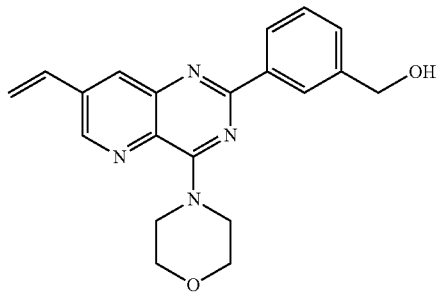

13

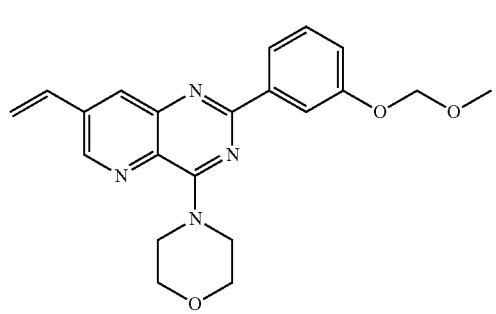

14

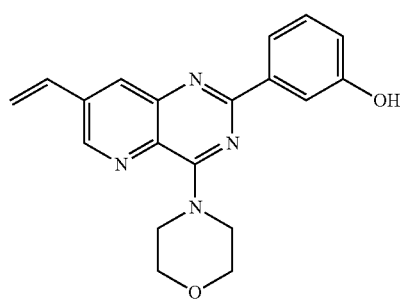

15

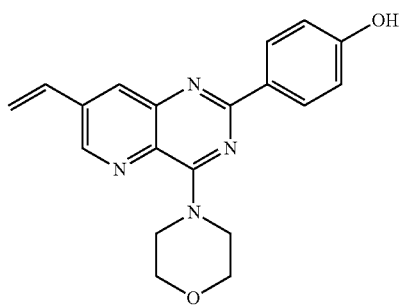

16

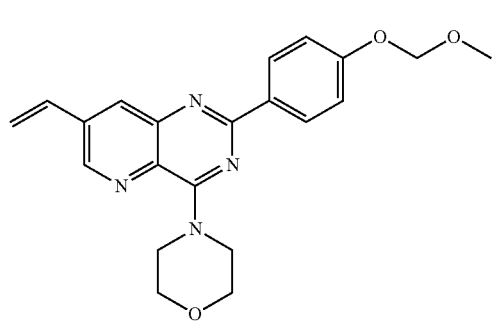

17

18

4-(2-(3-(methoxymethoxy)phenyl)-7-vinylpyrido[3,2-d]pyrimidin-4-yl)morpholine (13):

The compound (13) was synthesized from (11) (250 mg, 0.65 mmol) by following the general procedure B and then purified by chromatography column on silica gel under pressure (AcOEt/EP, 2/8) in order to obtain a yellow solid with a yield of 91%. MP: 105° C.; Infrared (Diamand ATR, $cm^{-1}$) ν: 2856, 1527, 1487, 1454, 1343, 1275, 1111, 1070, 1021, 956, 910, 739; $^1H$ NMR (400 MHz, $CDCl_3$) δ: 3.52 (s, 3H, $CH_3$), 3.96-3.89 (m, 4H, $2 \times CH_2(O)$), 4.58 (bs, 4H, $2 \times CH_2(N)$), 5.28 (s, 2H, $CH_2$), 5.56 (d, 1H, J=11.0 Hz, $CH_{2alkene}$)) 6.05 (d, 1H, J=17.7 Hz, $CH_{2alkene}$), 6.84 (dd, 1H, J=11.0 Hz, J=17.7 Hz, $CH_{alkene}$), 7.20-7.13 (m, 1H, $H_{arom}$), 7.40 (t, 1H, J=7.9 Hz, $H_{arom}$), 8.19-8.09 (m, 3H, $2 \times H_{arom}$ and $H_8$), 8.72 (d, 1H, J=1.9 Hz, $H_6$); $^{13}C$ NMR (101 MHz, $CDCl_3$) δ: 48.3 ($2 \times CH_2$), 56.3 ($CH_3$), 67.5 ($2 \times CH_2$), 94.7 ($CH_2$), 116.5 (CH), 118.4 (CH), 119.0 ($CH_2$), 122.3 (CH), 129.5 (CH), 132.5 (Cq), 132.6 (CH), 133.2 (CH), 136.2 (Cq), 140.2 (Cq), 144.9 (CH), 148.4 (Cq), 157.6 (Cq), 159.4 (Cq), 160.2 (Cq); HRMS (EI-MS): $C_{21}H_{22}N_4O_3$ $[M+H]^+$, calculated m/z 379.1765. found m/z 379.1766.

3-(4-morpholino-7-vinylpyrido[3,2-d]pyrimidin-2-yl) phenol (14): The compound (14) was synthesized from the compound (13) (100 mg, 0.264 mmol) by following the end of the general procedure B in order to obtain a white solid with a yield of 98%. MP: 183° C.; Infrared (Diamand ATR, $cm^{-1}$) ν: 3338, 2856, 1597, 1531, 1483, 1438, 1230, 1107, 968, 858, 739; $^1H$ NMR (400 MHz, $CDCl_3$) δ: 3.89 (m, 4H, 2×CH₂(O)), 4.54 (s, 4H, 2×CH₂(N)), 5.51 (d, 1H, J=11.0 Hz, H$_{alkene}$), 5.99 (d, 1H, J=17.6 Hz, H$_{alkene}$), 6.77 (dd, 1H, J=11.0 Hz, J=17.6 Hz, H$_{alkene}$), 6.92 (d, 1H, J=7.5 Hz, H$_{arom}$), 7.29 (t, 1H, J=7.5 Hz, H$_{arom}$), 7.98 (s, 2H, 2×H$_{arom}$), 8.08 (s, 1H, H₈), 8.70 (d, 1H, H₆); ¹³C NMR (101 MHz, CDCl₃) δ: 48.3 (2×CH₂), 66.1 (CH₂), 67.5 (CH₂), 115.6 (CH), 118.0 (CH), 119.2 (CH₂), 121.0 (CH), 129.8 (CH), 132.2 (CH), 132.3 (Cq), 133.1 (CH), 136.4 (Cq), 140.0 (Cq), 144.9 (CH), 148.2 (Cq), 156.4 (Cq), 159.3 (Cq), 160.5 (Cq); HRMS (EI-MS): C₁₉H₁₈N₄O₂ [M+H]⁺, calculated m/z 335.1430. found m/z 335.1504.

4-(2-(4-(methoxymethoxy)phenyl)-7-vinylpyrido[3,2-d]pyrimidin-4-yl)morpholine (15): The compound (15) was synthesized from (12) (250 mg, 0.65 mmol) by following the general procedure B and then purified by chromatography column on silica gel under pressure (AcOEt/EP, 1/9) for obtaining a yellow solid with a yield of 87%. MP: 95-96° C.; Infrared (Diamand ATR, cm⁻¹) ν: 2856, 1527, 1487, 1454, 1343, 1275, 1111, 1070, 1021, 956, 910, 739; ¹H NMR (400 MHz, CDCl₃) δ: 3.52 (s, 3H, CH₃), 3.96-3.89 (m, 4H, 2×CH₂(O)), 4.58 (bs, 4H, 2×CH₂(N)), 5.28 (s, 2H, CH₂), 5.56 (d, 1H, J=11.0 Hz, CH$_{2alkene}$), 6.05 (d, 1H, J=17.7 Hz, CH$_{2alkene}$), 6.84 (dd, 1H, J=11.0 Hz, J=17.7 Hz, CH$_{alkene}$), 7.20-7.13 (m, 1H, H$_{arom}$), 7.40 (t, 1H, J=7.9 Hz, H$_{arom}$), 8.19-8.09 (m, 3H, 2×H$_{arom}$ and H₈), 8.72 (d, 1H, J=1.9 Hz, H₆); ¹³C NMR (101 MHz, CDCl₃) δ: HRMS (EI-MS): C₂₁H₂₂N₄O₃ [M+H]⁺, calculated m/z 379.1765. found m/z 379.1768.

4-(4-Morpholino-7-vinylpyrido[3,2-d]pyrimidin-2-yl)phenol (16): The compound (16) was synthesized from the compound (15) (100 mg, 0.264 mmol) by following the end of the general procedure B in order to obtain a yellow solid with a yield of 86%. MP: >260° C.; Infrared (Diamand ATR, cm⁻¹) ν: 3292, 2918, 2861, 1591, 1550, 1520, 1503, 1376, 1277, 1130, 1029; ¹H NMR (400 MHz, CDCl₃) δ: 3.83 (bs, 4H, 2×CH₂(O)), 4.47 (bs, 4H, 2×CH₂(N)), 5.61 (d, 1H, J=10.8 Hz, CH$_{2alkene}$), 6.28 (d, 1H, J=17.5 Hz, CH$_{2alkene}$), 6.80 (d, 2H, J=8.4 Hz, 2×H$_{arom}$), 6.96 (dd, 1H, J=10.8 Hz, J=17.5 Hz, CH$_{alkene}$), 8.14 (s, 1H, H₈), 8.26 (d, 2H, J=8.4 Hz, 2×H$_{arom}$), 8.88 (s, 1H, H₆); HRMS (EI-MS): C₁₉H₁₈N₄O₂ [M+H]⁺, calculated m/z 335.1503. found m/z 335.1504.

(3-(4-Morpholino-7-vinylpyrido[3,2-d]pyrimidin-2-yl)phenyl)methanol (17): The compound (17) was synthesized from the compound (8) (210 mg, 0.59 mmol) by following the general procedure C and then purified by chromatography column on silica gel under pressure (AcOEt/EP, 2/8) in order to obtain a yellow solid with a yield of 85%. MP: 160° C.; Infrared (Diamand ATR, cm⁻¹) ν: 3293, 2922, 1488, 1440, 1308, 1109, 1069, 973; ¹H NMR (400 MHz, CDCl₃) δ: 3.92-3.95 (m, 4H, 2×CH₂(O)), 4.60 (bs, 4H, 2×CH₂(N)), 4.81 (s, 2H, CH₂), 5.58 (d, 1H, J=11.0 Hz, H$_{alkene}$), 6.06 (d, 1H, J=17.6 Hz, H$_{alkene}$), 6.86 (dd, 1H, J=11.0 Hz, J=17.6 Hz, H$_{alkene}$), 7.48-7.50 (m, 2H, 2×H$_{arom}$), 8.12 (d, 1H, J=2.1 Hz, H₈), 8.41-8.43 (m, 1H, H$_{arom}$), 8.48 (s, 1H, H$_{arom}$), 8.74 (d, 1H, J=2.1 Hz, H₆); ¹³C NMR (101 MHz, CDCl₃) δ: 48.1 (2×CH₂), 65.4 (CH₂), 67.3 (2×CH₂), 119.0 (CH₂), 127.0 (CH), 127.9 (CH), 128.6 (CH), 129.2 (CH), 132.1 (CH), 132.9 (CH), 136.2 (Cq), 138.4 (Cq), 141.1 (Cq), 144.8 (CH), 148.0 (Cq), 159.1 (Cq), 160.1 (Cq), 167.5 (Cq); HRMS (EI-MS): C₂₀H₂₀N₄O₂[M+H]⁺, calculated m/z 349.1659. found m/z 349.1661.

4-(2-(4-nitrophenyl)-7-vinylpyrido[3,2-d]pyrimidin-4-yl)morpholine (18): The compound (18) was synthesized from the compound (10) (210 mg, 0.59 mmol) by following the general procedure C and then purified by chromatography column on silica gel under pressure (AcOEt/EP, 1/9) in order to obtain a yellow solid with a yield of 85%. MP: >260° C.; Infrared (Diamand ATR, cm⁻¹) ν: 3028, 2972, 2920, 1602, 1553, 1519, 1437, 1345, 1109, 867; ¹H NMR (400 MHz, CDCl₃) δ: 3.90-3.94 (m, 4H, 2×CH₂(O)), 4.56-4.53 (bs, 4H, 2×CH₂(N)), 5.54 (d, 1H, J=11.0 Hz, CH$_{2alkene}$), 6.04 (d, 1H, J=17.7 Hz, CH$_{2alkene}$), 6.84 (dd, 1H, J=11.0 Hz, J=17.7 Hz, CH$_{alkene}$), 8.06 (d, 1H, J=2.2 Hz, H₈), 8.32 (d, 2H, J=8.7 Hz, 2×H$_{arom}$), 8.63 (d, 2H, J=8.6 Hz, 2×H$_{arom}$), 8.71 (d, 1H, J=2.2 Hz, H₆); ¹³C NMR (101 MHz, CDCl₃) δ: 48.2 (2×CH₂), 67.4 (2×CH₂), 114.7 (2×CH), 118.6 (CH₂), 128.7 (Cq), 130.2 (2×CH), 132.2 (Cq), 132.3 (CH), 133.3 (CH), 135.9 (Cq), 144.1 (CH), 147.5 (Cq), 148.9 (Cq), 155.4 (Cq), 160.6 (Cq); HRMS (EI-MS): C₁₉H₁₇N₅O₃ [M+H]⁺, calculated m/z 364.1404. found m/z 364.1407.

A.5.2. Oxidation of the Vinyl Function
Procedure D1 and D2

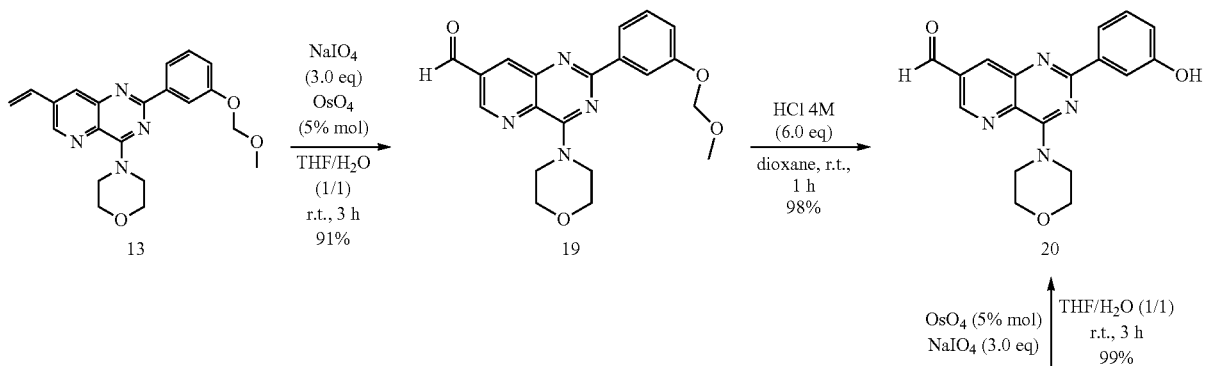

Procedure E1 and E2

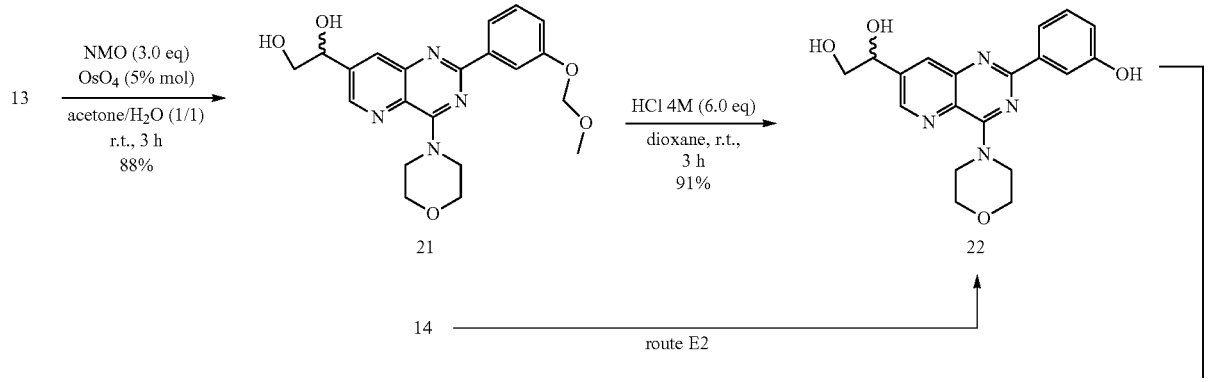

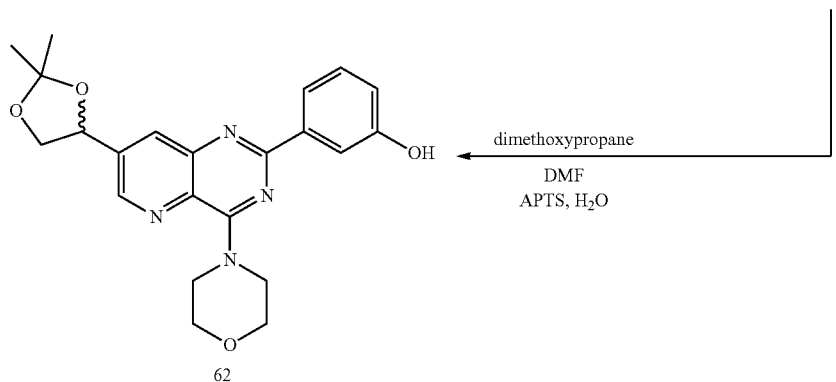

2-(3-(methoxymethoxy)phenyl)-4-morpholinopyrido[3,2-d]pyrimidine-7-carbaldehyde (19): The compound (19) was synthesized according to the first step of procedure D1. In a 25 mL flask, 100 mg (0.3 mmol, 1.0 equiv.) of compound (13) was dissolved in a mixture (THF/H$_2$O, 1/1, 8 mL). 0.2 mL (0.015 mmol, 0.05 equiv.) of osmium tetroxide were injected into the medium. Once the solution had become black, 192 mg (0.9 mmol, 3.0 equiv.) of sodium periodate were added in three times with an interval of five minutes. The solution was stirred for three hours. A 7.5% sodium thiosulfate aqueous solution was added into the medium (10 mL), and then the solution was stirred for 5-10 min, and then filtered on celite. The obtained filtrate was then extracted with ethyl acetate (40 mL) while the resulting organic phase was washed with water (1×10 mL), and then dried on MgSO$_4$, filtered and concentrated under reduced pressure. The compound (19) was isolated as a yellow solid by chromatography column on silica gel under pressure (AcOEt/EP, 2/8) with a yield of 97%. MP: 141° C.; Infrared (Diamand ATR, cm$^{-1}$) v: 2911, 1701, 1508, 1461, 1426, 1268, 1154, 1116, 1071, 1008, 957, 739; $^1$H NMR (400 MHz, CDCl$_3$) δ: 3.43 (s, 3H, CH$_3$), 3.83 (s, 4H, 2×CH$_2$(O)), 4.52 (bs, 4H, 2×CH$_2$(N)), 5.28 (s, 2H, CH$_2$), 7.25-7.13 (m, 1H, H$_{arom}$), 7.45 (t, 1H, J=7.5 Hz, H$_{arom}$), 8.10 (d, 2H, J=7.4 Hz, 2×H$_{arom}$), 8.67 (s, 1H, H$_6$), 9.09 (s, 1H, H$_6$), 10.28 (s, 1H, CHO); $^{13}$C NMR (62.5 MHz, CDCl$_3$) δ: 47.8 (2×CH$_2$), 55.6 (CH$_3$), 66.3 (2×CH$_2$), 94.0 (CH$_2$), 115.7 (CH), 118.5 (CH), 121.7 (CH), 129.6 (CH), 133.3 (Cq), 135.1 (Cq), 138.9 (CH), 139.2 (Cq), 144.4 (CH), 147.4 (Cq), 157.0 (Cq), 158.5 (Cq), 159.7 (Cq), 192.4 (CH); HRMS (EI-MS): C$_{20}$H$_{20}$N$_4$O$_4$ [M+H]$^+$, calculated m/z 381.1557. found m/z 381.1560.

2-(3-hydroxyphenyl)-4-morpholinopyrido[3,2-d]pyrimidine-7-carbaldehyde (20):

Route D2:

In a 25 mL flask, 100 mg (0.30 mmol, 1.0 equiv.) of compound (14) were dissolved in a mixture (THF/H$_2$O, 1/1, 8 mL). 0.2 mL (0.015 mmol, 0.05 equiv.) of osmium tetroxide were injected into the medium. Once the solution had become black, 192 mg (0.9 mmol, 3.0 equiv.) of sodium periodate were added in three times with an interval of five minutes. The solution was stirred for two hours. A 7.5% sodium thiosulfate aqueous solution was added into the medium (10 mL). The solution was stirred for 5-10 min, and then filtered on celite. The obtained filtrate was then extracted with ethyl acetate (40 mL). The resulting organic phase was washed with water (1×10 mL). The organic extract was dried on MgSO$_4$, filtered and then concentrated under reduced pressure and then purified by chromatography column on silica gel under pressure (AcOEt/EP, 2/8) in order to obtain a yellow solid with a yield of 99%.

Route D1:

The compound (20) was synthesized from the compound (19) (100 mg, 0.30 mmol) by following the deprotection step of the general procedure D1 (similar to the deprotection step of procedure B) in order to obtain a yellow solid with a yield of 90%.

MP: 182° C.; Infrared (Diamand ATR, cm$^{-1}$) ν: 2852, 1695, 1556, 1516, 1426, 1377, 1283, 1107, 1025, 882, 743; $^1$H NMR (400 MHz, DMSO) δ: 3.84 (m, 4H, 2×CH$_2$(O)), 4.52 (s, 4H, 2×CH$_2$(N)), 4.79 (s, 2H, CH$_2$OH), 6.92 (m, 1H, H$_{arom}$), 7.30 (t, 1H, J=8.1 Hz, H$_{arom}$), 7.90 (m, 2H, 2×H$_{arom}$), 8.64 (d, 1H, J=1.9 Hz, H$_6$), 9.09 (d, 1H, J=1.9 Hz, H$_6$), 9.58 (s, 1H, OH), 10.28 (s, 1H, CHO); $^{13}$C NMR (101 MHz, DMSO) δ: 48.1 (2×CH$_2$), 66.3 (2×CH$_2$), 114.9 (CH), 117.78 (CH), 119.1 (CH), 129.4 (CH), 133.3 (Cq), 136.1 (Cq), 138.8 (CH), 139.0 (Cq), 144.3 (CH), 147.43 (Cq), 157.5 (Cq), 158.4 (Cq), 159.7 (Cq), 192.4 (CH); HRMS (EI-MS): C$_{18}$H$_{16}$N$_4$O$_3$[M+H]$^+$, calculated m/z 337.1563. found m/z 337.1546.

1-(2-(3-(methoxymethoxy)phenyl)-4-morpholinopyrido[3,2-d]pyrimidin-7-yl)ethane-1,2-diol (21): The compound (21) was synthesized according to the first step of the following procedure E1. In a 25 mL flask, 80 mg (0.24 mmol, 1.0 equiv.) of compound (13) were dissolved in a mixture (Acetone/H$_2$O, 3/1, 8 mL). 0.2 mL (0.012 mmol, 0.05 equiv.) of osmium tetroxide were injected into the medium. Once the solution had become black, 42 mg (0.36 mmol, 1.5 equiv.) of N-methylmorpholine-N-oxide (NMO) were added in two times at an interval of five minutes. The solution was left with stirring for two hours. A 10% sodium thiosulfate aqueous solution (10 mL) was added into the medium. The solution was stirred for 5-10 min, and then filtered on celite. The obtained filtrate was then extracted with ethyl acetate (40 mL). The resulting organic phase was washed with water (10 mL). The organic extract was dried on MgSO$_4$, filtered and then concentrated under reduced pressure and then purified by chromatography column on silica gel under pressure (AcOEt/EP, 2/8) in order to obtain a white solid with a yield of 88%. MP: 167° C.; Infrared (Diamand ATR, cm$^{-1}$) ν: 3444, 2921, 1495, 1442, 1356, 1266, 1152, 1078, 1013, 743; $^1$H NMR (400 MHz, DMSO) δ: 3.42 (s, 3H, CH$_3$), 3.61 (m, 2H, CH$_2$OH), 3.82 (m, 4H, 2×CH$_2$(O)), 4.52 (bs, 4H, 2×CH$_2$(N)), 4.80 (q, 1H, J=5.4 Hz, OH), 4.88 (t, 1H, J=5.8 Hz, CHOH), 5.28 (s, 2H, CH$_2$), 5.67 (d, 1H, J=4.7 Hz, OH), 7.17 (m, 1H, H$_{arom}$), 7.43 (t, 1H, J=8.2 Hz, H$_{arom}$), 8.09 (m, 3H, 2×H$_{arom}$ and H$_8$), 8.75 (d, 1H, J=2.0 Hz, H$_6$); $^{13}$C NMR (101 MHz, DMSO) δ: 48.1 (2×CH$_2$), 55.6 (CH$_3$), 66.4 (2×CH$_2$), 66.5 (CH$_2$), 71.3 (CH), 94.0 (CH$_2$), 115.5 (CH), 118.2 (CH), 121.5 (CH), 129.4 (CH), 131.2 (Cq), 132.9 (CH), 139.4 (Cq), 143.3 (Cq), 146.1 (CH), 147.4 (Cq), 156.9 (Cq), 158.3 (Cq), 158.5 (Cq); HRMS (EI-MS): C$_{21}$H$_{24}$N$_4$O$_5$[M+H]$^+$, calculated m/z 413.1747. found m/z 413.1825.

1-(2-(3-hydroxyphenyl)-4-morpholinopyrido[3,2-d]pyrimidin-7-yl)ethane-1,2-diol (24):

Route E2:

In a 25 mL flask, 80 mg (0.24 mmol, 1.0 equiv.) of the compound (14) were dissolved in a mixture (Acetone/H$_2$O, 3/1, 8 mL). 0.2 mL (0.012 mmol, 0.05 equiv.) of osmium tetroxide were injected into the medium. Once the solution had become black, 42 mg (0.36 mmol, 1.5 equiv.) of N-methylmorpholine-N-oxide (NMO) were added in two times with an interval of five minutes. The solution was left with stirring for two hours. A 10% sodium thiosulfate aqueous solution (10 mL) was added into the medium. The solution was stirred for 5-10 min, and then filtered on celite. The obtained filtrate was then extracted with ethyl acetate (40 mL). The resulting organic phase was washed with water (10 mL). The organic extract was dried on MgSO$_4$, filtered and then concentrated under reduced pressure and then purified by chromatography column on silica gel under pressure (DCM/MeOH, 98/2) in order to obtain a white solid with a yield of 88%.

Route E1:

The compound (22) was synthesized from the compound (14) (80 mg, 0.24 mmol) by following the deprotection step of the general procedure E1 (similar to the deprotection step of the procedure B) in order to obtain a white solid with a yield of 91%.

MP: 206° C.; Infrared (Diamand ATR, cm$^{-1}$) ν: 3293, 2856, 1528, 1495, 1442, 1352, 1111, 1021, 861, 739; $^1$H NMR (400 MHz, DMSO) δ: 3.32 (m, 2H, CH$_2$OH), 3.82 (m, 4H, 2×CH$_2$(O)), 4.52 (s, 4H, 2×CH$_2$(N)), 4.80 (d, 1H, OH), 4.88 (t, 1H, CHOH), 5.66 (d, 1H, OH), 6.90 (t, 1H, J=8.1 Hz, H$_{arom}$), 7.29 (m, 2H, 2×H$_{arom}$), 7.90 (d, 1H, J=1.9 Hz, H$_8$), 8.07 (d, 1H, H$_6$), 9.53 (s, 1H, OH); $^{13}$C NMR (101 MHz, DMSO) δ: 48.1 (2×CH$_2$), 66.4 (2×CH$_2$), 66.5 (CH$_2$), 71.3 (CH), 114.1 (CH), 117.4 (CH), 118.9 (CH), 129.3 (CH), 131.2 (Cq), 132.8 (CH), 139.3 (Cq), 143.2 (Cq), 145.9 (CH) 147.4 (Cq). 157.3 (Cq), 158.5 (Cq), 158.7 (Cq); HRMS (EI-MS): C$_{19}$H$_{20}$N$_4$O$_4$ [M+H]$^+$, calculated m/z 369.1485. found m/z 369.1554.

4-[7-(2,2-dimethyl-1,3-dioxolan-4-yl)-2-[3-(methoxymethoxy)phenyl]pyrido[3,2-d]pyrimidin-4-yl]morpholine (62): In a 10 mL flask, 83 mg (0.23 mmol; 1 equiv.) of (22) was suspended in 2 mL of dimethylformamide (DMF). 142.6 μL (1.15 mmol, 5 equiv.) of 2,2-dimethoxypropane and 4 mg of para-toluenesulfonic acid monohydrate (APTS.H$_2$O) were added. After one hour at room temperature, an aqueous solution saturated with NaHCO$_3$ (10 mL) was added. The organic phase was extracted three times with ethyl acetate (10 mL), washed with a saturated saline solution, dried on MgSO$_4$, filtered and then concentrated under reduced pressure. The crude residue was then purified by chromatography column on silica gel under pressure (AE/EP 30/70) allowing isolation of a white solid with a yield of 53%; MP: 210° C.; Infrared (Diamand ATR, cm$^{-1}$) ν: 3293, 2856, 1557, 1513, 1495, 1429, 1352, 1111, 1021, 861, 739; $^1$H NMR (400 MHz, DMSO) δ: 1.46 and 1.53 (2 s, 6H, 2×CH$_3$), 3.82 (m, 4H, 2×CH$_2$(O)), 4.46 (m, 2H, CH$_2$), 4.48 (s, 4H, 2×CH$_2$(N)), 5.34 (t, 1H, J=6.7 Hz, CH), 6.90 (t, 1H, J=8.1 Hz, H$_{arom}$), 7.29 (m, 2H, 2×H$_{arom}$), 7.90 (d, 1H, J=1.9 Hz, H$_8$), 8.07 (d, 1H, H$_6$), 9.53 (s, 1H, OH); $^{13}$C NMR (101 MHz, DMSO) δ: 26.1 (CH$_3$), 26.8 (CH$_3$), 48.4 (2×CH$_2$), 66.9 (2×CH$_2$), 70.58 (CH$_2$), 75.1 (CH), 110.22 (Cq), 115.5 (CH), 117.3 (CH), 119.8 (CH), 129.9 (CH), 132.28 (Cq), 133.6 (CH), 139.6 (Cq), 140.0 (Cq), 145.6 (CH), 147.4 (Cq), 157.9 (Cq), 158.9 (Cq), 159.5 (Cq); HRMS (EI-MS): C$_{22}$H$_{26}$N$_4$O$_4$[M+H]$^+$, calculated m/z 409.1876. found m/z 409.1876.

A.5.3. Preparation of Amine Derivatives by Reducing Amination

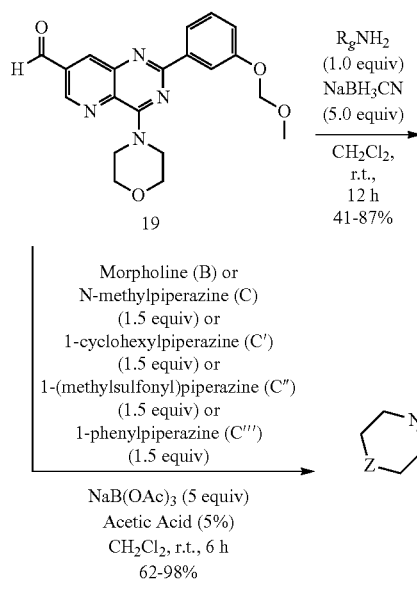
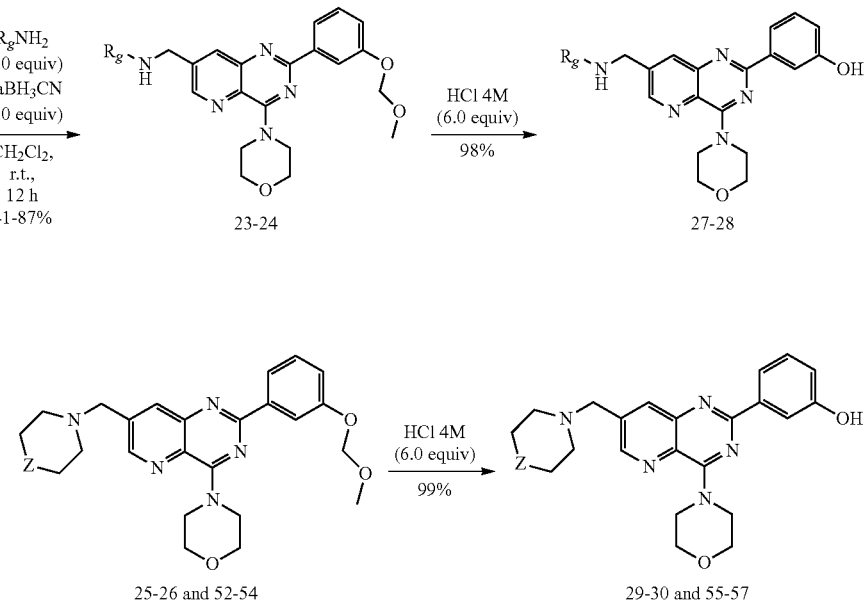

3-(7-((cyclopropylamino)methyl)-4-morpholinopyrido[3,2-d]pyrimidin-2-yl)phenolhydrochloride (27): In a 25 mL flask, under an inert atmosphere, 70 mg (0.184 mmol; 1 equiv.) of (19) was dissolved in 5 mL of anhydrous dichloromethane. A spatula tip of MgSO$_4$ was added into the medium as well as 12 μL (0.184 mmol; 1 equiv.) of cyclopropylamine. The mixture was stirred at room temperature overnight. The MgSO$_4$ was removed by filtration on a frit and the filtrate was concentrated under reduced pressure. The residue was taken up in 5 mL of methanol to which 60 mg (0.92 mmol; 5 equiv.) of sodium cyanohydroboride were added. After 20 minutes of stirring at room temperature, the reaction medium was concentrated under reduced pressure.

Deprotection step: In a 25 mL flask, 1.0 equiv. of compound (23) was dissolved in dioxane (10 mL). 6 equiv. of a hydrochloric acid gas solution (4 M in dioxane) were injected into the medium. The mixture was left with stirring at room temperature for one to three hours. The precipitate was washed with petroleum ether and then recovered by filtration in order to obtain the compound (27) with a yield of 40% so as to obtain a white solid. MP: 244° C.; Infrared (Diamand ATR, cm$^{-1}$) ν: 3351, 3047, 1613, 1552, 1517, 1428, 1385, 1310, 1114, 1024, 864, 732; $^1$H NMR (400 MHz, DMSO) δ: 0.81 (s, 2H, 2×H$_{cyclopropyl}$), 1.09 (s, 2H, 2×H$_{cyclopropyl}$), 2.72 (s, 1H, H$_{cyclopropyl}$), 3.87 (s, 4H, 2×CH$_2$(O)), 4.48 (s, 2H, CH$_2$), 4.64 (bs, 4H, 2×CH$_2$(N)), 7.06 (s, 1H, H$_{arom}$), 7.38 (s, 1H, H$_{arom}$), 7.91 (d, 2H, J=11.7 Hz, 2×H$_{arom}$), 8.70 (s, 1H, H$_8$), 9.10 (s, 1H, H$_6$), 10.39 (s, 1H, NH); $^{13}$C NMR (101 MHz, DMSO) δ: HRMS (EI-MS): C$_{21}$H$_{23}$N$_5$O$_2$ [M+H]$^+$, calculated m/z 378.1852. found m/z 378.1927.

3-(7-((cyclohexylamino)methyl)-4-morpholinopyrido[3,2-d]pyrimidin-2-yl)phenol hydrochloride (28): In a 25 mL flask, under an inert atmosphere, 80 mg (0.21 mmol; 1 equiv.) of (19) were dissolved in 5 mL of anhydrous dichloromethane. A spatula tip of MgSO$_4$ was added into the medium as well as 24 μL (0.21 mmol; 1 equiv.) of cyclohexylamine. The mixture was stirred at room temperature overnight. The MgSO$_4$ was removed by filtration on a frit and the filtrate was concentrated under reduced pressure. The residue was taken up in 5 mL of methanol to which 69 mg (1.05 mmol; 5 equiv.) of sodium cyanohydroboride were added. After 20 minutes of stirring at room temperature, the mixture was concentrated under reduced pressure.

Deprotection step: In a 25 mL flask, 1.0 equiv. of the compound (24) was dissolved in dioxane (10 mL). 6 equiv. of a hydrochloric acid gas solution (4 M in dioxane) were injected into the medium. The mixture was left with stirring at room temperature for one to three hours. The precipitate was washed with petroleum ether and then recovered by filtration in order to obtain a white solid with a yield of 85%. MP: 254° C.; Infrared (Diamand ATR, cm$^{-1}$) ν: 3364, 2933, 1617, 1556, 1510, 1428, 1388, 1110, 732; $^1$H NMR (400 MHz, DMSO) δ: 1.17 (m, 6H, 6×H$_{cyclohexane}$), 1.56 (m, 2H, 2×H$_{cyclohexane}$), 1.76 (m, 2H, 2×H$_{cyclohexane}$), 2.18 (m, 1H, H$_{cyclohexane}$), 3.83 (s, 4H, 2×CH$_2$(O)), 4.38 (s, 2H, CH$_2$), 4.54 (s, 4H, 2×CH$_2$(N)), 6.96 (s, 1H, H$_{arom}$), 7.30 (s, 1H, H$_{arom}$), 7.92 (s, 2H, 2×H$_{arom}$), 8.55 (s, 1H, H$_8$), 9.03 (s, 1H, H$_6$), 9.80 (bs, 1H, OH), 10.05 (bs, 1H, NH); $^{13}$C NMR (101 MHz, DMSO) δ: HRMS (EI-MS): C$_{24}$H$_{29}$N$_5$O$_2$[M+H]$^+$, calculated m/z 420.2394. found m/z 420.2390.

3-(4-morpholino-7-(morpholinomethyl)pyrido[3,2-d]pyrimidin-2-yl) phenol hydrochloride (29): In a 25 mL flask, under an inert atmosphere, 80 mg (0.21 mmol; 1 equiv.) of (19) were dissolved in 6 mL of a mixture (DCM/DMF, 5/1). After having injected 28 μL (0.315 mmol; 1.5 equiv.) of morpholine, the mixture was cooled to 0° C. by means of an ice bath and 223 mg (1.051 mmol; 5 equiv.) of sodium triacetatehydroboride were added thereto. After 10 minutes of stirring at 0° C., 4 drops of acetic acid were added, the solution was then left with stirring at room temperature for 6 hours. 5 mL of water and 40 mL of dichloromethane were then added. The resulting organic phase was washed with an aqueous solution saturated with NaHCO$_3$ (10 mL), dried on MgSO$_4$, filtered and then concentrated under reduced pressure.

The deprotection step of MOM was directly carried out with the residue (25), which was dissolved in dioxane (10 mL). 6 equiv. of a hydrochloric acid gas solution (4 M in dioxane) were injected into the medium. The mixture was left with stirring at room temperature for one to three hours. The precipitate was washed with petroleum ether and then recovered by filtration in order to obtain a white solid (29) with a yield of 61%. MP: 239° C.; Infrared (Diamand ATR, cm$^{-1}$) v: 3344, 3037, 1552, 1510, 1417, 1292, 1114, 1028, 864, 736; $^1$H NMR (400 MHz, DMSO) δ: 3.26 (bs, 4H, 2×CH$_2$(N)), 3.86 (bs, 8H, 4×CH$_2$(O)), 4.63 (bs, 6H, CH$_2$ and 2×CH$_2$(N)), 7.03 (s, 1H, H$_{arom}$), 7.37 (s, 1H, H$_{arom}$), 7.96 (m, 2H, 2×H$_{arom}$), 8.76 (s, 1H, H$_8$), 9.13 (s, 1H, H$_6$), 12.35 (s, 1H, NH); $^{13}$C NMR (101 MHz, DMSO) δ: HRMS (EI-MS): C$_{22}$H$_{25}$N$_5$O$_3$[M+H]$^+$, calculated m/z 408.1957. found m/z 408.2020.

3-(7-((4-methylpiperazin-1-yl)methyl)-4-morpholin-opyrido[3,2-d]pyrimidin-2-yl)phenol hydrochloride (30): In a 25 mL flask, under an inert atmosphere, 100 mg (0.263 mmol; 1 equiv.) of (19) were dissolved in 6 mL of a mixture (dichloromethane/DMF, 5/1). After having injected 44 µL (0.394 mmol; 1.5 equiv.) of N-methylpiperazine, the mixture was cooled to 0° C. by means of an ice bath and 279 mg (1.315 mmol; 5 equiv.) of sodium triacetatehydroboride were added thereto. After 10 minutes of stirring at 0° C., 4 drops of acetic acid were added and the solution was left with stirring at room temperature for 6 hours. 5 mL of water and 40 mL of dichloromethane were then added. The resulting organic phase was washed with an aqueous solution saturated with NaHCO$_3$ (10 mL), dried on MgSO$_4$, filtered and then concentrated under reduced pressure.

The MOM deprotection step was directly carried out with the reaction intermediate (26), by dilution in dioxane and addition of 6 equiv. of a hydrochloric acid gas solution (4 M in dioxane). The mixture was then left with stirring at room temperature for one to three hours. The precipitate was washed with petroleum ether and then recovered by filtration in order to obtain a white solid with a yield of 92%. MP: 243° C.; Infrared (Diamand ATR, cm$^{-1}$) v: 2927, 1616, 1556, 1508, 1420, 1388, 1312, 1112, 881, 729; $^1$H NMR (400 MHz, DMSO) δ: 2.81 (s, 3H, NCH$_3$), 3.46 (s, 2H, CH$_2$(N)), 3.88 (s, 5H, H and 2×CH$_2$(O)), 4.86-4.45 (m, 6H, 3×CH$_2$(N)), 7.10 (d, 1H, J=7.2 Hz, H$_{arom}$), 7.40 (t, 1H, J=8.2 Hz, H$_{arom}$), 7.99-7.76 (m, 2H, 2×H$_{arom}$), 8.81 (s, 1H, H$_8$), 9.10 (s, 1H, H$_6$), 11.91 (s, 1H, NH); $^{13}$C NMR (101 MHz, DMSO) δ: HRMS (EI-MS): C$_{22}$H$_{26}$N$_6$O$_3$[M+H]$^+$, calculated m/z 421.2274. found m/z 421.2361.

3-{7-[(4-methanesulfonylpiperazin-1-yl)methyl]-4-(morpholin-4-yl)pyrido[3,2-d]pyrimidin-2-yl}phenol (55): In a 25 mL flask, under an inert atmosphere, 100 mg (0.26 mmol; 1 equiv.) of (19) were dissolved in 6 mL of a mixture (DCM/DMF, 5/1). After having added 64 mg (0.39 mmol; 1.5 equiv.) of 1-(methylsulfonyl)piperazine, the mixture was cooled to 0° C. by means of an ice bath and 165 mg (0.78 mmol; 5 equiv.) of sodium triacetatehydroboride were added thereto. After 10 minutes of stirring at 0° C., 4 drops of acetic acid were added, the solution was then left with stirring at room temperature for 5 hours. 10 mL of water and 40 mL of dichloromethane were then added. The resulting organic phase was washed with an aqueous solution saturated with NaHCO$_3$ (10 mL), dried on MgSO$_4$, filtered and then concentrated under reduced pressure.

Deprotection step: In a 25 mL flask, 1.0 equiv. of the residue obtained was dissolved in dioxane (10 mL). 6 equiv. of a hydrochloric acid gas solution (4 M in dioxane) were injected into the medium. The mixture was left with stirring at room temperature for one to three hours. The precipitate was washed with petroleum ether and then recovered by filtration in order to obtain a grayish solid (55) with a yield of 98%. MP: 208° C.; Infrared (Diamand ATR, cm$^{-1}$) v: 3344, 3037, 1552, 1510, 1417, 1292, 1114, 1028, 864, 736; $^1$H NMR (400 MHz, DMSO+D$_2$O) δ: 2.96 (s, 3H, CH$_3$), 3.26 (bs, 4H, 2×CH$_2$(N)), 3.30 (bs, 4H, 2×CH$_2$(N)), 3.40 (bs, 4H, 2×CH$_2$(N)), 3.83 (bs, 4H, 2×CH$_2$(O)), 4.54 (s, 2H, CH$_2$), 4.58 (bs, 4H, 2×CH$_2$(N)), 6.99 (dd, J=8.0, 2.5 Hz, 1H, H$_{arom}$), 7.36 (t, J=7.9 Hz, 1H, H$_{arom}$), 7.88-7.77 (m, 2H, H$_{arom}$), 8.43 (d, J=2.1 Hz, 1H, H$_{arom}$), 8.90 (d, J=2.1 Hz, 1H, H$_{arom}$); $^{13}$C NMR (101 MHz, DMSO) δ: HRMS (EI-MS): C$_{23}$H$_{29}$N$_6$O$_4$S [M+H]$^+$, calculated m/z 485.1966. found m/z 485.1961.

3-{7-[(4-cyclohexylpiperazin-1-yl)methyl]-4-(morpholin-4-yl)pyrido[3,2-d]pyrimidin-2yl}phenol (56): Under an inert atmosphere, in a 25 mL flask, 50 mg (0.13 mmol; 1 equiv.) of (19) were dissolved in 5 mL of a mixture (DCM/DMF, 5/1). After having added 33 mg (0.19 mmol; 1.5 equiv.) of 1-cyclohexylpiperazine, the mixture was cooled to 0° C. by means of an ice bath and 138 mg (0.66 mmol; 5 equiv.) of triacetatehydroboride were added thereto. After 10 minutes of stirring at 0° C., 4 drops of acetic acid were added, the solution was then left with stirring at room temperature for five hours. 10 mL of water and 40 mL of dichloromethane were then added. The resulting organic phase was washed with an aqueous solution saturated with NaHCO$_3$ (10 mL), dried on MgSO$_4$, filtered and then concentrated under reduced pressure.

The MOM deprotection step was directly carried out with the reaction intermediate (53), by dilution in dioxane and addition of 6 equiv. of a hydrochloric acid gas solution (4 M in dioxane). The mixture was left with stirring at room temperature for one to three hours. The precipitate was washed with petroleum ether and then recovered by filtration in order to obtain a brown solid (56) with a yield of 58%. MP: 250° C.; Infrared (Diamand ATR, cm$^{-1}$) v: 3344, 3037, 1552, 1510, 1417, 1292, 1114, 1028, 864, 736; $^1$H NMR (400 MHz, DMSO) δ: 1.18-150 (m, 6H, CH$_2$), 1.6 (m, 1H, CH), 1.82 (m, 2H, CH$_2$), 2.18 (m, 2H, CH$_2$), 3.45 (bs, 4H, 2×CH$_2$(N)), 3.60 (bs, 4H, 2×CH$_2$(N)), 3.40 (bs, 4H, 2×CH$_2$(N)), 3.90 (bs, 4H, 2×CH$_2$(O)), 4.46 (bs, 4H, 2×CH$_2$(N)), 4.70 (s, 2H, CH$_2$), 6.99 (dd, J=8.0, 2.5 Hz, 1H, H$_{arom}$)) 7.36 (t, J=7.9 Hz, 1H, H$_{arom}$), 7.88-7.77 (m, 2H, H$_{arom}$), 8.43 (d, J=2.1 Hz, 1H, H$_{arom}$), 8.90 (d, J=2.1 Hz, 1H, H$_{arom}$), 11.51 (s, 1H, NH); $^{13}$C NMR (101 MHz, DMSO) δ: HRMS (EI-MS): C$_{28}$H$_{37}$N$_6$O$_2$[M+H]$^+$, calculated m/z 489.2978. found m/z 489.2973.

3-[4-(morpholin-4-yl)-7-[(4-phenylpiperazin-1-yl)methyl]pyrido[3,2-d]pyrimidin-2-yl]phenol (57): Under an inert atmosphere, in a 25 mL flask, 50 mg (0.13 mmol; 1 equiv.) of (19) were dissolved in 5 mL of a mixture (DCM/DMF, 5/1). After having added 30 µL (0.19 mmol; 1.5 equiv.) of 1-cyclohexylpiperazine, the mixture was cooled to 0° C. by means of an ice bath and 139 mg (0.66 mmol; 5 equiv.) of sodium triacetatehydroboride were added thereto. After 10 minutes of stirring at 0° C., 4 drops of acetic acid were added, the solution was then left with stirring at room temperature for 5 hours. 10 mL of water and 40 mL of dichloromethane were then added. The resulting organic phase was washed with an aqueous solution saturated with NaHCO$_3$ (10 mL), dried on MgSO$_4$, filtered and then concentrated under reduced pressure.

The MOM deprotection step was directly carried out with the reaction intermediate (54), by dilution in dioxane and addition of 6 equiv. of a hydrochloric acid gas solution (4 M in dioxane). The mixture was left with stirring at room temperature for one to three hours. The precipitate was washed with petroleum ether and then recovered by filtration in order to obtain a brown solid (57) with a yield of 58%.

MP>250° C.; Infrared (Diamand ATR, cm$^{-1}$) ν: 3271, 1552, 1510, 1417, 1292, 1114, 1028, 864, 736; $^1$H NMR (400 MHz, DMSO) δ: 3.26 (bs, 4H, 2×CH$_2$(N)), 3.47 (bs, 4H, 2×CH$_2$(N)), 3.89 (bs, 4H, 2×CH$_2$(O)), 4.20 (bs, 4H, 2×CH$_2$ (N)), 4.70 (s, 2H, CH$_2$), 6.87 (t, J=7.3 Hz, 1H, H$_{arom}$), 7.0 (m, 2H, H$_{arom}$), 7.08 (d, J=2.3 Hz, 1H, H$_{arom}$), 7.27 (m, 2H, H$_{arom}$) 7.41 (t, J=7.9 Hz, 1H, H$_{arom}$), 7.86 (t, J=2.0 Hz, 1H, H$_{arom}$), 7.91 (m, 1H, H$_{arom}$), 8.71 (d, J=3.4 Hz, 1H, H$_{arom}$), 9.17 (d, J=2.8 Hz, 1H, H$_{arom}$)) 12.08 (s, 1H, NH); $^{13}$C NMR (101 MHz, DMSO) δ: HRMS (EI-MS): C$_{28}$H$_{31}$N$_6$O$_2$ [M+H]$^+$, calculated m/z 483.2508. found m/z 489.2903.
23
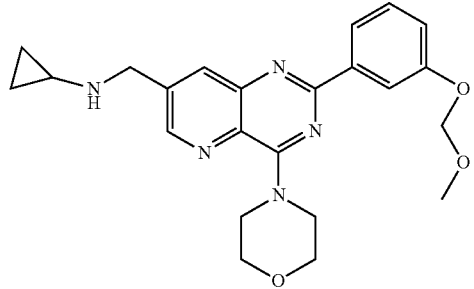
24
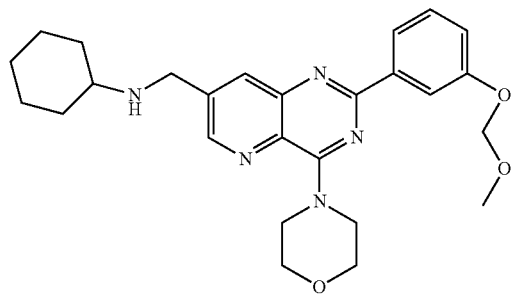
25
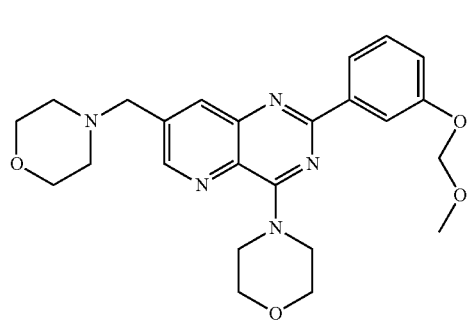
26
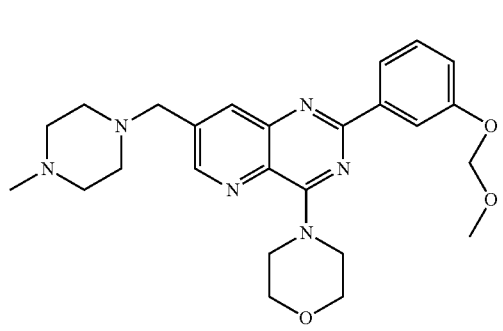
27
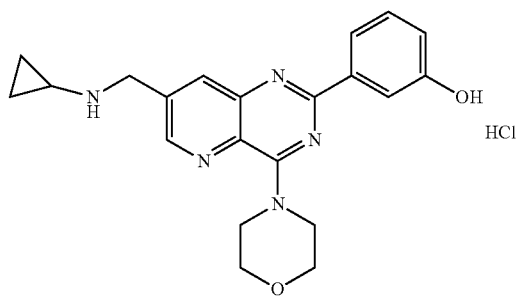
28
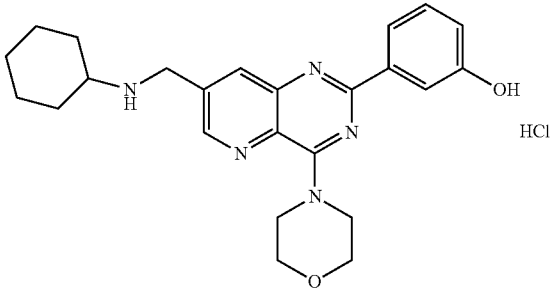
29
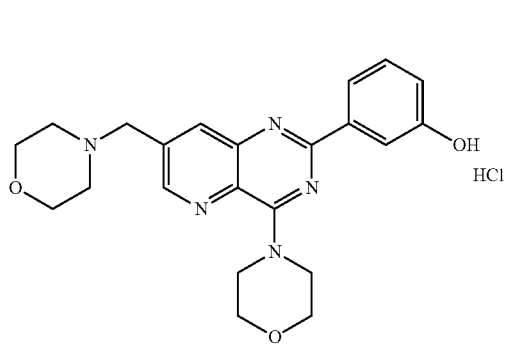
30
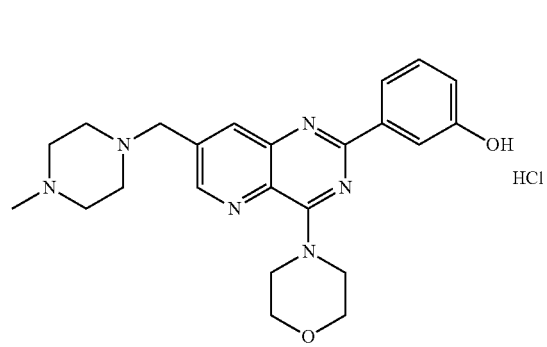
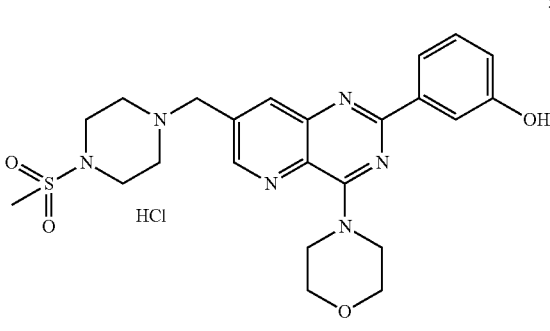

-continued

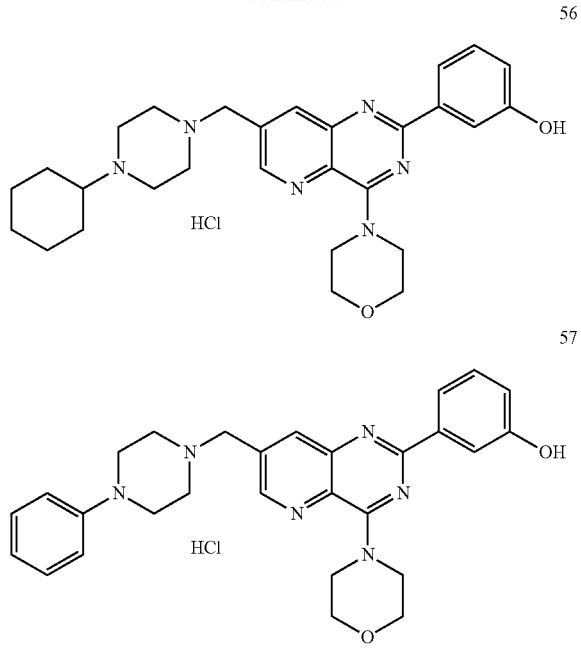

56

57

HCl

HCl

A.5.4. Preparation of Oxime Derivatives and Other Derivatives

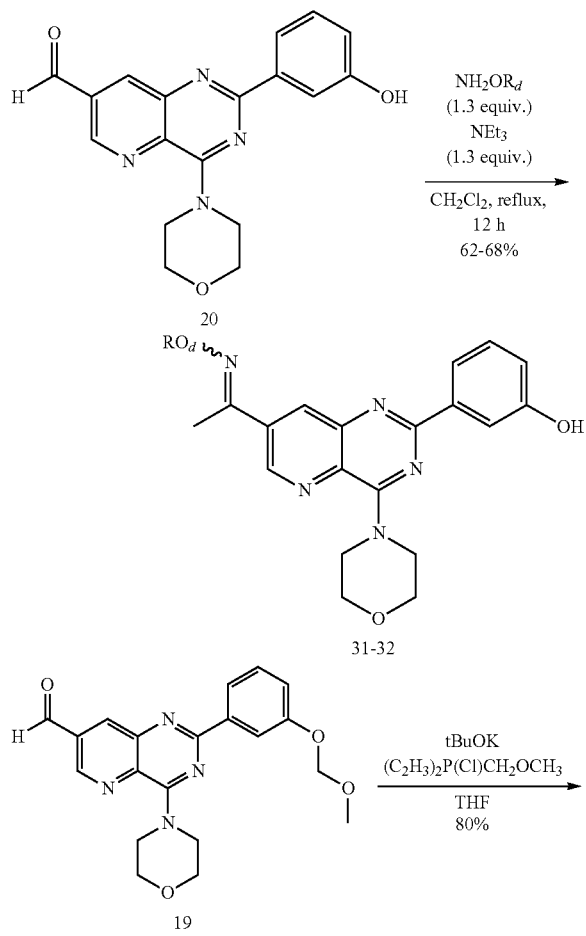

20

31-32

19

-continued

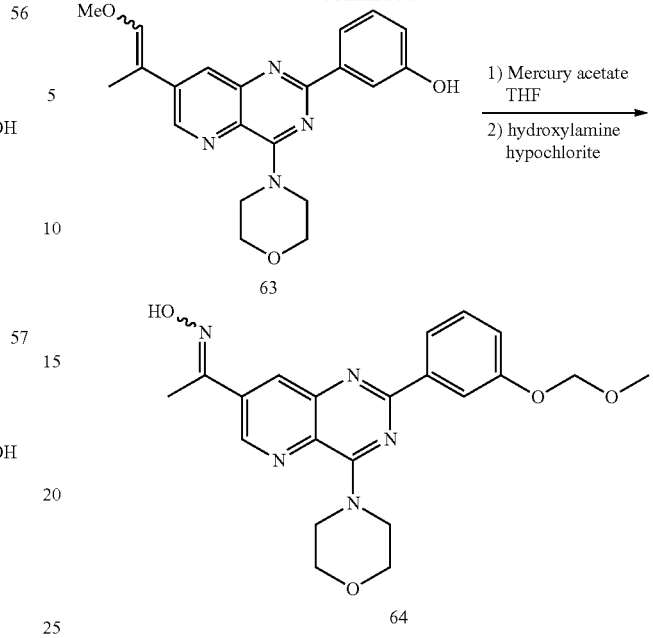

63

64

2-(3-hydroxyphenyl)-4-morphohnopyrido[3,2-d]pyrimidine-7-carbaldehyde oxime (31):

In a 25 mL flask, 66 mg (0.196 mmol; 1.0 equiv.) of (20) were dissolved in 6 mL of anhydrous dichloromethane. 16 mg (0.235 mmol; 1.2 equiv.) of hydroxylamine hydrochloride were added as well as 32 µL (0.235 mmol; 1.2 equiv.) of triethylamine. The solution was left with stirring for 12 hours before addition of dichloromethane (40 mL). The reaction medium was washed with an aqueous solution saturated with sodium bicarbonate (10 mL), dried on MgSO$_4$, filtered and then concentrated under reduced pressure in order to obtain a pure white solid as an isomer mixture (Z/E, 85/15) with a yield of 62%. These isomers may be separated by chromatography column on silica gel under pressure (DCM/MeOH, 99/1). MP: 231° C.; Infrared (Diamand ATR, cm$^{-1}$) ν: 3277, 2864, 1736, 1561, 1520, 1434, 1356, 1311, 1234, 1107, 972, 739, 678, $^1$H NMR (400 MHz, DMSO) δ: 3.91-3.69 (m, 4H, 2×CH$_2$(O)), 4.50 (bs, 4H, 2×CH$_2$(N)), 6.90 (dd, 1H, J=1.8 Hz, J=7.7 Hz, H$_{arom}$), 7.30 (t, 1H, J=8.0 Hz, H$_{arom}$), 7.81-7.99 (m, 2H, 2×H$_{arom}$), 8.23 (d, 1H, J=2.0 Hz, H$_8$), 8.40 (s, 1H, H$_{arom}$), 9.00 (d, 1H, J=2.0 Hz, H$_6$), 9.54 (d, 1H, J=5.7 Hz, OH), 11.92 (s, 1H, CNH); $^{13}$C NMR (101 MHz, DMSO) δ: 47.3 (2×CH$_2$), 66.4 (2×CH$_2$), 114.9 (CH), 117.6 (CH), 119.0 (CH), 129.3 (CH), 132.1 (Cq), 132.3 (Cq), 133.5 (CH), 139.1 (Cq), 143.5 (CH), 145.7 (CH), 147.6 (Cq), 157.4 (Cq), 158.4 (Cq), 159.3 (Cq); HRMS (EI-MS): C$_{18}$H$_{17}$N$_5$O$_3$[M+H]$^+$, calculated m/z 352.1331. found m/z 352.1407.

2-(3-hydroxyphenyl)-4-morphohnopyrido[3,2-d]pyrimidine-7-carbaldehyde O-methyloxime (32): In a 25 mL flask, 60 mg (0.178 mmol; 1.0 equiv.) of (20) were dissolved in 6 mL of anhydrous dichloromethane. 20 mg (0.232 mmol; 1.3 equiv.) of methoxyamine hydrochloride was added as well as 31 µL (0.232 mmol; 1.3 equiv.) of triethylamine. The solution was left with stirring for 12 hours with reflux, before additional adding of dichloromethane (40 mL). The reaction medium was washed with an aqueous solution saturated with sodium bicarbonate (10 mL), dried on MgSO$_4$, filtered and then concentrated under reduced pressure in order to obtain a pure white solid in the form of an isomer mixture (Z/E, 90/10) with a yield of 68%. These isomers may be separated by a chromatography column on silica gel under pressure (DCM/MeOH, 99/1). MP: 244° C.; Infrared (Diamand ATR, cm$^{-1}$) ν: 3040, 2962, 1517, 1442, 1348, 1148, 1115, 1054, 927, 743, 674, $^1$H NMR (400 MHz, DMSO) δ: 3.83 (d, 4H, J=4.1 Hz, 2×CH$_2$(O)), 4.00 (s, 3H, CH$_3$), 4.50 (s, 4H, 2×CH$_2$(N)), 6.90 (d, 1H, J=8.1 Hz, H$_{arom}$), 7.30 (t, 1H, J=8.1 Hz, H$_{arom}$), 7.88 (s, 2H, 2×H$_{arom}$), 8.28 (s, 1H, H$_8$), 8.49 (s, 1H, H$_{oxime}$), 8.97 (s, 1H, H$_6$), 9.55 (s, 1H, OH); $^{13}$C NMR (101 MHz, DMSO) δ: 48.7 (2×CH$_2$), 62.3 (CH$_3$), 66.3 (2×CH$_2$), 114.9 (CH), 117.7 (CH), 119.0 (CH), 121.1 (Cq), 129.3 (CH), 131.1 (Cq), 132.4 (Cq), 134.2 (Cq), 143.6 (CH), 146.2 (CH), 157.4 (Cq), 158.4 (Cq), 159.3 (Cq), 164.8 (CH); HRMS (EI-MS): C$_{19}$H$_{19}$N$_5$O$_3$ [M+H]$^+$, calculated m/z 366.1561. found m/z 366.1564.

4-[7-(2-methoxyethenyl)-2-[3-(methoxymethoxy)phenyl] pyrido[3,2-d]pyrimidin-4 yl]morpholine (63): Under an inert atmosphere, in a 100 mL flask, 665.0 mg (1.94 mmol; 1.5 equiv.) of methoxymethyltriphenylphosphonium chloride were suspended in 15 mL of tetrahydrofurane (THF). At 0° C., 1.94 mL (C=1 M, 1.94 mmol, 1.5 equiv.) of potassium tert-butoxide were added. After 1 h at 0° C., the aldehyde (19) (1.29 mmol, 1 equiv.) solubilized in 15 mL of THF was added drop wise. Water (30 mL) was also added after 48 h at room temperature. The organic phase was extracted three times with ethyl acetate (10 mL), washed with a saturated saline solution, dried on MgSO$_4$, filtered and then concentrated under reduced pressure. The crude residue was then purified by a chromatography column on silica gel under pressure (AE/EP 2/8) allowing isolation of a mixture with a configuration of E/Z (1/1) as a colourless oil with a yield of 80%; Infrared (Diamand ATR, cm$^{-1}$) ν: 3293, 2856, 1528, 1495, 1442, 1352, 1111, 1021, 861, 739; $^1$H NMR (400 MHz, CDCl$_3$) δ: 3.55 (s, 3H, CH$_3$), 3.80 (s, 3H, CH$_3$ of E), 3.92 (s, 2H, CH$_3$ of Z), 3.94 (m, 4H, 2×CH$_2$(O)), 4.48 (s, 4H, 2×CH$_2$(N)), 5.30 (s, 2H, CH$_2$), 5.37 (d, 1H, J=6.8 Hz, CH of Z), 5.90 (d, 1H, J=13 Hz, CH of E), 6.45 (d, 1H, J=6.8 Hz, CH of Z), 7.35 (d, 1H, J=13 Hz, CH of E), 7.41 (t, 1H, J=8.1 Hz, H$_{arom}$), 7.95 (d, 1H, J=1.9 Hz, H$_8$ of E), 8.17 (m, 2H, 2×H$_{arom}$), 8.42 (d, 1H, J=1.9 Hz, H$_8$ of Z), 8.58 (d, 1H, J=1.9 Hz, H$_6$ of E), 8.77 (d, 1H, H$_6$ of Z); $^{13}$C NMR (101 MHz, CDCl$_3$) δ: 48.0 (2×CH$_2$), 56.08 (CH$_3$), 57.22 (OCH$_3$), 61.29 (OCH$_3$), 67.3 (2×CH$_2$), 94.5 (2×CH$_2$), 100.9 (CH of E), 101.1 (CH of Z) and 110.4 (Cq), 116.2 and 116.3 (CH), 117.9 and 118.0 (CH), 119.8 (CH), 129.1 (CH), 130.4 and 130.8 (Cq), 133.6 (CH), 135.4 and 135.9 (Cq) 147.8 and 148.4 (Cq), 148.2 and 146.3 (CH) 152.1 (CH of Z), 152.2 (CH of E) 157.3 and 157.4 (Cq), 158.1 and 159.2 (Cq), 159.6 and 159.9 (Cq); HRMS (EI-MS): C$_{22}$H$_{25}$N$_4$O$_4$ [M+H]$^+$, calculated m/z 409.1876. found m/z 409.1870.

N-(2-{2-[3-(methoxymethoxy)phenyl]-4-(morpholin-4-yl)pyrido[3,2-d]pyrimidin-7-yl}ethylidene)hydroxylamine (64): In a 100 mL flask, 342 mg (0.838 mmol; 1 equiv.) of (19) were solubilized in 15 mL of tetrahydrofurane (THF) and 5 mL of water. At 0° C., 800 mg (2.51 mmol, 3 equiv.) of mercury acetate were added. After 2 h at 0° C., a saline solution (30 mL) was added. The organic phase was extracted three times with ethyl acetate (10 mL), dried on MgSO$_4$, filtered and then concentrated under reduced pressure. The crude residue was solubilized in 40 mL of anhydrous DCM under an inert atmosphere. 112 mg (1.62 mmol, 2 equiv.) of hydroxylamine hypochlorite and 337.7 μL (2.43 mmol, 4 equiv.) of triethylamine were then added. After one night at room temperature, an aqueous solution saturated with NaHCO$_3$ (10 mL) was added. The organic phase was extracted three times with DCM (30 mL), dried on MgSO$_4$, filtered and then concentrated under reduced pressure. The residue was purified by a chromatography column on silica gel under pressure (AE/EP 1/1) allowing isolation of a yellowish solid with a yield of 45%, corresponding to a mixture of isomers (E/Z 1/1). MP: 154° C.; Infrared (Diamand ATR, cm$^{-1}$) ν: 3200, 2911, 1701, 1640, 1508, 1461, 1426, 1268, 1154, 1116, 1071, 1008, 957, 739; $^1$H NMR (400 MHz, CDCl$_3$) δ: 3.52 (s, 3H, CH$_3$), 3.72 (d, J=6.1 Hz, CH$_2$ of E), 3.92 (m, 6H, CH$_2$ of Z and 2×CH$_2$(O)), 4.60 (bs, 4H, 2×CH$_2$(N)), 5.28 (s, 2H, CH$_2$), 6.88 (t, J=5.5 Hz, 1H, CH$_{oxime}$), 7.18 (m, 1H, H$_{arom}$), 7.40 (t, J=7.5 Hz, H$_{arom}$), 7.62 (t, J=6.1 Hz, 1H, CH$_{oxime}$), 8.12 (m, 4H, H$_8$ of E and Z and 2×H$_{arom}$), 8.56 (d, J=2 Hz, 1H, H$_6$ of Z), 8.58 (d, J=2 Hz, 1H, H$_6$ of E), 8.85 (bs, 1H, OH); $^{13}$C NMR (101 MHz, CDCl$_3$) δ: 28.8 (CH$_2$ of Z), 33.3 (CH$_2$ of E), 48.4 (2×CH$_2$), 55.9 (CH$_3$), 66.6 (2×CH$_2$), 94.6 (CH$_2$), 115.7 (CH), 118.5 (CH), 122.8 (CH), 129.6 (CH), 131.9 (Cq), 135.1 (CH), 136.2 (Cq), 139.8 (Cq), 146.9 (CH), 147.0 (Cq), 148.3 (CH of E), 148.7 (CH of Z), 157.4 (Cq), 159.2 (Cq), 160.2 (Cq); HRMS (EI-MS): C$_{21}$H$_{24}$N$_5$O$_4$ [M+H]$^+$, calculated m/z 410.1828. found m/z 410.1823.

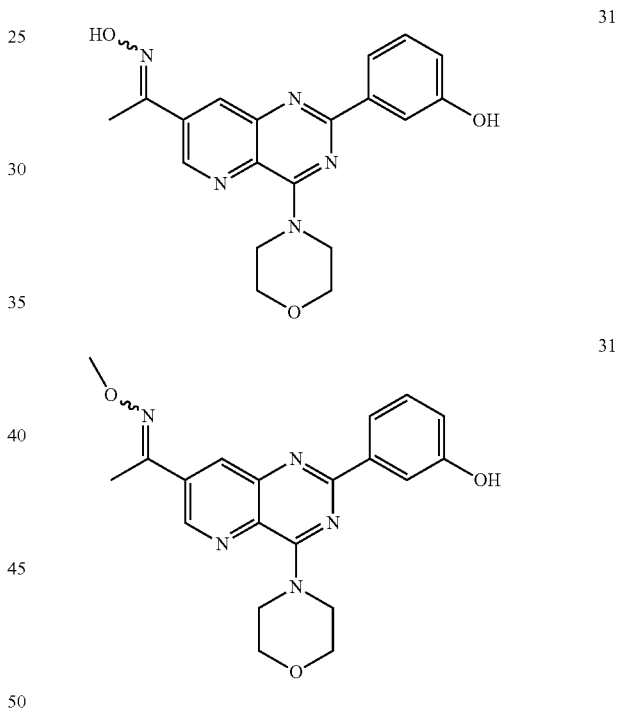

31

31

A.5.5. Reduction and Functionalization in Position C-7

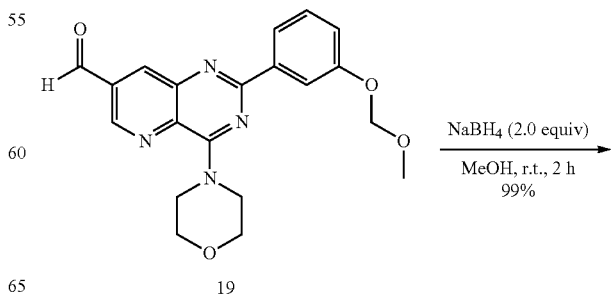

19

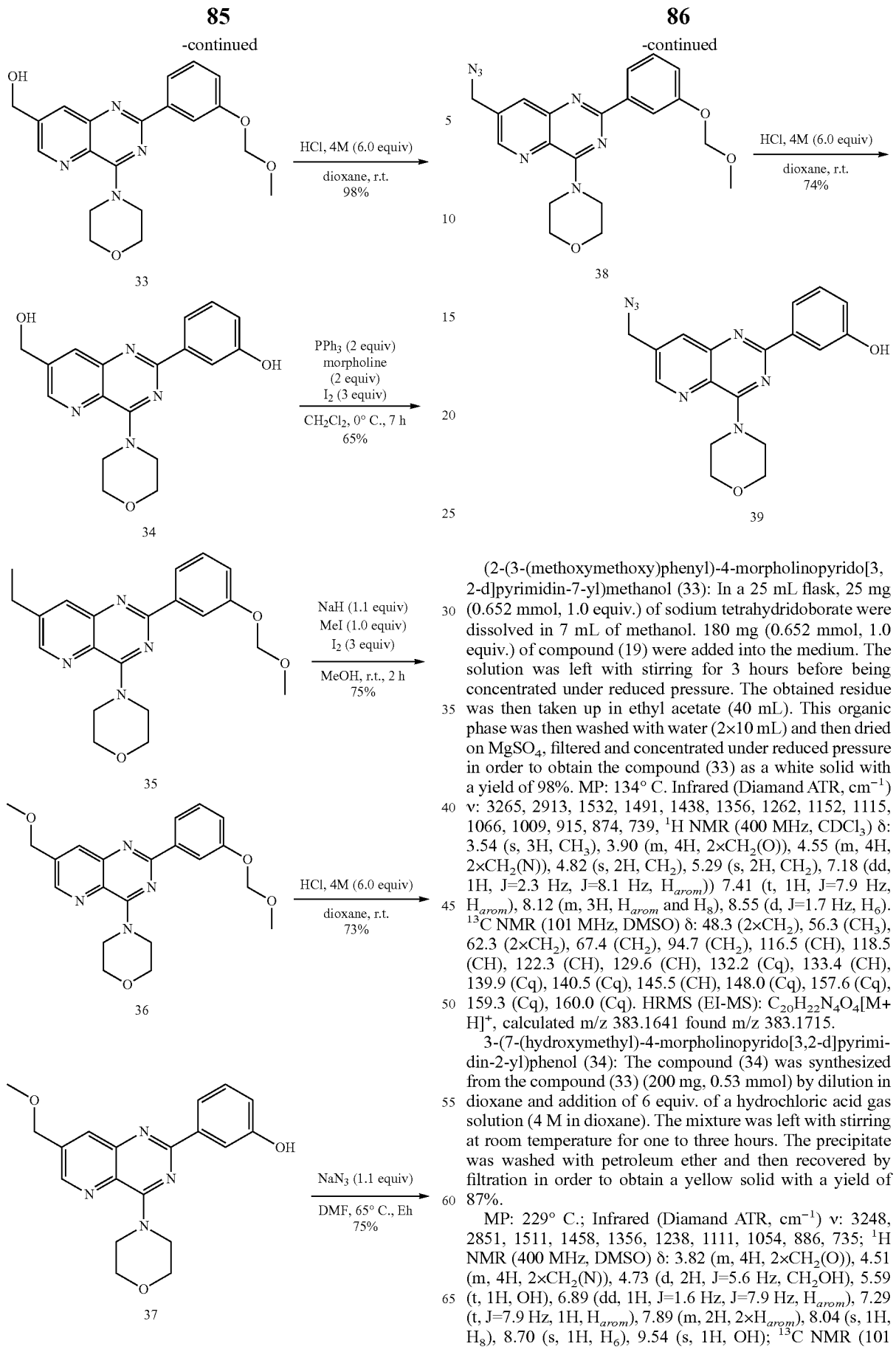

(2-(3-(methoxymethoxy)phenyl)-4-morpholinopyrido[3,2-d]pyrimidin-7-yl)methanol (33): In a 25 mL flask, 25 mg (0.652 mmol, 1.0 equiv.) of sodium tetrahydridoborate were dissolved in 7 mL of methanol. 180 mg (0.652 mmol, 1.0 equiv.) of compound (19) were added into the medium. The solution was left with stirring for 3 hours before being concentrated under reduced pressure. The obtained residue was then taken up in ethyl acetate (40 mL). This organic phase was then washed with water (2×10 mL) and then dried on MgSO$_4$, filtered and concentrated under reduced pressure in order to obtain the compound (33) as a white solid with a yield of 98%. MP: 134° C. Infrared (Diamand ATR, cm$^{-1}$) ν: 3265, 2913, 1532, 1491, 1438, 1356, 1262, 1152, 1115, 1066, 1009, 915, 874, 739, $^1$H NMR (400 MHz, CDCl$_3$) δ: 3.54 (s, 3H, CH$_3$), 3.90 (m, 4H, 2×CH$_2$(O)), 4.55 (m, 4H, 2×CH$_2$(N)), 4.82 (s, 2H, CH$_2$), 5.29 (s, 2H, CH$_2$), 7.18 (dd, 1H, J=2.3 Hz, J=8.1 Hz, H$_{arom}$)) 7.41 (t, 1H, J=7.9 Hz, H$_{arom}$), 8.12 (m, 3H, H$_{arom}$ and H$_8$), 8.55 (d, J=1.7 Hz, H$_6$). $^{13}$C NMR (101 MHz, DMSO) δ: 48.3 (2×CH$_2$), 56.3 (CH$_3$), 62.3 (2×CH$_2$), 67.4 (CH$_2$), 94.7 (CH$_2$), 116.5 (CH), 118.5 (CH), 122.3 (CH), 129.6 (CH), 132.2 (Cq), 133.4 (CH), 139.9 (Cq), 140.5 (Cq), 145.5 (CH), 148.0 (Cq), 157.6 (Cq), 159.3 (Cq), 160.0 (Cq). HRMS (EI-MS): C$_{20}$H$_{22}$N$_4$O$_4$[M+H]$^+$, calculated m/z 383.1641 found m/z 383.1715.

3-(7-(hydroxymethyl)-4-morpholinopyrido[3,2-d]pyrimidin-2-yl)phenol (34): The compound (34) was synthesized from the compound (33) (200 mg, 0.53 mmol) by dilution in dioxane and addition of 6 equiv. of a hydrochloric acid gas solution (4 M in dioxane). The mixture was left with stirring at room temperature for one to three hours. The precipitate was washed with petroleum ether and then recovered by filtration in order to obtain a yellow solid with a yield of 87%.

MP: 229° C.; Infrared (Diamand ATR, cm$^{-1}$) ν: 3248, 2851, 1511, 1458, 1356, 1238, 1111, 1054, 886, 735; $^1$H NMR (400 MHz, DMSO) δ: 3.82 (m, 4H, 2×CH$_2$(O)), 4.51 (m, 4H, 2×CH$_2$(N)), 4.73 (d, 2H, J=5.6 Hz, CH$_2$OH), 5.59 (t, 1H, OH), 6.89 (dd, 1H, J=1.6 Hz, J=7.9 Hz, H$_{arom}$), 7.29 (t, J=7.9 Hz, 1H, H$_{arom}$), 7.89 (m, 2H, 2×H$_{arom}$), 8.04 (s, 1H, H$_8$), 8.70 (s, 1H, H$_6$), 9.54 (s, 1H, OH); $^{13}$C NMR (101

MHz, DMSO) δ: 47.6 (2×CH$_2$), 60.3 (CH$_2$), 66.4 (2×CH$_2$), 114.8 (CH), 117.5 (CH), 119.0 (CH), 129.3 (CH), 131.1 (Cq), 132.5 (CH), 139.3 (Cq), 142.2 (Cq), 145.8 (CH), 147.6 (Cq), 157.4 (Cq), 158.5 (Cq), 158.8 (Cq); HRMS (EI-MS): C$_{18}$H$_{18}$N$_4$O$_3$ [M+H]$^+$, calculated m/z 339.1379. found m/z 339.1441.

4-(7-(iodomethyl)-2-(3-(methoxymethoxy)phenyl)pyrido[3,2-d]pyrimidin-4-yl)morpholine (35): In a 25 mL flask, 110 mg (0.418 mmol; 2 equiv.) of triphenylphosphine were dissolved in 5 mL of anhydrous dichloromethane. 159 mg (0.628 mmol; 3 equiv.) of di-iodine and 29 mg (0.418 mmol; 2 equiv.) of imidazole were added to the mixture. The solution was then cooled to 0° C. by means of an ice bath and 80 mg (0.209 mmol; 1 equiv.) of (33) were added. The reaction medium was stirred at 0° C. for 7 hours. 8 mL of an aqueous solution of Na$_2$S$_2$O$_3$ (10%) were added and after 15 minutes of stirring, the mixture was diluted in 30 mL of dichloromethane. The organic phase was washed with water (2×10 mL), dried on MgSO$_4$, filtered and then concentrated under reduced pressure. The residue was then purified by chromatography on silica gel under pressure (AcOEt/EP, 1/9) in order to obtain a yellow solid with a yield of 76%. MP: 144° C.; Infrared (Diamand ATR, cm$^{-1}$) ν: 2921, 1732, 1663, 1532, 1491, 1430, 1270, 1234, 1148, 1107, 1021, 964, 874, 739; $^1$H NMR (400 MHz, CDCl$_3$) δ: 3.53 (s, 3H, CH$_3$), 3.92 (m, 4H, 2×CH$_2$(O)), 4.53 (s, 2H, CH$_2$I), 4.58 (s, 4H, 2×CH$_2$(N)), 5.28 (s, 2H, CH$_2$), 7.17 (m, 1H, H$_{arom}$), 7.40 (t, 1H, J=7.9 Hz, H$_{arom}$), 8.17-8.10 (m, 3H, 2×H$_{arom}$ and H$_8$), 8.66 (d, 1H, J=2.3 Hz, H$_6$); $^{13}$C NMR (101 MHz, CDCl$_3$) δ: 48.3 (2×CH$_2$), 56.3 (CH3), 62.4 (CH$_2$), 67.4 (2×CH$_2$), 94.8 (CH$_2$), 116.5 (CH), 118.5 (CH), 122.4 (CH), 129.6 (CH), 132.2 (Cq), 133.4 (CH), 135.40 (Cq), 140.0 (Cq), 145.5 (CH), 148.0 (Cq), 157.6 (Cq), 159.3 (Cq), 160.0 (Cq); HRMS (EI-MS): C$_{20}$H$_{21}$IN$_4$O$_3$[M+H]$^+$, calculated m/z 493.0658 found m/z 493.0738.

3-(7-methoxy-4-morpholinopyrido[3,2-d]pyrimidin-2-yl)phenol (37): In a 25 mL flask, 80 mg (0.209 mmol; 1 equiv.) of (33) were dissolved in 7 mL of anhydrous tetrahydrofurane. The solution was cooled to 0° C. by means of an ice bath, and 8 mg (0.23 mmol; 1.1 equiv.) of NaH (60% by mass in oil) were added to the medium. 13 μL (0.209 mmol; 1.0 equiv.) of iodomethane were then added. After 10 minutes of stirring at 0° C., the ice bath was removed and the reaction mixture was then left with stirring for 2 hours 30 minutes at room temperature. After concentration under reduced pressure, the residual crude was taken up in dichloromethane (40 mL), the organic phase was washed with an aqueous solution saturated with NaCl (2×8 mL), dried on MgSO$_4$, filtered and then concentrated under reduced pressure.

The step for deprotection of the MOM was directly carried out with the reaction intermediate (36) by dilution in dioxane and addition of 6 equiv. of a hydrochloric acid gas solution (4 M in dioxane). The mixture was left with stirring at room temperature for one to three hours. The precipitate was washed with petroleum ether and then recovered by filtration in order to obtain the pure compound with a yield of 74% as a yellow solid. MP: 165-166° C.; Infrared (Diamand ATR, cm$^{-1}$) ν: 3273, 2852, 1540, 1491, 1438, 1352, 1270, 1103, 1021, 968, 878, 739, 678, $^1$H NMR (400 MHz, CDCl$_3$) δ: 3.46 (s, 3H, CH$_3$), 3.92 (m, 4H, 2×CH$_2$(O)), 4.58 (m, 4H, 2×CH$_2$(N)), 4.63 (s, 2H, CH$_2$), 6.94 (dd, 1H, J=2.2 Hz, J=7.7 Hz, H$_{arom}$), 7.38 (t, 1H, J=7.9 Hz, H$_{arom}$), 7.98 (m, 1H, H$_{arom}$), 8.02 (d, 1H, J=7.9 Hz, H$_{arom}$), 8.10 (m, 1H, H$_8$), 8.65 (d, J=2.1 Hz, H$_6$); $^{13}$C NMR (101 MHz, CDCl$_3$) δ: 48.3 (2×CH2), 58.9 (CH$_3$), 67.5 (2×CH$_2$), 72.0 (CH$_2$), 115.5 (CH), 117.9 (CH), 121.1 (CH), 129.8 (CH), 132.5 (Cq), 134.5 (CH), 137.7 (Cq), 140.1 (Cq), 146.1 (CH), 148.1 (Cq), 156.2 (Cq), 159.4 (Cq), 160.3 (Cq); HRMS (EI-MS): C$_{18}$H$_{20}$N$_4$O$_3$ [M+H]$^+$, calculated m/z 353.1535 found m/z 353.1609.

4-(7-(azidomethyl)-2-(3-(methoxymethoxy)phenyl)pyrido[3,2-d]pyrimidin-4-yl)morpholine (38): In a 25 mL flask, 78 mg (0.158 mmol; 1 equiv.) of (33) were diluted in 6 mL of dimethylformamide dried on a 4 Å sieve, as well as 15 mg (0.238 mmol; 1.5 equiv.) of sodium nitride. The mixture was heated to 65° C. for 6 hours. After returning to room temperature, 60 mL of dichloromethane were added. The resulting organic phase was washed with an aqueous solution of 10% citric acid (10 mL), with an aqueous solution saturated with NaHCO$_3$ (10 mL) and with water (2×10 mL). The organic phase was then dried on MgSO$_4$, filtered and then concentrated under reduced pressure. The compound (38) was obtained after purification by chromatography column on silica gel under pressure (DCM/MeOH, 98/2) with a yield of 75% as a yellow solid. MP: 143° C.; Infrared (Diamand ATR, cm$^{-1}$) ν: 2872, 2086, 1612, 1523, 1428, 1307, 1109, 1021, 862, 731; $^1$H NMR (400 MHz, CDCl$_3$) δ: 3.53 (s, 3H, CH$_3$), 3.88 (m, 4H, 2×CH$_2$(O)), 4.68 (bs, 4H, 2×CH$_2$(N)), 4.90 (s, 2H, CH$_2$N$_3$), 5.28 (s, 2H, CH$_2$), 7.08 (m, 1H, H$_{arom}$), 7.41 (m, 1H, H$_{arom}$), 7.87 (m, 2H, 2×H$_{arom}$), 8.46 (s, 1H, H$_8$), 8.91 (s, 1H, H$_6$); $^{13}$C NMR (101 MHz, CDCl$_3$) δ: 48.4 (2×CH$_2$), 50.4 (CH$_2$), 56.3 (CH$_3$), 66.3 (2×CH$_2$), 94.7 (CH$_2$), 115.5 (CH), 119.6 (2×CH), 130.0 (CH), 132.2 (Cq), 134.8 (Cq), 137.8 (CH), 140.2 (Cq), 147.5 (CH), 149.2 (Cq), 157.8 (Cq), 159.5 (Cq), 160.3 (Cq); HRMS (EI-MS): C$_{20}$H$_{21}$N$_7$O$_3$ [M+H]$^+$, calculated m/z 408.1706 found m/z 408.1803.

3-(7-(azidomethyl)-4-morpholinopyrido[3,2-d]pyrimidin-2-yl)phenol (39): The compound (9) was synthesized from the compound (38) (50 mg, 0.123 mmol) by dilution in dioxane and addition of 6 equiv. of a hydrochloric acid gas solution (4 M in dioxane). The mixture was left with stirring at room temperature for one to three hours. The precipitate was washed with petroleum ether and then recovered by filtration in order to obtain a yellow solid with a yield of 98%. MP: 169° C.; Infrared (Diamand ATR, cm$^{-1}$) ν: 3383, 3043, 2868, 2096, 1613, 1552, 1511, 1434, 1307, 1111, 1021, 862, 731, 670; $^1$H NMR (400 MHz, CDCl$_3$) δ: 3.89 (m, 4H, 2×CH$_2$(O)), 4.70 (bs, 4H, 2×CH$_2$(N)), 4.89 (s, 2H, CH$_2$N$_3$), 7.12 (m, 1H, H$_{arom}$), 7.43 (m, 1H, H$_{arom}$), 7.87 (m, 2H, 2×H$_{arom}$), 8.49 (s, 1H, H$_8$), 8.87 (s, 1H, H$_6$), 10.06 (bs, 1H, OH); $^{13}$C NMR (101 MHz, CDCl$_3$) δ: 48.4 (2×CH$_2$), 50.4 (CH$_2$), 66.3 (2×CH$_2$), 115.4 (CH), 119.6 (2×CH), 130.0 (CH), 132.7 (Cq), 133.8 (Cq), 137.4 (CH), 139.9 (Cq), 146.9 (CH), 148.8 (Cq), 157.8 (Cq), 159.1 (Cq), 160.0 (Cq); HRMS (EI-MS): C$_{18}$H$_{17}$N$_7$O$_2$[M+H]$^+$, calculated m/z 363.1444 found m/z 364.1517.

A.5.6. Preparation of Nitrile Derivatives in Position C7

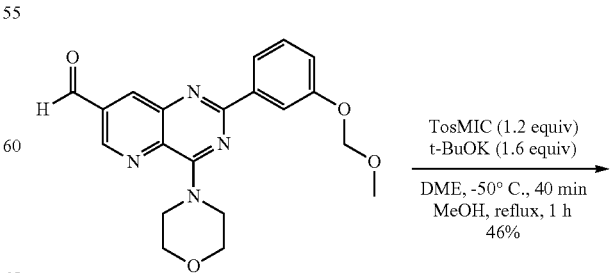

19

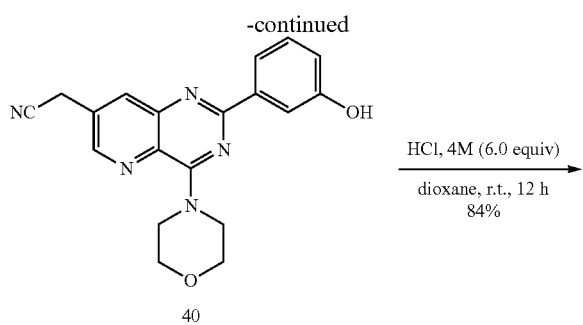

2-(2-(3-(methoxymethoxy)phenyl)-4-morpholinopyrido[3,2-d]pyrimidin-7-yl)acetonitrile (40): Under an inert atmosphere in a 25 mL flask, 108 mg (0.962 mmol; 1.6 equiv.) of t-BuOK were dissolved in 4 mL of anhydrous dimethoxyethane, at −50° C. A solution containing 141 mg (0.722 mmol; 1.2 equiv.) of toluenesulfonylmethyl isonitrile in anhydrous dimethoxyethane (4 mL) was added drop wise. After 10 min of stirring at −50° C., a solution of 230 mg (0.602 mmol; 1.0 equiv.) of 2(19) in 4 mL of anhydrous dimethoxyethane, was added drop wise. The reaction mixture was then left with stirring for 40 minutes. Methanol (5 mL) was then added to the reaction mixture before refluxing it for 1 hour. After concentration under reduced pressure, the residue was taken up in ethyl acetate (30 mL). The organic phase was washed with water (2×10 mL), dried on MgSO$_4$, filtered and then concentrated under reduced pressure. The expected compound (40) was obtained after purification by chromatography column on silica gel under pressure (DCM/MeOH, 99.4/0.6) with a yield of 46% as a white solid. MP: 158° C.; Infrared (Diamand ATR, cm$^{-1}$) ν: 2952, 2259, 1600, 1553, 1524, 1502, 1435, 1350, 1271, 1150, 1112, 1078, 1017, 967, 916, 875, 736, 685; $^1$H NMR (400 MHz, CDCl$_3$) δ: 3.56 (s, 3H, CH$_3$), 3.95 (t, 6H, J=4.8 Hz, CH$_2$CN and 2×CH$_2$(O)), 4.61 (s, 4H, 2×CH$_2$(N)), 5.31 (s, 2H, CH$_2$), 7.20 (ddd, 1H, J=1.1 Hz, J=2.5 Hz, J=8.1 Hz, H$_{arom}$), 7.43 (t, 1H, J=7.9 Hz, H$_{arom}$), 8.16 (dd, 3H, J=1.2 Hz, J=7.8 Hz, H$_{arom}$ and H$_8$), 8.62 (d, 1H, J=2.3 Hz, H$_6$); $^{13}$C NMR (101 MHz, CDCl$_3$) δ: 21.6 (CH$_2$), 48.3 (2×CH$_2$), 56.3 (CH$_3$), 67.4 (2×CH$_2$), 94.7 (CH$_2$), 116.6 (CH), 118.6 (CH), 122.4 (CH), 129.5 (CH), 129.6 (Cq), 132.9 (Cq), 135.6 (CH), 139.8 (Cq), 145.0 (CH), 148.1 (Cq), 157.6 (Cq), 159.2 (Cq), 160.6 (Cq); HRMS (EI-MS): C$_{21}$H$_{21}$N$_5$O$_3$ [M+H]$^+$, calculated m/z 392.1644 found m/z 392.1718.

2-(2-(3-hydroxyphenyl)-4-morpholinopyrido[3,2-d]pyrimidin-7-yl)acetonitrile (41): The compound (41) was synthesized from the compound (40) (70 mg, 0.179 mmol) by dilution in dioxane and addition of 6 equiv. of a hydrochloric acid gas solution (4 M in dioxane). The mixture was left with stirring at room temperature for one to three hours. The precipitate was washed with petroleum ether and then recovered by filtration in order to obtain a white solid with a yield of 84%. MP: 201° C.; Infrared (Diamand ATR, cm$^{-1}$) ν: 3402, 2930, 2246, 1616, 1556, 1505, 1439, 1385, 1318, 1245, 1116, 1024, 865, 732; $^1$H NMR (400 MHz, CDCl$_3$) δ: 3.87 (s, 4H, 2×CH$_2$(O)), 4.44 (s, 2H, CH$_2$), 4.66 (bs, 4H, 2×CH$_2$(N)), 7.08 (d, 1H, J=8.0 Hz, H$_{arom}$), 7.41 (t, 1H, J=7.9 Hz, H$_{arom}$), 8.04-7.76 (m, 2H, H$_{arom}$ and H$_8$), 8.46 (s, 1H, H$_{arom}$), 8.82 (d, 1H, J=2.0 Hz, H$_6$), 9.85 (s, 1H, OH); $^{13}$C NMR (101 MHz, CDCl$_3$) δ: HRMS (EI-MS): C$_{19}$H$_{17}$N$_5$O$_2$ [M+H]$^+$, calculated m/z 348.1382 found m/z 348.1455.

A.5.7. Preparation of Carboxylic Acid Derivatives in Position C7

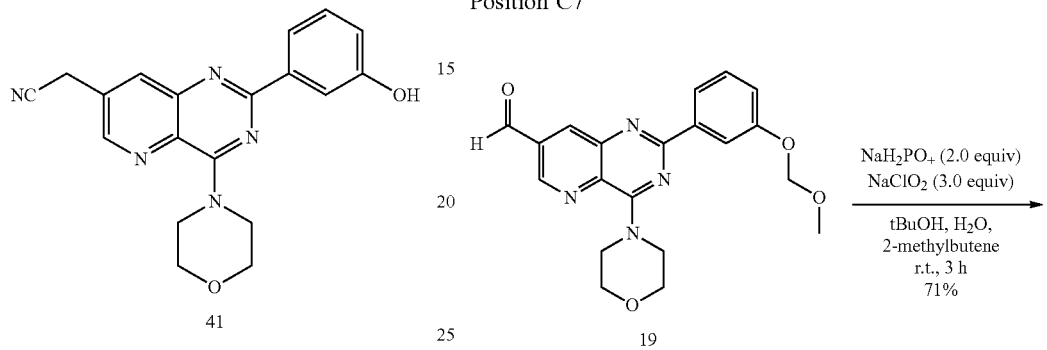

2-(3-hydroxyphenyl)-4-morpholinopyrido[3,2-d]pyrimidine-7-carboxylic acid (42): In a 50 mL flask, 150 mg (0.39 mmol; 1.0 equiv.) of the compound (19) were dissolved in a THF/t-BuOH/2-methylbutene mixture, (10/11/3 mL). An aqueous solution (4 mL) containing 123 mg (0.79 mmol; 2.0 equiv.) of NaH$_2$PO$_4$ and 107 mg (1.12 mmol; 3.0 equiv.) of NaCl$_2$O was added to the reaction medium. The mixture was stirred for three hours at room temperature. 5 mL of a citric acid (10%) solution were added and after stirring for 15 minutes, the mixture was diluted in 30 mL of ethyl acetate. The organic phase was washed with a solution saturated with sodium bicarbonate (10 mL) and then with a solution saturated with sodium chloride (10 mL), the organic extract was dried on MgSO$_4$, filtered and then concentrated under reduced pressure in order to obtain the product as a yellow solid with a yield of 71%. MP: 158° C.; Infrared (Diamand ATR, cm$^{-1}$) ν: 3177, 3048, 2965, 1728, 1619, 1559, 1509, 1193, 882; $^1$H NMR (400 MHz, DMSO) δ: 3.80-3.87 (m, 4H, 2×CH$_2$(O)), 4.69 (bs, 4H, 2×CH$_2$(N)), 7.09 (d, 1H, J=4.9 Hz, H$_{arom}$)) 7.41 (dd, 1H, J=4.9 Hz, J=5.0 Hz, H$_{arom}$), 7.85 (s, 1H, H$_8$), 7.93 (d, 1H, J=4.9 Hz, H$_{arom}$), 8.96 (s, 1H, H$_6$), 9.21 (s, 1H, OH), 9.95 (s, 1H, COOH); $^{13}$C NMR (101 MHz, DMSO) δ: 49.2 (2×CH$_2$), 66.8 (2×CH$_2$), 116.2 (2×CH), 120.3 (CH), 120.6 (CH), 130.4 (2×CH), 130.9 (Cq), 133.1 (Cq), 147.5 (CH), 157.1 (Cq), 157.9 (Cq), 158.3 (2×Cq), 165.1 (2×Cq); HRMS (EI-MS): C$_{18}$H$_{16}$N$_4$O$_4$ [M+H]$^+$, calculated m/z 353.1244. found m/z 353.1246.

A.5.8. Preparation of Triazole Derivatives in Position C7
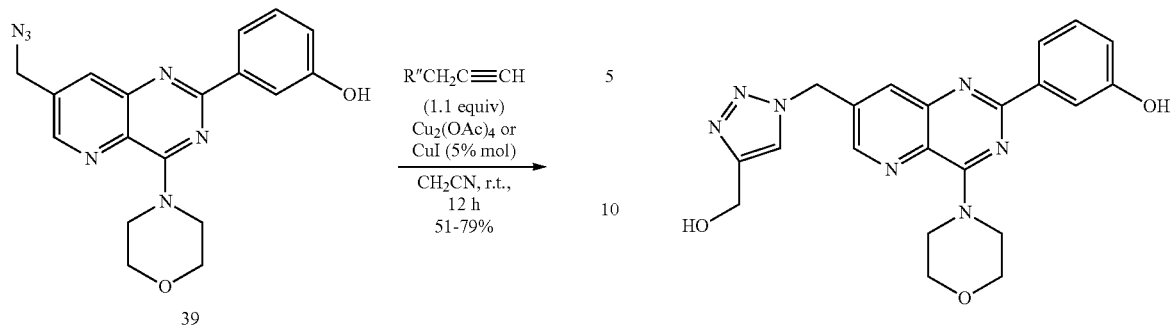
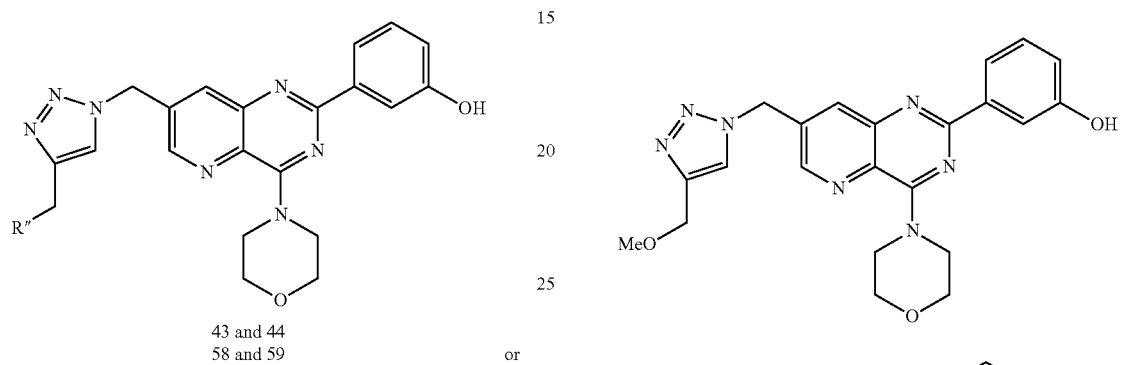
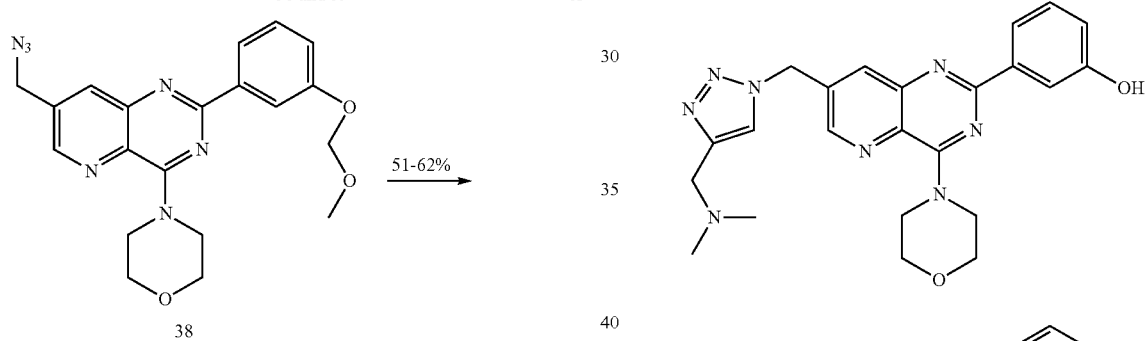
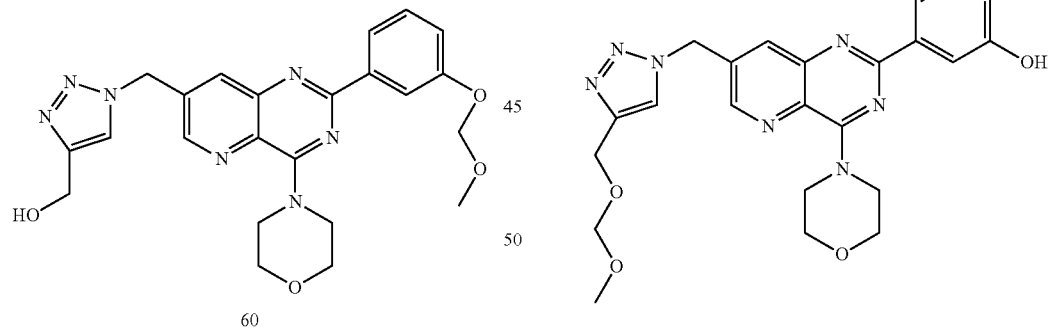
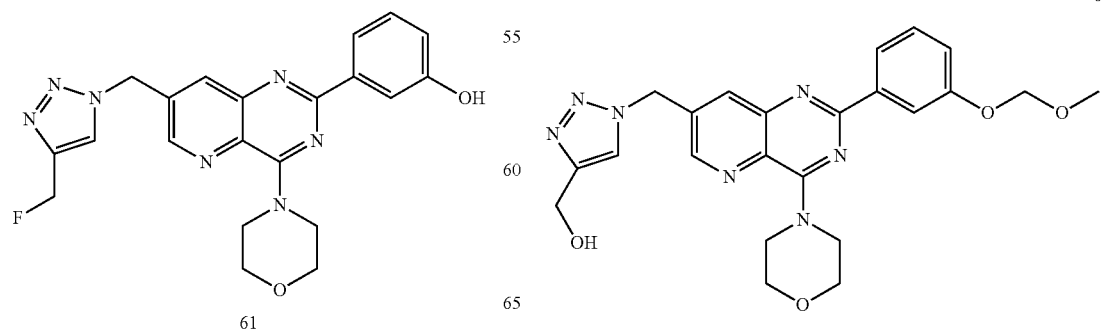

-continued

61

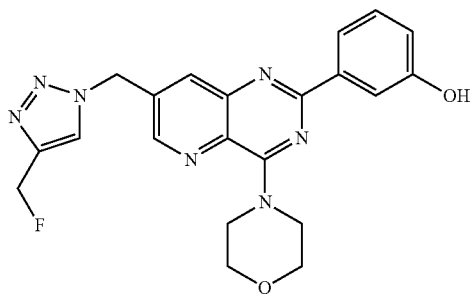

3-(7-((4-(methoxymethyl)-1H-1,2,3-triazol-1-yl)methyl)-4-morpholinopyrido[3,2-d]pyrimidin-2-yl)phenol (43): In a 10 mL flask, 80 mg (0.22 mmol; 1.0 equiv.) of (39) were suspended in 3 mL of acetonitrile. Triethylamine was added drop wise until perfect dissolution of the compound into the solution. Then were added 3 mg (0.011 mmol; 0.05 equiv.) of copper iodide and 19 μL (0.22 mmol, 1 equiv.) of methoxy propargylic ether. The mixture was stirred at room temperature for 12 hours. The solution was diluted in ethyl acetate (30 mL). The organic phase was washed with an aqueous solution saturated with NaHCO$_3$ (10 mL), dried on MgSO$_4$, filtered and then concentrated under reduced pressure. The compound (44) was isolated after purification by chromatography column on silica gel under pressure (DCM/MeOH, 99/1) with a yield of 79%, as a white solid. MP: 241° C.; Infrared (Diamand ATR, cm$^{-1}$) ν: 3130, 2856, 1589, 1552, 1516, 1430, 1315, 1275, 1107, 1062, 1029, 968, 792, 739, 674, $^1$H NMR (400 MHz, CDCl$_3$) δ: 3.28 (s, 3H, CH$_3$), 3.81 (m, 4H, 2×CH$_2$(O)), 4.47 (m, 6H, CH$_2$ and 2×CH$_2$(N)), 5.88 (s, 2H, CH$_2$OCH$_3$), 6.89 (d, 1H, J=7.8 Hz, H$_{arom}$), 7.28 (t, 1H, J=8.0 Hz, H$_{arom}$), 7.87 (d, 2H, J=6.6 Hz, 2×H$_{arom}$), 7.94 (s, 1H, H$_8$), 8.32 (s, 1H, CH), 8.72 (s, 1H, H$_6$), 9.53 (s, 1H, OH); $^{13}$C NMR (101 MHz, CDCl$_3$) δ: 47.6 (2×CH$_2$), 49.9 (CH$_2$), 57.4 (CH), 64.9 (CH$_2$), 66.4 (2×CH$_2$), 114.8 (CH), 117.6 (CH), 119.0 (CH), 124.5 (CH), 129.3 (CH), 131.8 (Cq), 134.5 (CH), 135.8 (Cq), 139.0 (Cq), 144.4 (Cq), 145.9 (CH), 147.3 (Cq), 157.4 (Cq), 158.4 (Cq), 159.2 (Cq); HRMS (EI-MS): C$_{22}$H$_{23}$N$_7$O$_3$[M+H]$^+$, calculated m/z 433.1862 found m/z 434.1939.

3-(7-((4-(hydroxymethyl)-1H-1,2,3-triazol-1-yl)methyl)-4-morpholinopyrido[3,2-d]pyrimidin-2-yl)phenol (44): In a 10 mL flask, 82 mg (0.226 mmol; 1 equiv.) of (39) were suspended in 3 mL of acetonitrile. Triethylamine was added drop wise until perfect dissolution of the compound into the solution. Then were added 3 mg (0.011 mmol; 0.05 equiv.) of copper iodide and 16 μL (0.249 mmol, 1.1 equiv.) of propargyl alcohol. The mixture was stirred at room temperature for 12 hours. The solution was diluted in ethyl acetate (30 mL). The organic phase was washed with an aqueous solution saturated with NaHCO$_3$ (10 mL), dried on MgSO$_4$, filtered and then concentrated under reduced pressure. The crude residue was then purified by chromatography column on silica gel under pressure (DCM/MeOH, 98/2) allowing isolation of a white solid with a yield of 51%. MP: 238° C.; Infrared (Diamand ATR, cm$^{-1}$) ν: 3154, 2962, 2848, 1605, 1556, 1495, 1458, 1348, 1266, 1115, 1025, 886, 739, 678, $^1$H NMR (400 MHz, CDCl$_3$) δ: 3.81 (m, 4H, 2×CH$_2$(O)), 4.50 (s, 4H, 2×CH$_2$(N)), 4.54 (d, 2H, J=5.6 Hz, CH$_2$), 5.20 (t, 1H, J=5.6 Hz, OH), 5.87 (s, 1H, CH$_2$), 6.89 (d, 1H, J=7.8 Hz, H$_{arom}$), 7.28 (t, 1H, J=8.0 Hz, H$_{arom}$), 7.84 (m, 2H, 2×H$_{arom}$), 7.94 (d, 1H, J=2.0 Hz, H$_8$), 8.19 (s, 1H, CH), 8.72 (d, 1H, J=2.0 Hz, H$_6$), 9.53 (s, 1H, OH); $^{13}$C NMR (101 MHz, CDCl$_3$) δ: 47.6 (2×CH$_2$), 49.9 (CH$_2$), 55.0 (CH$_2$), 66.4 (2×CH$_2$), 114.8 (CH), 117.6 (CH), 119.0 (CH), 123.4 (Cq), 129.3 (CH), 131.8 (CH), 134.4 (Cq), 136.0 (Cq), 139.0 (CH), 145.9 (CH), 147.3 (Cq), 148.6 (Cq), 157.4 (Cq), 158.4 (Cq), 159.2 (Cq); HRMS (EI-MS): C$_{21}$H$_{21}$N$_7$O$_3$ [M+H]$^+$, calculated m/z 420.1706 found m/z 420.1784.

3-[7-({4-[(dimethylamino)methyl]-1H-1,2,3-triazol-1-yl}methyl)-4-(morpholin-4-yl)pyrido[3,2-d]pyrimidin-2-yl]phenol (58): Under an inert atmosphere, in a 10 mL flask, 80 mg (0.22 mmol; 1.0 equiv.) of (39) were suspended in 3 mL of acetonitrile. Triethylamine was added drop wise until perfect dissolution of the compound into the solution. Then were added, 25 μL (C=0.4 M; 0.011 mmol; 0.05 equiv.) of copper acetate hydrate and 26 μL (0.22 mmol, 1 equiv.) of 3-dimethylamino-1-propyne. The mixture was stirred at room temperature for 12 hours. The solution was diluted in ethyl acetate (30 mL). The organic phase was washed with an aqueous solution saturated with NaHCO$_3$ (10 mL), dried on MgSO$_4$, filtered and then concentrated under reduced pressure. The compound (58) was triturated with dichloromethane, and then filtered in vacuo, in order to lead to the compound with a yield of 31%, as a yellowish solid. MP: 224° C.; Infrared (Diamond ATR, cm$^{-1}$) ν: 3271, 2856, 1595, 1557, 1508, 1437, 1308, 1269, 1166, 1113, 1062, 1029, 968, 792, 739, 674, $^1$H NMR (400 MHz, DMSO-d$_6$) δ: 2.18 (bs, 6H, 2×CH$_3$); 3.55 (bs, 2H, CH$_2$), 3.83 (m, 4H, 2×CH$_2$(O)), 4.51 (m, 6H, 2×CH$_2$(N)), 5.89 (s, 2H, CH$_2$OCH$_3$), 6.90 (d, 1H, J=7.8 Hz, H$_{arom}$), 7.30 (t, 1H, J=8.0 Hz, H$_{arom}$), 7.87 (d, 2H, J=6.6 Hz, 2×H$_{arom}$), 7.94 (s, 1H, H$_8$), 8.24 (s, 1H, CH), 8.73 (s, 1H, H$_6$), 9.55 (s, 1H, OH); $^{13}$C NMR (101 MHz, DMSO-d$_6$) δ: 45.0 (2×CH$_3$), 48.1 (2×CH$_2$), 50.4 (CH$_2$), 55.9 (CH), 55.4 (CH$_2$), 66.8 (2×CH$_2$), 115.3 (CH), 118.1 (CH), 119.5 (CH), 124.8 (CH), 129.8 (CH), 132.3 (Cq), 135.0 (Cq), 136.3 (Cq), 139.5 (Cq), 144.4 (Cq), 146.4 (CH), 147.8 (Cq), 157.9 (Cq), 158.8 (Cq), 159.6 (Cq); HRMS (EI-MS): C$_{23}$H$_{26}$N$_8$O$_2$ [M+H]$^+$, calculated m/z 447.2257 found m/z 447.2251.

3-[7-({4-[(methoxymethoxy)methyl]-1H-1,2,3-triazol-1-yl}methyl)-4-(morpholin-4-yl)pyrido[3,2-d]pyrimidin-2-yl]phenol (59): Under an inert atmosphere, in a 10 mL flask, 45 mg (0.13 mmol; 1.0 equiv.) of (39) were suspended in 3 mL of acetonitrile. Triethylamine was added drop wise until perfect dissolution of the compound in the solution. Then were added 1.2 mg (0.006 mmol; 0.05 equiv.) of copper iodide and 14 mg (0.14 mmol, 1.1 equiv.) of methoxy(prop-2-yn-1-yloxy)methane. The mixture was stirred at room temperature for 12 hours. The solution was diluted in ethyl acetate (30 mL). The organic phase was washed with an aqueous solution saturated with NaHCO$_3$ (10 mL), dried on MgSO$_4$, filtered and then concentrated under reduced pressure. The crude was triturated with diethyl ether followed by filtration in vacuo which led to the compound with a yield of 25%, as a brown solid. MP: 218° C.; Infrared (Diamand ATR, cm$^{-1}$) ν: 3204, 2937, 1618, 1589, 1552, 1516, 1430, 1315, 1275, 1107, 1062, 1029, 968, 792, 739, 674, $^1$H NMR (400 MHz, CDCl$_3$) δ: 3.29 (s, 3H, CH$_3$), 3.82 (m, 4H, 2×CH$_2$(O)), 4.47 (bs, 2×CH$_2$(N)), 4.61 (s, 2H, CH$_2$), 4.65 (s, 2H, CH$_2$); 5.90 (s, 2H, CH$_2$), 6.89 (d, 1H, J=7.8 Hz, H$_{arom}$)) 7.30 (t, 1H, J=8.0 Hz, H$_{arom}$), 7.88 (d, 2H, J=6.6 Hz, 2×H$_{arom}$), 7.96 (s, 1H, H$_8$), 8.35 (s, 1H, CH), 8.74 (s, 1H, H$_6$), 9.55 (s, 1H, OH); $^{13}$C NMR (101 MHz, CDCl$_3$) δ: 47.6 (2×CH$_2$), 49.9 (CH$_2$), 56.6 (CH$_2$), 61.74 (CH$_2$), 68.2 (2×CH$_2$), 95.5 (CH$_2$), 115.3 (CH), 118.0 (CH), 119.5 (CH), 125.1 (CH), 129.8 (CH), 135.0 (Cq), 136.26 (Cq), 139.5 (Cq), 144.8 (Cq), 146.5 (CH), 147.8 (Cq), 157.9 (Cq), 158.9 (Cq), 159.6 (Cq); HRMS (EI-MS): C$_{23}$H$_{26}$N$_7$O$_4$ [M+H]$^+$, calculated m/z 464.2046 found m/z 464.2041.

[1-({2-[3-(methoxymethoxy)phenyl]-4-(morpholin-4-yl)pyrido[3,2-d]pyrimidin-7-yl}methyl)-1H-1,2,3-triazol-4-yl]methanol (60): Under an inert atmosphere, in a 10 mL flask, 70 mg (0.17 mmol; 1 equiv.) of (38) were suspended in 3 mL of acetonitrile. Triethylamine was added drop wise until perfect dissolution of the compound into the solution. Then were added 2 mg (0.008 mmol; 0.05 equiv.) of copper iodide and 11 µL (0.187 mmol, 1.1 equiv.) of propargyl alcohol. The mixture was stirred at room temperature for 12 hours. The solution was diluted in ethyl acetate (30 mL). The organic phase was washed with an aqueous solution saturated with NaHCO$_3$ (10 mL), dried on MgSO$_4$, filtered and then concentrated under reduced pressure. The crude residue was then purified by chromatography column on silica gel under pressure (ethyl acetate 100%) allowing isolation of an amorphous white solid with a yield of 51%. Infrared (Diamand ATR, cm$^{-1}$) ν: 3154, 2962, 2848, 1605, 1556, 1495, 1458, 1348, 1266, 1115, 1025, 886, 739, 678, $^1$H NMR (400 MHz, CDCl$_3$) δ: 3.55 (s, 3H, CH$_3$), 3.94 (m, 4H, 2×CH$_2$(O)), 4.61 (bs, 4H, 2×CH$_2$(N)), 4.84 (s, 2H, CH$_2$), 5.30 (s, 2H, CH$_2$), 5.75 (s, 2H, CH$_2$), 7.18 (m, 1H, H$_{arom}$), 7.40 (t, 1H, J=8.0 Hz, H$_{arom}$), 7.58 (s, 1H, CH), 8.02 (m, 2H, H and H$_{arom}$), 8.10 (m, 1H, H$_{arom}$), 8.60 (d, 1H, J=2.0 Hz, H$_6$); $^{13}$C NMR (101 MHz, CDCl$_3$) δ: 48.1 (2×CH$_2$), 51.6 (CH$_2$), 56.1 (CH$_3$), 57.4 (CH$_2$), 67.5 (2×CH$_2$), 94.53 (CH$_2$), 116.3 (CH), 118.5 (CH), 122.2 (CH), 123.4 (Cq), 129.4 (CH), 135.3 (CH), 134.4 (Cq), 135.0 (Cq), 139.0 (CH), 145.9 (CH), 152.7 (Cq), 157.8 (Cq), 158.4 (Cq), 160.5 (Cq), 167.0 (Cq); HRMS (EI-MS): C$_{21}$H$_{21}$N$_7$O$_3$ [M+H]$^+$, calculated m/z 464.2046 found m/z 464.2041.

3-(7-{[4-(fluoromethyl)-1H-1,2,3-triazol-1-yl]methyl}-4-(morpholin-4-yl)pyrido[3,2-d]pyrimidin-2-yl)phenol (61): Under an inert atmosphere, in a 10 mL flask, 35 mg (0.17 mmol; 1 equiv.) of (38) were put into solution in 4 mL of dichloromethane. At 0° C., 11 µL (0.083 mmol, 1.1 equiv.) of diethylaminosulfide trifluoride (DAST) are added drop wise. After one hour, 22 µL (0.34 mmol, 2 equiv.) of diethylaminosulfide trifluoride are added. The mixture was stirred still at 0° C. for 1 hour. The reaction was stopped by adding an aqueous solution saturated with NaHCO$_3$ (10 mL). The organic phase was extracted three times with ethyl acetate (10 mL), dried on MgSO$_4$, filtered and then concentrated under reduced pressure. The step for deprotection of MOM was directly carried out with the residue in order to obtain a yellowish solid (61) with a yield of 62%. MP: 168° C.; Infrared (Diamand ATR, cm$^{-1}$) ν: 3354, 3046, 1620, 1562, 1506, 1425, 1314, 1266, 1115, 1025, 886, 739, 678, $^1$H NMR (400 MHz, CDCl$_3$) δ: 3.86 (m, 4H, 2×CH$_2$(O)), 4.56 (s, 4H, 2×CH$_2$ (N)), 5.55 (d, 2H, J=48 Hz, CH$_2$F), 6.01 (s, 2H, CH$_2$), 7.03 (m, 1H, H$_{arom}$), 7.39 (t, 1H, J=8.0 Hz, H$_{arom}$), 7.77 (m, 1H, H$_{arom}$), 7.83 (d, 1H, J=2.0 Hz, H$_8$), 8.09 (s, 1H, CH), 8.56 (d, 1H, J=2.0 Hz, H$_6$), 8.86 (s. 1H, OH); $^{13}$C NMR (101 MHz, CDCl$_3$) δ: 47.6 (2×CH$_2$), 49.9 (CH$_2$), 55.0 (CH$_2$), 66.4 (2×CH$_2$), 76.4 (d, J=159 Hz, CH$_2$), 114.8 (CH), 117.6 (CH), 119.0 (CH), 123.4 (Cq), 129.3 (CH), 131.8 (CH), 134.4 (Cq), 136.0 (Cq), 139.0 (CH), 145.9 (CH), 147.3 (Cq), 148.6 (Cq), 157.4 (Cq), 158.4 (Cq), 159.2 (Cq); $^{19}$F NMR (376 MHz, DMSO-d$_6$) δ: −202.6 (CH$_2$F); HRMS (EI-MS): C$_{21}$N$_{21}$FN$_7$O$_2$ [M+H]$^+$, calculated m/z 422.1741 found m/z 422.1735.

A.5.9. Preparation of Aldehyde Derivatives in Position C7

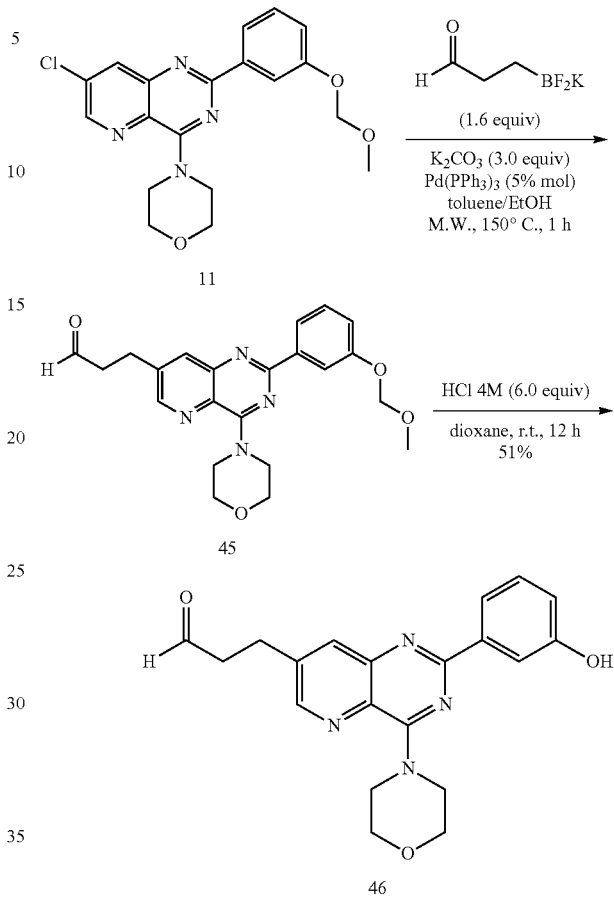

3-(2-(3-(methoxymethoxy)phenyl)-4-morpholinopyrido[3,2-d]pyrimidin-7-yl)propanal (46): The compound (45) was synthesized from the compound (11) (110 mg, 0.284 mmol) by following the general procedure B described earlier.

The reaction intermediate (45) was directly diluted in dioxane and 6 equiv. of a hydrochloric acid gas solution was added to the medium (4 M in dioxane). The mixture was then left with stirring at room temperature for one to three hours. The precipitate was washed with petroleum ether and then recovered by filtration in order to obtain a white solid with a yield of 51%. MP: 213° C. Infrared (Diamand ATR, cm$^{-1}$) ν: 2866, 1723, 1542, 1515, 1423, 1368, 1109, 1023, 882, 743; $^1$H NMR (400 MHz, CDCl$_3$) δ: 2.90 (dd, 2H, J=7.1 Hz, J=7.2 Hz, CH$_2$), 3.10 (dd, 2H, J=7.2 Hz, J=7.3 Hz, CH$_2$), 3.89-3.93 (m, 4H, 2×CH$_2$(O)), 4.55-4.58 (bs, 4H, 2×CH$_2$(N)), 6.98 (ddd, 1H, J=0.9 Hz, J=2.7 Hz, J=8.0 Hz, H$_{arom}$), 7.32 (dd, 1H, J=7.8 Hz, J=7.9 Hz, H$_{arom}$), 7.94-7.97 (m, 3H, 2×H$_{arom}$, H$_8$), 8.54 (d, 1H, J=2.2 Hz, H$_6$), 9.83 (s, 1H, CHO); $^{13}$C NMR (101 MHz, CDCl$_3$) δ: 25.1 (CH$_2$), 44.1 (CH$_2$), 48.0 (2×CH$_2$), 67.3 (2×CH$_2$), 115.3 (CH), 117.7 (CH), 120.9 (CH), 129.6 (CH), 131.5 (Cq), 134.3 (CH), 139.8 (Cq), 139.9 (Cq), 147.2 (CH), 147.9 (Cq), 156.1 (Cq), 159.1 (Cq), 160.1 (Cq), 200.1 (CH); HRMS (EI-MS): C$_{20}$H$_{20}$N$_4$O$_3$ [M+H]$^+$, calculated m/z 365.1659. found m/z 365.1661.

A.5.10. Preparation of Isoxazole Derivatives in Position 7

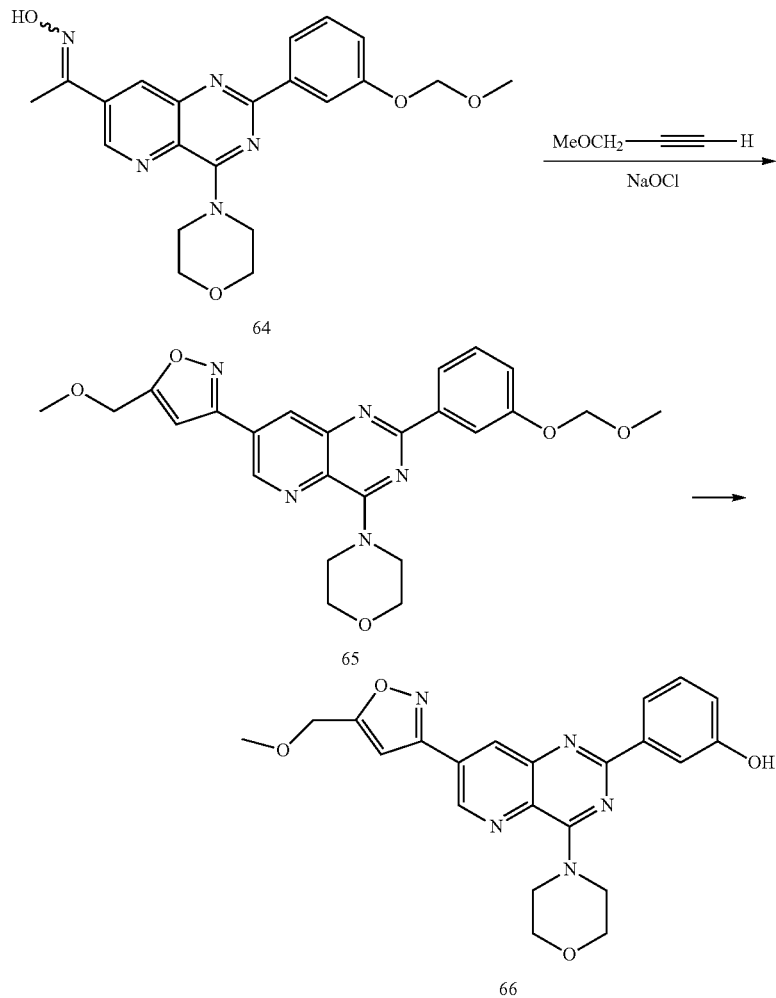

4-{2-[3-(methoxymethoxy)phenyl]-7-{[5-(methoxymethyl)-1,2-oxazol-3-yl]methyl}pyrido[3,2-d]pyrimidin-4-yl}morpholine (65): In a 10 mL flask, 88 mg (0.22 mmol; 1 equiv.) of (64) were solubilized in 4 mL of tetrahydrofurane (THF). 20 µL (0.22 mmol, 1.1 equiv.) of methoxy propargyl ether and 246 µL (15% in water, 0.43 mmol, 2 equiv.) of sodium hypochlorite were added. After one night at room temperature, water (10 mL) was added. The organic phase was extracted three times with ethyl acetate (10 mL), dried on $MgSO_4$, filtered and then concentrated under reduced pressure. The crude residue was then purified by chromatography column on silica gel under pressure (AE/EP 1/1) allowing isolation of a yellowish oil with a yield of 50%. Infrared (Diamand ATR, $cm^{-1}$) ν: 2923, 2852, 1701, 1640, 1508, 1461, 1426, 1268, 1154, 1116, 1071, 1008, 957, 739; $^1H$ NMR (400 MHz, $CDCl_3$) δ: 3.41 (s, 3H, $CH_3$), 3.52 (s, 3H, $CH_3$), 3.92 (m, 4H, 2×$CH_2$(O)), 4.20 (s, 2H, $CH_2$), 4.50 (s, 2H, $CH_2$), 4.60 (bs, 4H, 2×$CH_2$(N)), 5.28 (s, 2H, $CH_2$), 6.88 (t, J=5.5 Hz, 1H, CH), 7.18 (m, 1H, $H_{arom}$), 7.40 (t, 1H, J=7.5 Hz, $H_{arom}$), 6.11 (s, 1H, $H_{arom}$), 7.17 (m, 1H, $H_{arom}$), 7.40 (m, 1H, $H_{arom}$), 8.15 (m, 3H, $H_8$ and 2×$H_{arom}$), 8.58 (d, J=2 Hz, 1H, $H_6$), $^{13}C$ NMR (101 MHz, $CDCl_3$) δ: 30.0 ($CH_2$), 47.7 (2×$CH_2$), 56.2 ($CH_3$), 59.16 ($CH_3$), 65.7 ($CH_2$), 67.4 (2×$CH_2$), 94.8 ($CH_2$), 100.1 (Cq), 102.5 (CH), 116.5 (CH), 118.3 (CH), 122.1 (CH), 129.4 (CH), 135.4 (Cq), 136.5 (CH), 136.2 (Cq), 146.9 (CH), 157.2 (Cq), 157.7 (Cq), 159.2 (Cq), 161.2 (Cq), 170.13 (Cq); HRMS (EI-MS): $C_{26}H_{28}N_5O_5$ [M+H]$^+$, calculated m/z 478.2090. found m/z 478.2085.

3-(7-{[5-(methoxymethyl)-1,2-oxazol-3-yl]methyl}-4-(morpholin-4-yl)pyrido[3,2-d]pyrimidin-2-yl)phenol (66): The compound (66) was synthesized from the compound (65) (50 mg, 0.123 mmol) by deprotection of MOM according to the procedures described earlier. A yellow solid was obtained with a yield of 98%. MP: 169° C.; Infrared (Diamand ATR, $cm^{-1}$) ν: 3200, 2911, 1701, 1640, 1508, 1461, 1426, 1268, 1154, 1116, 1071, 1008, 957, 739; $^1H$ NMR (400 MHz, DMSO-$d_6$) δ: 3.52 (s, 3H, $CH_3$), 3.90 (m, 4H, 2×$CH_2$(O)), 4.37 (s, 2H, $CH_2$), 4.54 (s, 2H, $CH_2$), 4.69 (bs, 4H, 2×$CH_2$(N)), 6.88 (s, 1H, CH), 7.18 (m, 1H, $H_{arom}$), 7.40 (t, 1H, J=7.5 Hz, $H_{arom}$), 7.12 (m, 1H, $H_{arom}$), 7.80 (m, 2H, $H_{arom}$), 8.38 (m, 1H, $H_8$), 8.88 (d, J=2 Hz, 1H, $H_6$), 10.0 (bs, 1H, OH); $^{13}C$ NMR (101 MHz, DMSO-$d_6$) δ: 30.0 ($CH_2$), 47.7 (2×$CH_2$), 58.2 ($CH_3$), 66.0 ($CH_2$), 68.4 (2×$CH_2$), 104.5 (CH), 116.5 (CH), 118.3 (CH), 120.1 (CH), 130.6 (CH), 135.4 (Cq), 136.5 (CH), 136.2 (Cq), 139.8 (Cq), 146.9 (CH), 147.0 (Cq), 157.7 (Cq), 159.2 (Cq), 163.1 (Cq), 170.13 (Cq); HRMS (EI-MS): $C_{23}H_{24}N_5O_4$ [M+H]$^+$, calculated m/z 434.1828. found m/z 434.1823.

A.6. Nitro Group Reduction

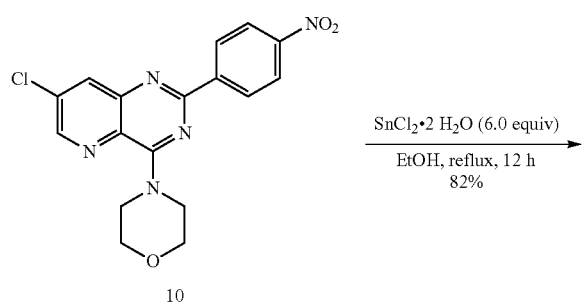

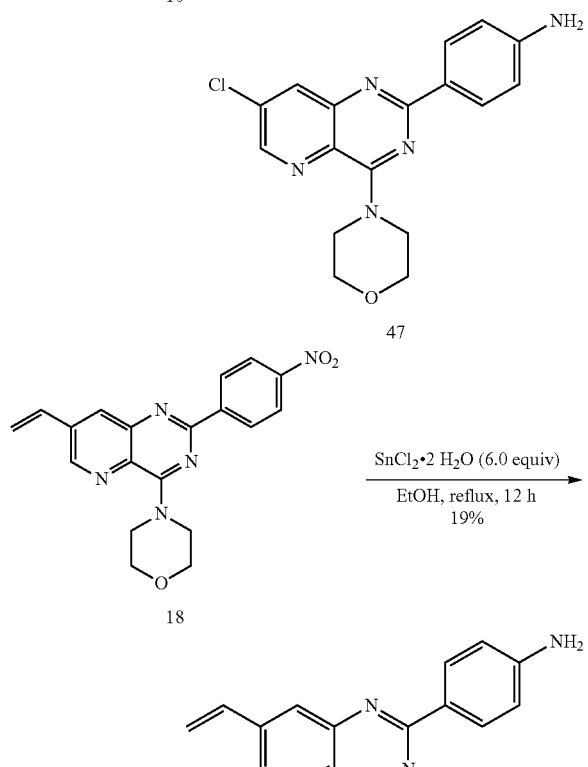

4-(7-chloro-4-morpholinopyrido[3,2-d]pyrimidin-2-yl) aniline (47): In a 50 mL flask, 120 mg (0.323 mmol; 1.0 equiv.) of (10) were dissolved in ethanol (20 mL), 437 mg (1.94 mmol; 6 equiv.) of tin (II) chloride dihydrate were added to the reaction medium. The mixture was refluxed for 12 hours. The ethanol was then evaporated and the residue was taken up in a 1 M NaOH aqueous solution (100 mL). The aqueous phase was extracted with ethyl acetate (2×50 mL). The organic phase was washed with water (2×20 mL), dried on $MgSO_4$, filtered and then concentrated under reduced pressure. The expected product was isolated without additional purification as a yellow solid with a yield of 82%. MP: 220° C.; Infrared (Diamand ATR, $cm^{-1}$) ν: 3419, 3323, 3205, 2966, 2865, 1609, 1587, 1518, 1426, 1306, 1109, 1025, 925; $^1$H NMR (250 MHz, $CDCl_3$) δ: 3.80-3.83 (m, 4H, 2×$CH_2$(O)), 4.44 (bs, 4H, 2×$CH_2$(N)), 5.71 (s, 2H, $NH_2$), 6.64 (d, 2H, J=8.8 Hz, 2×$H_{arom}$), 8.16 (d, 2H, J=8.8 Hz, 2×$H_{arom}$), 8.19 (d, 1H, J=2.4 Hz, $H_8$), 8.65 (d, 1H, J=2.4 Hz, $H_6$); $^{13}$C NMR (101 MHz, $CDCl_3$) δ: HRMS (EI-MS): $C_{17}H_{16}ClN_5O$ $[M+H]^+$, calculated m/z 342.1116. found m/z 342.1117.

4-(4-morpholino-7-vinylpyrido[3,2-d]pyrimidin-2-yl) aniline (48): In a 25 mL flask, 60 mg (0.162 mmol; 1.0 equiv.) of (18) were dissolved in ethanol (15 mL), 219 mg (0.97 mmol, 6.0 equiv.) of tin (II) chloride dihydrate were added to the medium. The mixture was then refluxed for 12 hours. After concentration under reduced pressure, the residue was taken up in a 1 M NaOH aqueous solution (80 mL) which is extracted with ethyl acetate (40 mL). The resulting organic phase was washed with water (2×15 mL), dried on $MgSO_4$, filtered and then concentrated under reduced pressure. The compound (48) was isolated as a yellow solid with a yield of 19% without additional purification. MP: >260° C.; Infrared (Diamand ATR, $cm^{-1}$) ν: 3028, 2972, 2920, 1602, 1553, 1519, 1437, 1345, 1109, 867; $^1$H NMR (400 MHz, $CDCl_3$) δ: 3.90-3.94 (m, 4H, 2×$CH_2$(O)), 4.56-4.53 (bs, 4H, 2×$CH_2$(N)), 5.54 (d, 1H, J=11.0 Hz, $CH_{2alkene}$), 6.04 (d, 1H, J=17.7 Hz, $CH_{2alkene}$), 6.75 (d, 2H, J=8.7 Hz, 2×$H_{arom}$), 6.84 (dd, 1H, J=11.0 Hz, J=17.7 Hz, $CH_{alkene}$), 8.06 (d, 1H, J=2.2 Hz, $H_8$), 8.32 (d, 2H, J=8.7 Hz, 2×$H_{arom}$), 8.67 (d, 1H, J=2.2 Hz, $H_6$); $^{13}$C NMR (101 MHz, $CDCl_3$) δ: 48.2 (2×$CH_2$), 67.4 (2×$CH_2$), 114.7 (2×CH), 118.6 ($CH_2$), 128.7 (Cq), 130.2 (2×CH), 132.2 (Cq), 132.3 (CH), 133.3 (CH), 135.9 (Cq), 144.1 (CH), 148.5 (Cq), 148.9 (Cq), 159.3 (Cq), 160.6 (Cq); HRMS (EI-MS): $C_{19}H_{19}N_5O$ $[M+H]^+$, calculated m/z 335.1662. found m/z 335.1666.

A.8. Formation of Urea

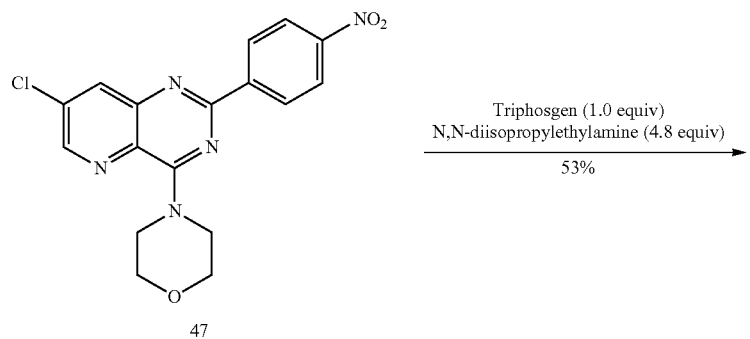

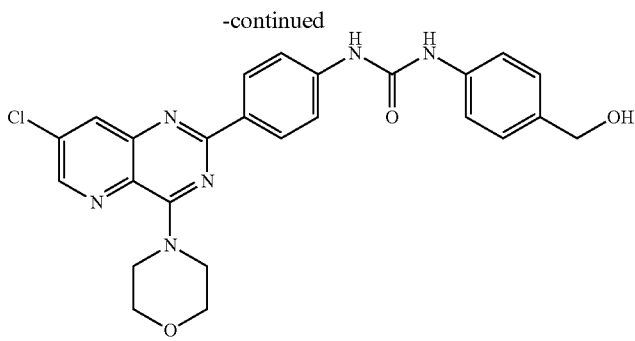

52

1-(4-(7-chloro-4-morpholinopyrido[3,2-d]pyrimidin-2-yl)phenyl)-3-(4-methoxyphenyl)urea (52): Under an argon atmosphere, 26 mg (0.09 mmol; 1 equiv.) of triphosgen were dissolved in 10 mL of anhydrous tetrahydrofurane at −78° C. A solution containing 90 mg (0.26 mmol; 3 equiv.) of (47) as well as 71 μL (0.42 mmol, 4.8 equiv.) of N,N-diisopropylethylamine, dissolved in 5 mL of tetrahydrofurane, was added drop wise to the cooled solution of triphosgen. The mixture was stirred at −78° C. for 5 minutes and then at room temperature. 26 mg (0.26 mmol, 3 equiv.) of 4-hydroxymethylphenylamine and 35 μL (0.21 mmol, 2.4 equiv.) of N,N-diisopropylethylamine, dissolved in 5 mL of tetrahydrofurane were then added drop wise. The reaction medium was then left with stirring for 24 hours. The latter was hydrolysed with an aqueous solution saturated with NaHCO$_3$ (10 mL). The aqueous phase was extracted with ethyl acetate (50 mL). The grouped organic phases were washed with water (1×10 mL), dried on MgSO$_4$, filtered and concentrated under reduced pressure. The product (52) was obtained without any additional purification with a yield of 53% as a yellow solid. MP: >260° C.; Infrared (Diamand ATR, cm$^{-1}$) ν: 3291, 2912, 2857, 1640, 1588, 1509, 1426, 1309, 1208, 1111; $^1$H NMR (400 MHz, CDCl$_3$) δ: 3.80 (s, 4H, 2×CH$_2$(O)), 4.42 (s, 2H, CH$_2$), 4.46 (bs, 4H, 2×CH$_2$(N)), 7.21 (d, 2H, J=8.3 Hz, 2×H$_{arom}$), 7.43 (d, 2H, J=8.3 Hz, 2×H$_{arom}$), 7.59 (d, 2H, J=8.6 Hz, 2×H$_{arom}$), 8.25 (d, 1H, J=2.3 Hz, H$_8$), 8.34 (d, 2H, J=8.6 Hz, 2×H$_{arom}$), 8.69 (d, 1H, J=2.3 Hz, H$_6$), 9.24 (s, 1H, NH), 9.24 (s, 1H, NH); $^{13}$C NMR (101 MHz, CDCl$_3$) δ: 48.1 (2×CH$_2$), 63.1 (CH$_2$), 66.8 (2×CH$_2$), 117.7 (2×CH), 118.3 (2×CH), 127.6 (2×CH), 129.6 (2×CH), 130.9 (Cq), 131.0 (Cq), 134.0 (CH), 136.4 (Cq), 138.7 (Cq), 143.1 (Cq), 144.9 (CH), 148.9 (Cq), 152.9 (Cq), 152.9 (Cq), 158.8 (Cq), 160.2 (Cq); HRMS (EI-MS): C$_{26}$H$_{23}$ClN$_6$O$_3$[M+H]$^+$, calculated m/z 491.1593. found m/z 491.1594.

A.8. Suzuki Coupling in Position 4 of the Compound (3)

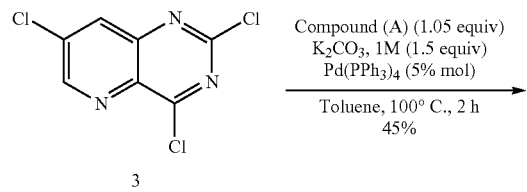

Compound (A) (1.05 equiv)
K$_2$CO$_3$, 1M (1.5 equiv)
Pd(PPh$_3$)$_4$ (5% mol)

Toluene, 100° C., 2 h
45%

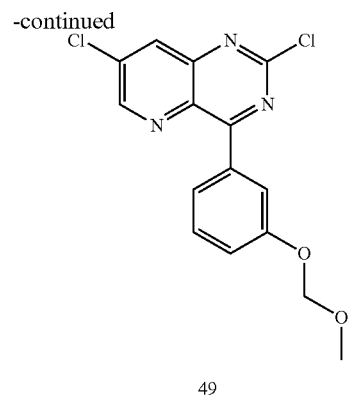

49

2,7-dichloro-4-(3-(methoxymethoxy)phenyl)pyrido[3,2-d]pyrimidine (49): Under an inert atmosphere, in a 25 mL flask, 200 mg (0.85 mmol, 1.0 equiv.) of (3) were dissolved in toluene (10 mL). 145 mg (0.90 mmol, 1.05 equiv.) of 3-methoxymethoxyphenylboronic acid, an aqueous solution (1 mL) containing 176 mg (1.28 mmol, 1.5 equiv.) of potassium carbonate, and then 49 mg (0.05 mmol, 0.05 equiv.) of tetrakis triphenylphosphine were added to the medium. The mixture was then brought to 100° C. for 2 hours. After concentration under reduced pressure, the residue was taken up in dichloromethane (30 mL). The organic phase was washed with water (2×10 mL), dried on MgSO$_4$, filtered and then concentrated under reduced pressure. The crude residue was then directly purified by chromatography on silica gel with (DCM/MeOH, 99/1) mixture in order to obtain the product as a yellow solid with a yield of 43%. MP: 214° C. Infrared (Diamand ATR, cm$^{-1}$) ν: 2972, 1592, 1556, 1492, 1460, 1381, 1335, 1242, 1142, 746; $^1$H NMR (400 MHz, CDCl$_3$) δ: 3.82 (s, 3H, CH$_3$), 5.30 (s, 2H, CH$_2$), 6.96 (s, 1H, H$_{arom}$), 7.35 (d, 1H, J=5.5 Hz, H$_{arom}$), 7.94 (s, 2H, 2×H$_{arom}$), 8.48 (d, 1H, J=3.2 Hz, H$_8$), 8.92 (d, 1H, J=3.4 Hz, H$_6$); $^{13}$C NMR (101 MHz, CDCl$_3$) δ: 56.3 (CH$_3$), 94.5 (CH$_2$), 115.0 (CH), 118.5 (CH), 119.3 (CH), 129.7 (CH), 134.0 (CH), 138.0 (Cq), 142.1 (Cq), 149.1 (CH), 157.6 (Cq), 160.5 (Cq), 162.9 (Cq), 163.8 (Cq), 165.6 (Cq); HRMS (EI-MS): C$_{18}$H$_{11}$Cl$_2$N$_3$O$_2$ [M+H]$^+$, calculated m/z 337.0228. found m/z 337.0316.

A.9. Functionalization in Position C2 of the Compound (49)

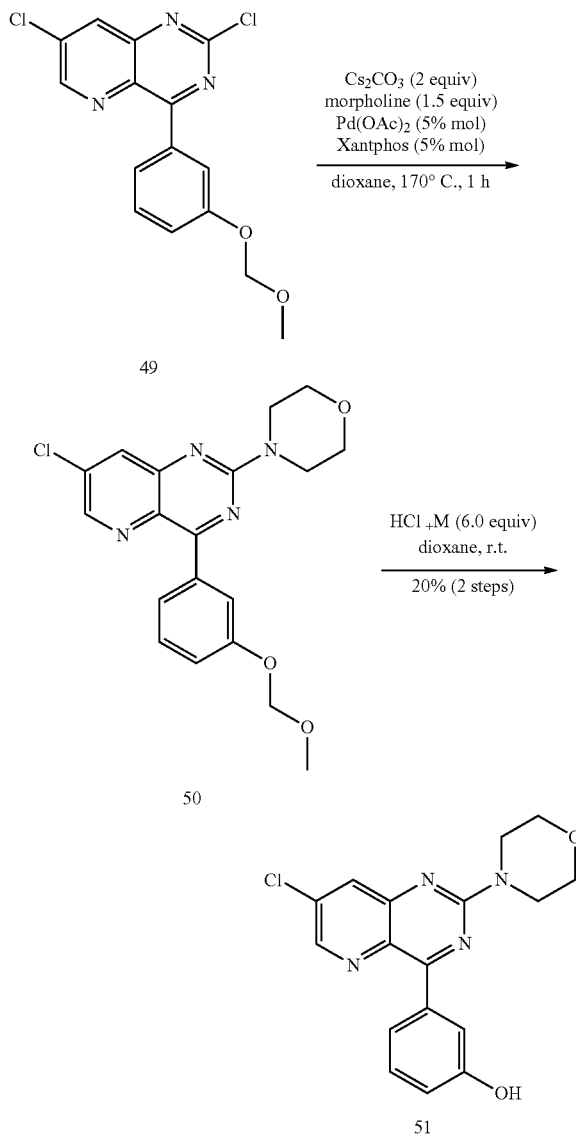

3-(7-chloro-2-morpholinopyrido[3,2-d]pyrimidin-4-yl) phenol (51): In a 5 mL vial, 150 mg (0.45 mmol, 1.0 equiv.) of (49) were dissolved in dioxane (10 mL), 60 µL (0.67 mmol, 1.5 equiv.) of morpholine, 291 mg (0.9 mmol, 2.0 equiv.) of cesium carbonate, and then 5 mg (0.05 mmol, 0.1 equiv.) of palladium acetate and 13 mg (0.2 mmol, 0.05 equiv.) of xantphos were added into the medium. The mixture was then brought to 170° C. for 1 hour under microwave irradiation. After concentration under reduced pressure, the residue was taken up in dichloromethane (30 mL). The organic phase was washed with a solution saturated with sodium chloride (2×10 mL), dried on MgSO$_4$, filtered and then concentrated under reduced pressure. The residue underwent a first purification step with a chromatography column on silica gel under pressure (DCM/MeOH, 99/1).

The obtained intermediate product (50) having impurities, undergoes a second deprotection reaction for separating the desired product from impurities by filtration. (50) was directly diluted in dioxane and 6 equiv. of a hydrochloric acid gas solution were added to the medium (4 M in dioxane). The mixture was left with stirring at room temperature for one to three hours. The precipitate was washed with petroleum ether and then recovered by filtration in order to obtain a final product as a yellow solid, with a yield of 20%. MP: 231° C.; Infrared (Diamand ATR, cm$^{-1}$) ν: 3183, 1595, 1563, 1438, 1338, 1231, 1114, 996, 728; $^1$H NMR (400 MHz, CDCl$_3$) δ: 3.44-3.36 (m, 4H, 2×CH$_2$(O)), 3.98-3.84 (m, 4H, 2×CH$_2$(N)), 7.18 (ddd, 1H, J=1.0 Hz, J=2.5 Hz, J=8.1 Hz, H$_{arom}$) 7.48-7.35 (m, 2H, 2×H$_{arom}$), 8.20 (m, 2H, H$_{arom}$ and H$_8$), 8.70 (d, 1H, J=2.8 Hz, H$_6$); $^{13}$C NMR (101 MHz, CDCl$_3$) δ: 44.1 (2×CH$_2$), 65.3 (2×CH$_2$), 116.2 (CH), 118.1 (CH), 118.7 (CH), 129.6 (CH), 133.2 (CH), 138.1 (Cq), 141.8 (Cq), 149.7 (CH), 158.2 (Cq), 160.1 (Cq), 162.3 (Cq), 163.1 (Cq), 165.6 (Cq); HRMS (EI-MS): C$_{17}$H$_{15}$ClN$_4$O$_2$ [M+H]$^+$, calculated m/z 343.0884. found m/z 343.0921.

B. Preparation of the Urea Compounds of the Invention

B.1. Preparation of the Intermediates Substituted in Position 7

B.1.1. Preparation of the Synthesis Intermediates

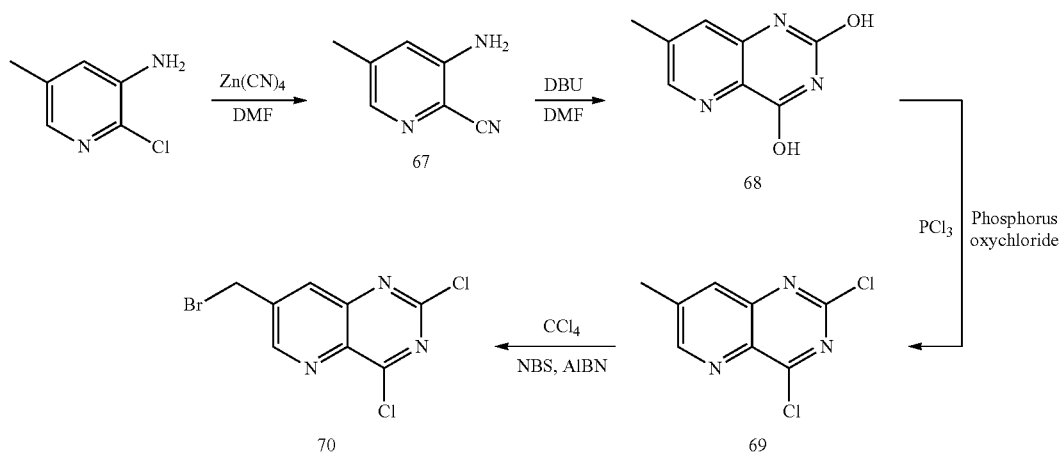

3-amino-5-methylpyridine-2-carbonitrile (67): Under an argon atmosphere, in a 20 mL vial, 1.0 g (7 mmol, 1 equiv.) of 2-chloro-5-methylpyridin-3-amine was dissolved in 15 mL of anhydrous DMF. 821 mg (7 mmol, 1 equiv.) of $Zn(CN)_2$ were added. Next the solution was degassed for 10 minutes and 405 mg (0.35 mmol, 0.05 equiv.) of tetrakis (triphenylphosphino) palladium(0) were added. The mixture was heated to 105° C. for 20 hours. The reaction mixture was filtered on celite and evaporated in vacuo. The crude residue was then purified by chromatography column on silica gel under pressure (AE/EP 2/8) allowing isolation of a white solid with a yield of 65%. MP: 154° C. Infrared (Diamand ATR, $cm^{-1}$) ν: 3404, 2216, 1600, 1465, 1339, 1230, 858, 739; $^1$H NMR (400 MHz, $CDCl_3$) δ: 2.34 (m, 3H, $CH_3$), 4.37 (bs, 2H, $NH_2$), 6.93 (m, 1H, $H_{arom}$), 7.93 (m, 1H, $H_{arom}$); $^{13}$C NMR (101 MHz, $CDCl_3$) δ: 28.7 ($CH_3$), 114.9 (CH), 116.3 (CN), 122.6 (CH), 138.6 (Cq), 142.2 (CH), 146.3 (Cq).

7-methylpyrido[3,2-d]pyrimidine-2,4-diol (68): Under a carbon dioxide atmosphere, in a 20 mL vial, 400 mg (3.0 mmol, 1 equiv.) of 3-amino-5-methylpyridine-2-carbonitrile were dissolved in 8 mL of anhydrous DMF. 448 μL (3.0 mmol, 1 equiv.) of 1,8-diazabicyclo[5.4.0]undec-7-ene (DBU) were added. Next, the solution was degassed for 15 minutes and the vial was sealed. The mixture was then heated to 105° C. for 6 hours (precipitation of the product). At 0° C., 2 mL of 1M HCl were added. The precipitate was filtered in vacuo allowing isolation of a beige solid with a yield of 90%. MP>260° C.; Infrared (Diamand ATR, $cm^{-1}$) ν 3052, 1673, 1410, 1127, 846, 820, 686; $^1$H NMR (400 MHz, DMSO-$d_6$) δ: 2.34 (s, 3H, $CH_3$), 7.34 (s, 1H, $H_{arom}$), 7.93 (s, 1H, $H_{arom}$) 11.07 (bs, 2H, 2×OH); $^{13}$C NMR (101 MHz, DMSO-$d_6$) δ: 18.6 ($CH_3$), 123.46 (CH), 129.74 (Cq), 138.5 (Cq), 139.7 (Cq), 146.2 (CH), 150.5 (Cq), 161.7 (Cq). HRMS (EI-MS): $C_8H_7N_3O_2$ $[M+H]^+$, calculated m/z 178.0617. found m/z 178.0611.

2,4-dichloro-7-methylpyrido[3,2-d]pyrimidine (69): In a 50 mL flask, 1 g (6.65 mmol; 1.0 equiv.) of 7-methylpyrido [3,2-d]pyrimidine-2,4-diol (68) was suspended in 10 mL of phosphorus oxychloride and 4.7 g (22.60 mmol; 4.0 equiv.) of $PCl_5$. The whole was heated to 130° C. After 12 hours of reaction, the excess of $POCl_3$ was evaporated under reduced pressure. The obtained residue was brought to 0° C. by means of an ice bath and then solubilized in dichloromethane (150 mL), the mixture was poured into a water/ice mixture (200 mL) without any basification. After returning to room temperature, the aqueous phase was extracted with dichloromethane (1×100 mL). The organic phases were dried on $MgSO_4$, filtered and then concentrated under reduced pressure. The thereby obtained residue was purified by chromatography column on silica gel under pressure (AE/EP, 2/8) in order to obtain a white solid with a yield of 70%. MP: 146° C.; Infrared (Diamand ATR, $cm^{-1}$) ν 1539, 1439, 1398, 1255, 1137, 1004, 869, 698, 690; $^1$H NMR (400 MHz, $CDCl_3$) δ: 2.68 (m, 3H, $CH_3$), 8.08 (m, 1H, $H_8$), 8.99 (d, 1H, J=2.0 Hz, $H_6$); $^{13}$C NMR (101 MHz, $CDCl_3$) δ: 20.7 ($CH_3$), 135.8 (CH), 136.4 (Cq), 143.2 (Cq), 150.4 (Cq), 156.6 (CH), 157.0 (Cq), 166.7 (Cq); HRMS (EI-MS): $C_7H_2Cl_3N_3$ $[M+H]^+$, calculated m/z 213.9939. found m/z 213.9933.

7-(bromomethyl)-2,4-dichloropyrido[3,2-d]pyrimidine (70): Under an argon atmosphere, in a 20 mL flask, 206 mg (0.99 mmol, 1 equiv.) of 2,4-dichloro-7-methylpyrido[3,2-d]pyrimidine (69) was suspended in 15 mL of anhydrous tetrachloromethane ($CCl_4$). 193 mg (1.09 mmol, 1.1 equiv.) of n-bromosuccinimide (NBS) and 20 mg (0.12 mmol, 0.12 equiv.) of azobisisobutyronitrile (ABM were then added. The solution was degassed for 15 minutes and the mixture was heated with reflux for 12 hours. The reaction mixture was filtered on cotton and evaporated in vacuo. The crude residue was then purified by chromatography column on silica gel under pressure (AE/EP 2/8) allowing isolation of a white solid with a yield of 27%. Infrared ($cm^{-1}$) ν: 1538, 1440, 1380, 1331, 1266, 1209, 927, 868, 698; $^1$H NMR (400 MHz, $CDCl_3$) δ: 4.60 (s, 2H, $CH_2$), 8.26 (m, 1H, $H_8$), 9.12 (d, 1H, J=2.0 Hz, $H_6$); $^{13}$C NMR (101 MHz, $CDCl_3$) δ: 27.4 ($CH_3$), 135.8 (CH), 136.4 (Cq), 143.2 (Cq), 154.4 (Cq), 156.6 (CH), 157.0 (Cq), 166.7 (Cq); HRMS (EI-MS): $C_8H_4BrCl_2N_3$ $[N+H]^+$, calculated m/z 213.9939. found m/z 213.9933.

B.1.2. Suzuki Coupling in Position 4

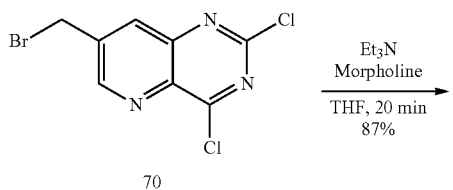

70

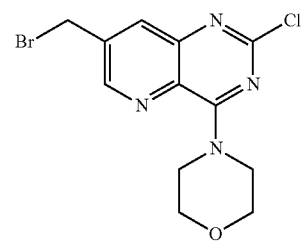

71

4-[7-(bromomethyl)-2-chloropyrido[3,2-d]pyrimidin-4-yl]morpholine (71): Under an argon atmosphere, in a 10 mL flask, 49 mg (0.16 mmol, 1 equiv.) of 7-(bromomethyl)-2, 4-dichloropyrido[3,2-d]pyrimidine (70) were dissolved in 5 mL of anhydrous tetrahydrofurane. At 0° C., 14.7 μL (0.16 mmol, 1 equiv.) of morpholine diluted in 1 mL of anhydrous THF and 23.3 μL (0.16 mmol, 1 equiv.) of triethylamine were then added. The mixture was stirred for 20 min at 0° C. Next an aqueous solution saturated with $NaHCO_3$ (10 mL) was introduced. The organic phase was extracted three times with ethyl acetate (10 mL), dried on $MgSO_4$, filtered and then concentrated under reduced pressure. The crude residue was then purified by chromatography column on silica gel under pressure (AE/EP 2/9) allowing isolation of a white solid with a yield of 87%. MP: 192° C.; MP Infrared ($cm^{-1}$) ν: 3033, 2978, 2861, 1614, 1557, 1430, 1324, 1292, 1136, 1001, 872; $^1$H NMR (400 MHz, $CDCl_3$) δ: 3.87 (t, 4H, J=2.0 Hz, 2×$CH_2$(O)), 4.56 (bs, 6H, $CH_2$ and 2×$CH_2$(N)), 7.97 (d, 1H, J=2.0 Hz, $H_8$), 8.69 (d, 1H, J=2.0 Hz, $H_6$); $^{13}$C NMR (101 MHz, $CDCl_3$) δ: 28.2 ($CH_2$), 48.5 (2×$CH_2$), 67.2 (2×$CH_2$), 132.2 (Cq), 134.8 (CH), 137.7 (Cq), 147.8 (CH), 148.8 (Cq), 157.6 (Cq), 159.3 (Cq); HRMS (EI-MS): $C_{12}H_{12}BrClN_4O$ $[M+H]^+$, calculated m/z 342.9961. found m/z 342.9956.

B.1.3. Functionalization in Position 7

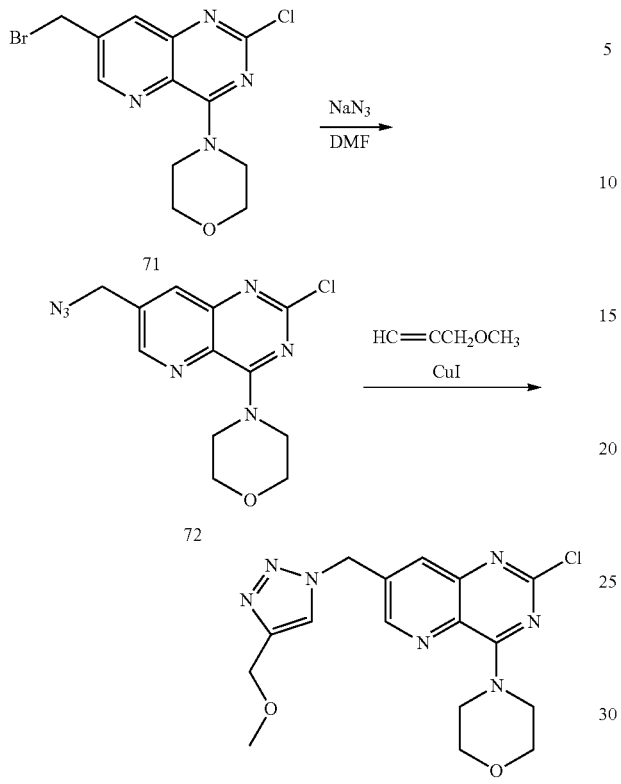

4-[7-(azidomethyl)-2-chloropyrido[3,2-d]pyrimidin-4-yl]morpholine (72): In a 20 mL flask, 141 mg (0.409 mmol; 1 equiv.) of (71) were diluted in 10 mL of dimethylformamide dried on a 4 Å sieve, as well as 40 mg (0.615 mmol; 1.5 equiv.) of sodium nitrite. The mixture was stirred for 15 h at room temperature. 20 mL of water and 20 mL of dichloromethane (DCM) were added. The organic phase was extracted three times with DCM (10 mL), washed with a saline solution (2×20 mL), dried on MgSO$_4$, filtered and then concentrated under reduced pressure. A beige solid was obtained with a yield of 97%. MP: 118° C.; MP Infrared (cm$^{-1}$) ν: 3033, 2978, 2861, 1614, 1557, 1430, 1324, 1292, 1136, 1001, 872; $^1$H NMR (400 MHz, CDCl$_3$) δ: 3.87 (t, 4H, J=2.0 Hz, 2×CH$_2$(O)), 4.56 (bs, 6H, CH$_2$ and 2×CH$_2$(N)), 7.97 (d, 1H, J=2.0 Hz, H$_8$), 8.69 (d, 1H, J=2.0 Hz, H$_6$); $^{13}$C NMR (101 MHz, CDCl$_3$) δ: 48.5 (2×CH$_2$), 51.9 (CH$_2$), 67.2 (2×CH$_2$), 132.2 (Cq), 134.8 (CH), 137.7 (Cq), 147.8 (CH), 148.8 (Cq), 157.6 (Cq), 159.3 (Cq); HRMS (EI-MS): C$_{12}$H$_{13}$ClN$_7$O [M+H]$^+$, calculated m/z 306.0870. found m/z 306.0865.

4-(2-chloro-7-{[4-(methoxymethyl)-1H-1,2,3-triazol-1-yl]methyl}pyrido[3,2-d]pyrimidin-4-yl)morpholine (73): In a 10 mL flask, 21 mg (0.395 mmol; 1.0 equiv.) of (72) were suspended in 3 mL of acetonitrile. 4 mg (0.02 mmol; 0.05 equiv.) of copper iodide and 37 µL (0.434 mmol, 1.1 equiv.) of methoxypropargyl ether were added. Triethylamine was added drop wise until perfect dissolution of the compound in the solution. The mixture was stirred at room temperature for 12 hours. The solution was diluted in ethyl acetate (30 mL). The organic phase was washed with an aqueous solution saturated with NaHCO$_3$ (10 mL), dried on MgSO$_4$, filtered and then concentrated under reduced pressure. The compound (73) was isolated after purification by chromatography column on silica gel under pressure (AE, 100%) with a yield of 67%, as a white solid. MP: 166° C.; Infrared (Diamand ATR, cm$^{-1}$) ν: 2913, 2856, 1558, 1516, 1430, 1315, 1275, 1107, 1062, 1029, 968, 792, 739, 674, $^1$H NMR (400 MHz, CDCl$_3$) δ: 3.41 (s, 3H, CH$_3$), 3.85 (m, 7.82 (d, 1H, J=2.0 Hz, H$_8$), 8.57 (d, J=2.0 Hz, 1H, H$_6$); $^{13}$C NMR (101 MHz, CDCl$_3$) δ: 47.6 (2×CH$_2$), 50.7 (CH$_2$), 58.26 (CH$_3$), 66.0 (CH$_2$), 67.3 (2×CH$_2$), 122.7 (CH), 132.3 (Cq), 133.9 (CH), 134.5 (Cq), 145.9 (CH), 148.0 (Cq), 158.0 (Cq), 159.6 (Cq); HRMS (EI-MS): C$_{16}$H$_{19}$ClN$_7$O$_2$ [M+H]$^+$, calculated m/z 376.1289 found m/z 376.1283.

B.1.4. Functionalization in Positions 4 and 7

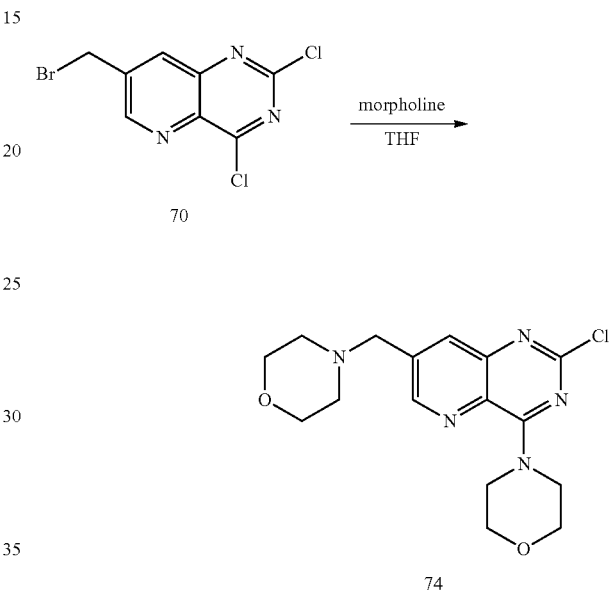

4-[2-chloro-7-(morpholin-4-ylmethyl)pyrido[3,2-d]pyrimidin-4-yl]morpholine (74): Under an argon atmosphere, in a 10 mL flask, 75 mg (0.253 mmol, 1 equiv.) of 7-(bromomethyl)-2,4-dichloropyrido[3,2-d]pyrimidine (73) were dissolved in 2 mL of anhydrous tetrahydrofurane. At 0° C., 29.4 µL (0.506 mmol, 2 equiv.) of morpholine diluted in 1 mL of anhydrous THF and 46.6 µL (0.506 mmol, 2 equiv.) of triethylamine were then added. The mixture was stirred for 1 hour at room temperature. Next, an aqueous solution saturated with NaHCO$_3$ (10 mL) was added. The organic phase was extracted three times with ethyl acetate (10 mL), dried on MgSO$_4$, filtered and then concentrated under reduced pressure. The crude residue was then purified by chromatography column on silica gel under pressure (AE/EP 1/1) allowing isolation of a white solid with a yield of 83%. MP: 162° C.; MP Infrared (cm$^{-1}$) ν: 3148, 3048, 2840, 1555, 1531, 1430, 1324, 1253, 1136, 950, 872, 640; $^1$H NMR (400 MHz, CDCl$_3$) δ: 2.47 (t, 4H, J=2.0 Hz, 2×CH$_2$(O)), 3.64 (s, 2H, CH$_2$), 3.70 (t, 4H, J=2.0 2×CH$_2$(N)), 3.85 (t, 4H, J=2.0 Hz, 2×CH$_2$(O)), 4.57 (bs, 4H, 2×CH$_2$(N)), 7.92 (m, 1H, H$_8$), 8.66 (d, 1H, J=2.0 Hz, H$_6$); $^{13}$C NMR (101 MHz, CDCl$_3$) δ: 49.6 (2×CH$_2$), 54.9 (2×CH$_2$), 61.6 (CH$_2$), 68.3 (2×CH$_2$), 68.6 (2×CH$_2$), 133.2 (Cq), 136.1 (CH), 139.7 (Cq), 149.1 (CH), 150.2 (Cq), 158.6 (Cq), 160.7 (Cq); HRMS (EI-MS): C$_{16}$H$_{21}$ClN$_5$O$_2$[M+H]$^+$, calculated m/z 350.1384. found m/z 350.1378.

B.2. Preparation of the Pinalcolester Intermediates
General Procedure:

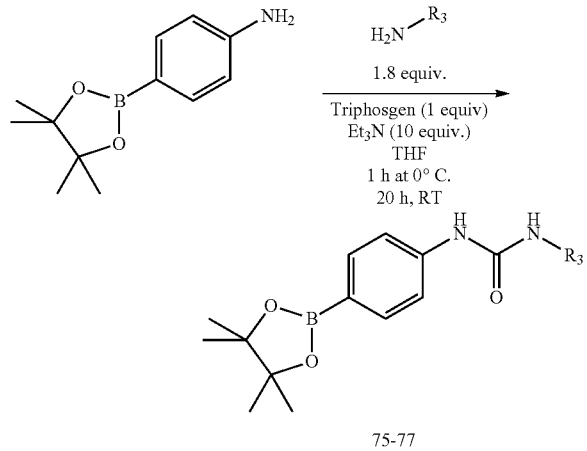

75-77

In an inert atmosphere, in a 10 mL flask, 1.2 equiv. of 4-(4,4,5,5-tetramethyl-1,3,2-dioxaborolan-2-y)aniline was solubilized in 5 mL of THF. At 0° C., 1 equiv. of triphosgen and 10 equiv. of triethylamine were added. After one hour at 0° C., 1.87 equiv. of amine was added. The mixture was stirred at room temperature for 20 hours. The solution was diluted in ethyl acetate (30 mL) and in water (20 mL). The organic phase was extracted with ethyl acetate (3×10 mL), dried on MgSO$_4$, filtered and then concentrated under reduced pressure. The compounds were isolated after purification by a chromatography column on silica gel under pressure.

1-[4-(hydroxymethyl)phenyl]-3-[4-(tetramethyl-1,3,2-dioxaborolan-2-yl)phenyl]urea (75): The compound (75) was synthesized from 4-(aminophenyl)methanol (87 mg, 0.71 mmol) by following the general procedure for obtaining a yellowish solid with a yield of 60%. MP: 184° C.; Infrared (Diamand ATR, cm$^{-1}$) ν: 3261, 3114, 2980, 1597, 1531, 1483, 1438, 1230, 1107, 968, 858, 739; $^1$H NMR (400 MHz, DMSO-d$_6$) δ: 1.28 (s, 12H, 4×CH$_3$), 4.42 (d, 2H, J=5.6 Hz, CH$_2$), 5.05 (t, 1H, J=5.6 Hz, OH), 7.23 (m, 2H, H$_{arom}$), 7.43 (m, 4H, H$_{arom}$), 7.60 (m, 2H, H$_{arom}$), 8.65 (s, 1H, NH), 8.75 (s, 1H, NH); $^{13}$C NMR (101 MHz, DMSO-d$_6$) δ: 25.2 (4×CH$_3$), 63.1 (CH$_2$), 83.8 (Cq), 117.47 (2×CH$_{arom}$), 118.5 (2×CH$_{arom}$), 127.6 (2×CH$_{arom}$), 135.6 (2×CH$_{arom}$), 136.6 (Cq), 138.6 (Cq), 143.2 (Cq), 152.8 (Cq); $^{11}$B NMR (128 MHz, DMSO-d$_6$): δ: 20.0 (s, B); HRMS (EI-MS): C$_{20}$H$_{26}$BN$_2$O$_4$[M+H]$^+$, calculated m/z 369.1986. found m/z 369.1984.

1-[3-(hydroxymethyl)phenyl]-3-[4-(tetramethyl-1,3,2-dioxaborolan-2-yl)phenyl]urea (76): The compound (76) was synthesized from 3-(aminophenyl)methanol (87 mg, 0.71 mmol) by following the general procedure for obtaining a white solid with a yield of 43%. MP: 190° C.; Infrared (Diamand ATR, cm$^{-1}$) ν: 3261, 3114, 2980, 1597, 1531, 1483, 1438, 1230, 1107, 968, 858, 739; $^1$H NMR (400 MHz, DMSO-d$_6$) δ: 1.28 (s, 12H, 4×CH$_3$), 4.42 (d, 2H, J=5.6 Hz, CH$_2$), 5.20 (t, 1H, J=5.6 Hz, OH), 6.90 (m, 1H, H$_{arom}$), 7.22 (m, 1H, H$_{arom}$), 7.43 (m, 4H, H$_{arom}$), 7.60 (m, 2H, H$_{arom}$), 8.65 (s, 1H, NH), 8.75 (s, 1H, NH); $^{13}$C NMR (101 MHz, DMSO-d$_6$) δ: 25.2 (4×CH$_3$), 63.1 (CH$_2$), 83.4 (Cq), 116.7 (CH), 117.0 (CH), 117.47 (2×CH$_{arom}$), 120.0 (CH$_{arom}$), 128.6 (CH$_{arom}$), 135.9 (2×CH$_{arom}$), 139.8 (Cq), 143.2 (Cq), 143.7 (Cq), 152.8 (Cq); $^{11}$B NMR (128 MHz, DMSO-d$_6$): δ: 20.0 (s, B); HRMS (EI-MS): C$_{20}$H$_{26}$BN$_2$O$_4$[M+H]$^+$, calculated m/z 369.1986. found m/z 369.1984.

1-[4-(tetramethyl-1,3,2-dioxaborolan-2-yl)phenyl]-3-(2,2,2-trifluoroethyl)urea (77): The compound (77) was synthesized from 2,2,2-trifluoroethanamine (266 μL, 1.53 mmol) by following the general procedure for obtaining a white solid with a yield of 60%. MP: 134° C.; Infrared (Diamand ATR, cm$^{-1}$) ν: 3337, 1646, 1596, 1560, 1399, 1360, 1515, 1240, 1597, 1230, 1107, 968, 858, 739; $^1$H NMR (400 MHz, DMSO-d$_6$) δ: 1.28 (s, 12H, 4×CH$_3$), 4.42 (d, 2H, J=5.6 Hz, CH$_2$), 5.05 (t, 1H, J=5.6 Hz, OH), 7.23 (m, 2H, H$_{arom}$), 7.43 (m, 4H, H$_{arom}$), 7.60 (m, 2H, H$_{arom}$), 8.65 (s, 1H, NH), 8.75 (s, 1H, NH); $^{13}$C NMR (101 MHz, DMSO-d$_6$) δ: 25.2 (4×CH$_3$), 41.8 (m, CH$_2$), 83.7 (Cq), 117.47 (2×CH$_{arom}$), 125.2 (d, J=277 Hz, Cq), 135.6 (2×CH$_{arom}$), 143.2 (2×Cq), 154.9 (Cq), 157.4 (Cq); $^{11}$B NMR (128 MHz, DMSO-d$_6$): δ: 20.0 (s, B), $^{31}$F NMR (376 MHz, DMSO-d$_6$): δ: −69.5 (t, 3F, CF$_3$), HRMS (EI-MS): C$_{30}$H$_{34}$N$_7$O$_4$[M+H]$^+$, calculated m/z 345.1597. found m/z 345.1596.

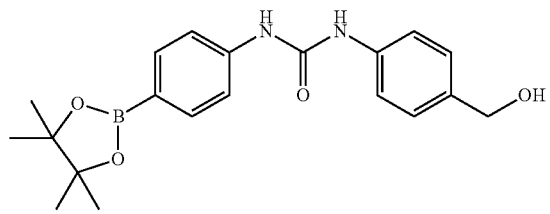

75

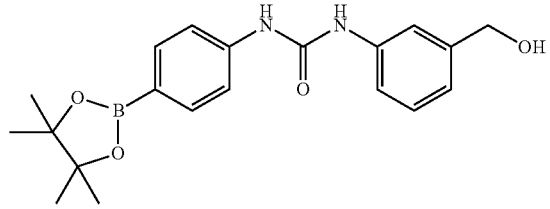

76

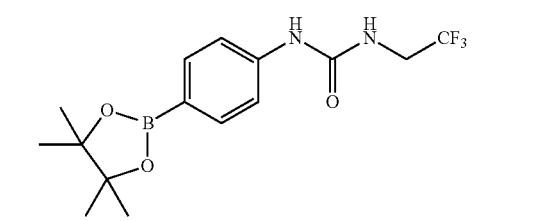

77

B.3. Insertion of the Urea Function in Position 2

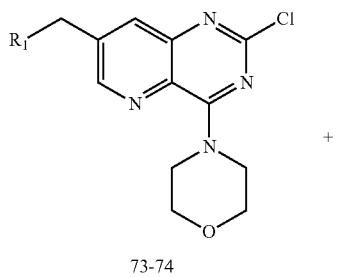

73-74

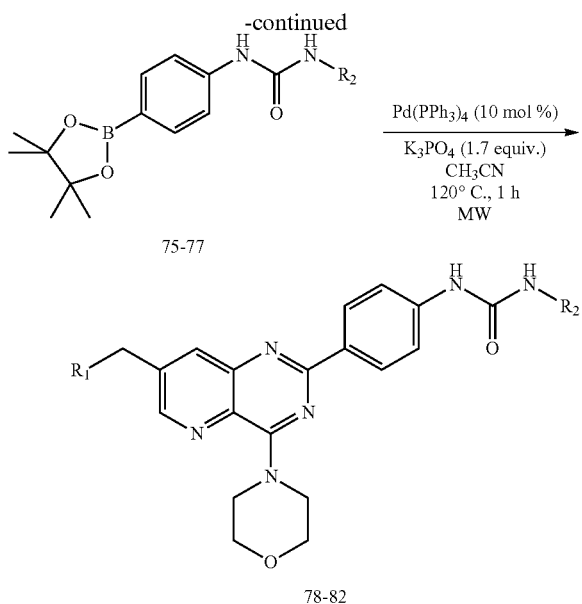

General Procedure: Under an argon atmosphere, in a 5 mL vial, 1.0 equiv. of 4-[2-chloro-7-(morpholin-4-ylmethyl) pyrido[3,2-d]pyrimidin-4-yl]morpholine (74) or 4-(2-chloro-7-{[4-(methoxymethyl)-1H-1,2,3-triazol-1-yl] methyl}pyrido[3,2-d]pyrimidin-4 yl)morpholine (73) was suspended in acetonitrile ($CH_3CN$), 1.7 equiv. of potassium phosphate (C=1.27 M), 1.2 equiv. of pinacolester were added into the medium as well as 0.10 equiv. of tetrakis (triphenylphosphino)palladium (0). The mixture was irradiated with microwaves at 120° C. for 1 h. Next, the reaction medium was stirred at room temperature for 1 h (precipitation of the product) and filtered in vacuo. The precipitate was washed with DCM, ethyl acetate and MeOH.

1-[4-(hydroxymethyl)phenyl]-3-{4-[4-(morpholin-4-yl)-7-(morpholin-4 ylmethyl)pyrido[3,2-d]pyrimidin-2-yl] phenyl}urea (78): The compound (78) was synthesized from 4-[2-chloro-7-(morpholin-4-ylmethyl)pyrido[3,2-d]pyrimidin-4-yl]morpholine (74) (66 mg, 0.19 mmol) by following the aforementioned general procedure for obtaining a yellowish solid with a yield of 56%. MP>260° C.; Infrared (Diamand ATR, $cm^{-1}$) ν: 3338, 2856, 1597, 1531, 1483, 1438, 1230, 1107, 968, 858, 739; $^1H$ NMR (400 MHz, DMSO-$d_6$) δ: 2.44 (t, 4H, J=2.0 Hz, 2×$CH_2$(O)), 3.61 (t, 4H, J=2.0 2×$CH_2$(N)), 3.70 (s, 2H, $CH_2$), 3.82 (t, 4H, J=2.0 Hz, 2×$CH_2$(O)), 4.43 (s, 2H, $CH_2$) 4.51 (bs, 4H, 2×$CH_2$(N)), 7.23 (m, 2H, $H_{arom}$), 7.43 (m, 2H, $H_{arom}$), 7.60 (m, 2H, $H_{arom}$), 8.03 (m, 1H, $H_8$), 8.36 (m, 2H, $H_{arom}$), 8.61 (d, 1H, J=2.0 Hz, $H_6$); 9.00 (bs, 2H, 2×NH); $^{13}C$ NMR (DEPT) (101 MHz, DMSO-$d_6$) δ: 49.1 (2×$CH_2$), 53.6 (2×$CH_2$), 58.9 ($CH_2$), 63.2 ($CH_2$), 67.2 (2×$CH_2$), 67.3 (2×$CH_2$), 117.28 (2×$CH_{arom}$), 118.2 (2×$CH_{arom}$), 127.12 (2×$CH_{arom}$), 129.3 (2×$CH_{arom}$), 135.4 (CH), 147.8 (CH), HRMS (EI-MS): $C_{30}H_{34}N_7O_4$ $[M+H]^+$, calculated m/z 556.2672. found m/z 556.2667.

1-{4-[4-(morpholin-4-yl)-7-(morpholin-4-ylmethyl) pyrido[3,2-d]pyrimidin-2-yl]phenyl}-3-(2,2,2-trifluoroethyl)urea (79): The compound (79) was synthesized from 4-[2-chloro-7-(morpholin-4-ylmethyl)pyrido[3,2-d]pyrimidin-4-yl]morpholine (74) (45 mg, 0.13 mmol) by following the aforementioned general procedure for obtaining a pale yellow solid with a yield of 56%. MP: 186-188° C.; Infrared (Diamand ATR, $cm^{-1}$) ν: 3338, 3295, 1648, 1599, 1571, 1452, 1433, 1230, 1107, 1016, 968, 858, 739; $^1H$ NMR (400 MHz, DMSO-$d_6$) δ: 2.44 (t, 4H, J=2.0 Hz, 2×$CH_2$(O)), 3.61 (t, 4H, J=2.0 2×$CH_2$(N)), 3.70 (s, 2H, $CH_2$), 3.82 (t, 4H, J=2.0 Hz, 2×$CH_2$(O)), 4.43 (s, 2H, $CH_2$), 4.51 (bs, 4H, 2×$CH_2$(N)), 7.23 (m, 2H, $H_{arom}$), 7.43 (m, 2H, $H_{arom}$), 7.60 (m, 2H, $H_{arom}$), 8.03 (m, 1H, $H_8$), 8.36 (m, 2H, $H_{arom}$), 8.61 (d, 1H, J=2.0 Hz, $H_6$); 9.00 (bs, 2H, 2×NH); $^{13}C$ NMR (DEPT) (101 MHz, DMSO-$d_6$) δ: 49.1 (2×$CH_2$), 53.6 (2×$CH_2$), 58.9 ($CH_2$), 63.2 ($CH_2$), 67.2 (2×$CH_2$), 67.3 (2×$CH_2$), 117.28 (2×$CH_{arom}$), 118.2 (2×$CH_{arom}$), 127.12 (2×$CH_{arom}$), 129.3 (2×$CH_{arom}$), 135.4 (CH), 147.8 (CH), HRMS (EI-MS): $C_{30}H_{34}N_7O_4[M+H]^+$, calculated m/z 556.2672. found m/z 556.2667.

1-[3-(hydroxymethyl)phenyl]-3-{4-[4-(morpholin-4-yl)-7-(morpholin-4-ylmethyl)pyrido[3,2-d]pyrimidin-2-yl] phenyl}urea (80): The compound (80) was synthesized from 4-[2-chloro-7-(morpholin-4-ylmethyl)pyrido[3,2-d]pyrimidin-4-yl]morpholine (74) (45 mg, 0.13 mmol) by following the aforementioned general procedure for obtaining a pale yellow solid with a yield of 34%. MP: 200-202° C.; Infrared (Diamand ATR, $cm^{-1}$) ν: 3338, 3281, 2857, 1699, 1596, 1483, 1438, 1230, 1107, 1029, 968, 858, 739; $^1H$ NMR (400 MHz, DMSO-$d_6$) δ: 2.44 (t, 4H, J=2.0 Hz, 2×$CH_2$(O)), 3.61 (t, 4H, J=2.0 2×$CH_2$(N)), 3.70 (s, 2H, $CH_2$), 3.82 (t, 4H, J=2.0 Hz, 2×$CH_2$(O)), 4.43 (s, 2H, $CH_2$) 4.51 (bs, 6H, $CH_2$ et 2×$CH_2$(N)), 6.92 (m, 1H, $H_{arom}$), 7.23 (m, 1H, $H_{arom}$), 7.37 (m, 1H, $H_{arom}$), 7.47 (m, 1H, $H_{arom}$), 7.60 (m, 2H, $H_{arom}$), 8.04 (m, 1H, $H_8$), 8.36 (m, 2H, $H_{arom}$), 8.61 (d, 1H, J=2.0 Hz, $H_6$); 9.00 (bs, 2H, 2×NH); $^{13}C$ NMR (DEPT) (101 MHz, DMSO-$d_6$) δ: 48.4 (2×$CH_2$), 53.96 (2×$CH_2$), 59.6 ($CH_2$), 65.6 ($CH_2$), 66.6 (2×$CH_2$), 116.4 (2×$CH_{arom}$), 117.6 (2×$CH_{arom}$), 120.7 ($CH_{arom}$), 124.3 ($CH_{arom}$), 129.3 (2×$CH_{arom}$), 135.4 (CH), 147.8 (CH), HRMS (EI-MS): $C_{30}H_{34}N_7O_4$ $[M+H]^+$, calculated m/z 556.2672. found m/z 556.2667.

1-[4-(hydroxymethyl)phenyl]-3-[4-(7-{[4-(methoxymethyl)-1H-1,2,3-triazol-1-yl]methyl}-4-(morpholin-4-yl) pyrido[3,2-d]pyrimidin-2-yl)phenyl]urea (81): The compound (81) was synthesized from 4-(2-chloro-7-{[4-(methoxymethyl)-1H-1,2,3-triazol-1-yl]methyl}pyrido[3,2-d]pyrimidin-4-yl)morpholine (73) (53 mg, 0.14 mmol) by following the aforementioned general procedure for obtaining a yellowish solid with a yield of 25%. MP>260° C.; Infrared (Diamand ATR, $cm^{-1}$) ν: 3193, 2856, 1696, 1596, 1506, 1435, 1438, 1230, 1107, 968, 858, 739; $^1H$ NMR (400 MHz, DMSO-$d_6$) δ: 3.29 (s, 3H, $CH_3$), 3.82 (m, 4H, 2×$CH_2$(O)), 4.48 (m, 8H, 2×$CH_2$ and 2×$CH_2$(N)), 5.89 (s, 2H, $CH_2$), 7.23 (m, 2H, $H_{arom}$), 7.43 (m, 2H, $H_{arom}$), 7.60 (m, 2H, $H_{arom}$), 8.03 (m, 1H, $H_8$), 8.33 (s, 1H, $H_{triazole}$), 8.36 (m, 2H, $H_{arom}$), 8.61 (d, 1H, J=2.0 Hz, $H_6$); 9.00 (bs, 2H, 2×NH); $^{13}C$ NMR (101 MHz, DMSO-$d_6$) δ: 47.6 (2×$CH_2$), 57.8 ($CH_3$), 63.1 ($CH_2$), 65.4 (2×$CH_2$), 50.7 ($CH_2$), 117.9 (2×CH), 118.9 (2×CH), 125.0 (CH), 127.6 (2×CH), 129.5 (2×CH), 131.3 (Cq), 132.2 (Cq), 134.5 (Cq), 136.2 (CH), 136.6 (Cq), 138.6 (2×Cq), 142.7 (Cq), 144.8 (Cq) 148.0 (CH), 152.8 (Cq), 158.9 (Cq), 159.5 (Cq); HRMS (EI-MS): $C_{30}H_{32}N_9O_4$ $[M+H]^+$, calculated m/z 582.2577. found m/z 582.2577.

1-[4-(7-{[4-(methoxymethyl)-1H-1,2,3-triazol-1-yl] methyl}-4-(morpholin-4-yl)pyrido[3,2-d]pyrimidin-2-yl) phenyl]-3-(2,2,2-trifluoroethyl)urea (82): The compound (82) was synthesized from 4-(2-chloro-7-{[4-(methoxymethyl)-1H-1,2,3-triazol-1-yl]methyl}pyrido[3,2-d]pyrimidin-4-yl)morpholine (73) (53 mg, 0.14 mmol) by following the aforementioned general procedure for obtaining a yellowish solid with a yield of 25%. MP>260° C. Infrared (Diamand ATR, $cm^{-1}$) ν: 3361, 3021, 2820, 1600, 1556, 1513, 1483, 1438, 1230, 1107, 968, 858, 811, 739; $^1$H NMR (400 MHz, DMSO-$d_6$) δ: 3.29 (s, 3H, CH$_3$), 3.82 (m, 4H, 2×CH$_2$(O)), 3.93 (m, 2H, CH$_2$CF$_3$), 4.48 (bs, 6H, CH$_2$ and 2×CH$_2$(N)), 5.88 (s, 2H, CH$_2$), 6.87 (t, 1H, J=7 Hz, NH), 7.23 (m, 2H, H$_{arom}$), 7.43 (m, 2H, H$_{arom}$), 7.95 (m, 1H, H$_8$), 8.33 (s, 2H, H$_{arom}$), 8.36 (s, 1H, H$_{triazole}$), 8.71 (d, 1H, J=2.0 Hz, H$_6$); 9.05 (s, 1H, NH); $^{13}$C NMR (101 MHz, DMSO-$d_6$) δ: 47.6 (2×CH$_2$), 57.8 (CH$_3$), 63.1 (CH$_2$), 65.4 (2×CH$_2$), 50.7 (CH$_2$), 117.9 (2×CH), 118.9 (2×CH), 125.0 (CH), 127.6 (2×CH), 129.5 (2×CH), 131.3 (Cq), 132.2 (Cq), 134.5 (Cq), 136.2 (CH), 136.6 (Cq), 138.6 (2×Cq), 142.7 (Cq), 144.8 (Cq) 148.0 (CH), 152.8 (Cq), 158.9 (Cq), 159.5 (Cq); HRMS (EI-MS): C$_{25}$H$_{27}$F$_3$N$_9$O$_3$ [M+H]$^+$, calculated m/z 558.2189. found m/z 582.2183.

78

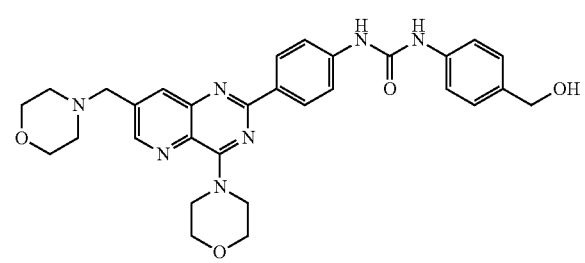

79

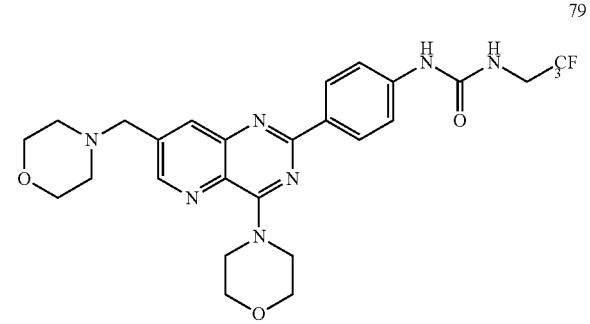

80

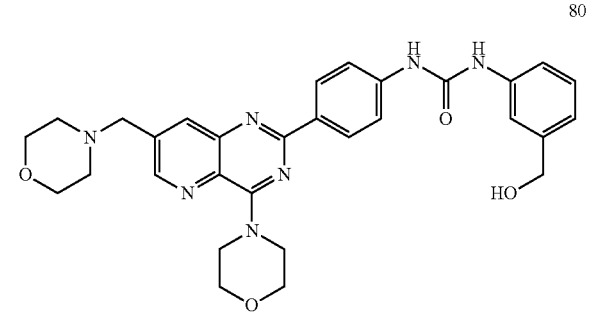

81

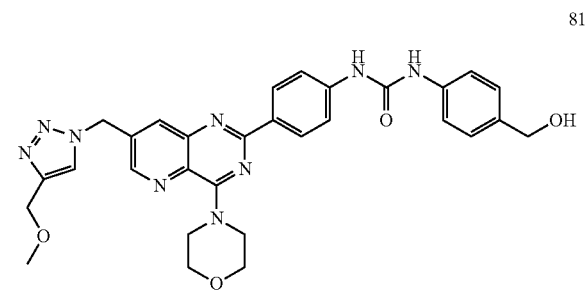

82

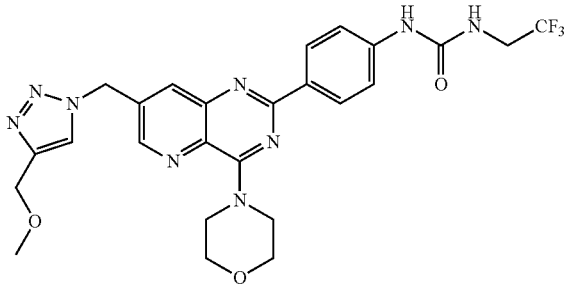

C. Biological results

The activity of the PI3Kα kinase was evaluated by using a purified heterodimer (reference: PV4788 from Invitrogen) consisting of the α catalytic p110 subunit (PIK3CA) and the α regulation p85 subunit (PIK3R1). The assay of the kinase with the kit Adapta™ (reference: PV5099 from Invitrogen) is an enzymatic test based on the detection of ADP, produced during the reaction, by the fluorescence technique TR-FRET. It took place in a 384-well plate and was able to be divided into two phases: an enzymatic reaction phase, and a phase for detecting the ADP level.

During the enzymatic reaction phase, the following components were mixed in 10 μL of a same well: 2.5 μL of each dilution in series of inhibitors taken up in DMSO and then diluted to 1/25 in the reaction buffer (250 mM HEPES pH 7.5, 500 mM NaCl, 0.15 CHAPS, 5 mM EGTA, 15 mM MgCl$_2$ and 1 mM DTT, ref.: PV5101 from Invitrogen), 2.5 μL of a solution containing PI3K at the optimum concentration (concentration defined according to the optimization step described in the operating procedure of the kit) diluted in the same reaction buffer, and finally, 5 μL of a solution containing 20 μM ATP and 100 μM PIP2 diluted in the reaction buffer. For each inhibitor concentration, the reaction was conducted in three copies (triplicate). The reaction was then incubated for 60 min at room temperature without any stirring in darkness.

During the phase for detecting ADP, 5 μL of a detection solution containing an anti-ADP antibody labeled with europium (6 nM), a tracer of the Alexa Fluor® 647 type coupled with ADP (30 nM), and EDTA (30 mM, for stopping the kinase reaction) were diluted in the dilution buffer (reference: PV3574 from Invitrogen). After 30 min of incubation at room temperature with stirring (40 rpm) in darkness, the 384-well plates were read in a plate reader Victor V configured for HTRF (Perkin Elmer). The excitation was produced at 340 nm and emission was measured at 665 nm and 615 nm. The inhibition curve was then plotted according to the emission ratio at 665 nm/615 nm versus the inhibitor concentration.

In order to obtain a linear response of the signal, a titration curve ATP-ADP, corresponding to the conversion % of ATP into ADP, was achieved by varying both of these species while keeping [ADP]+[ATP]=10 μM. The emission ratio at 665 nm/615 nm resulting from this (Y) was plotted versus the conversion % of ATP into ADP (X). The data of this curve were formatted according to a model with three hyperbolic parameters from the following equation:

$$Y = C + A * (1 - (X/(B+X))).$$

The software package GraphPad™ Prism® thus allows calculation of the parameters A, B and C. A conversion % corresponds to an emission ratio 665 nm/615 nm, this percentage is calculated by using the following equation:

Conversion %=$B*(C+A-\text{Ratio})/(\text{Ratio}-C)$

The three parameters A, B and C having been defined by the preceding equation, the conversion % was therefore able to be plotted versus the inhibitor concentration. The amount of inhibitor required for causing a 50% variation in the % conversion of ATP into ADP corresponds to the $IC_{50}$ value of the inhibitor.

The activity of the kinase PI3Kγγ (PV4786 from Invitrogen) was evaluated on the p110γγ catalytic subunit (PI3KCG) and that of the kinase PI3Kδδ on the purified heterodimer (PV5273) respectively consisting of the δδ catalytic p110 subunit (PIK3CD) and the α regulation p85 subunit (PIK3R1) by following the same procedure.

C.2. mTOR Kinase Activity

The activity of the mTOR kinase was evaluated by using a purified truncated protein of the amino acids 1-1359 (reference: PV4753 from Invitrogen). The assay of the activity of the enzyme was carried out with the kit LANCE® Ultra which is an enzymatic test based on the detection of a phosphorylated peptide produced during the reaction, by using the fluorescence technique TR-FRET. It took place in a 384-well plate and was able to be divided into two phases: an enzymatic reaction phase and a phase for detecting the phosphorylated peptide.

During the enzymatic reaction phase, the following components were mixed in 10 μL of a same well: 5 μL of each dilution in series of inhibitors taken up in DMSO and then diluted to 1/25 in the reaction buffer (50 mM HEPES pH 7.5, 0.1% Tween-20, 1 mM EGTA, 10 mM $MnCl_2$, 3 mM $MgCl_2$ and 2 mM of DTT), 2.5 μL of a solution containing mTOR at the optimum concentration (concentration defined according to the optimization step described in the operating procedure of the kit) diluted in the same reaction buffer, and finally 2.5 μL of a solution containing 40 μM of ATP and 200 μM non-phosphorylated peptide diluted in the reaction buffer. For each inhibitor concentration, the reaction was conducted in three copies (triplicate). The reaction was then incubated for 120 min at room temperature without any stirring in darkness.

During the phase for detecting the phosphorylated peptide, 5 μL of an EDTA solution (32 mM) diluted in the dilution buffer (ref.: CR97-100 from Perkin Elmer) were injected into each well. After 5 min of incubation with stirring, 5 μL of a phosphorylated anti-peptide antibody solution labeled with europium (8 nM) and diluted in the same dilution buffer was added into each well. After 60 min of incubation at room temperature with stirring (40 rpm) in darkness, the 384-well plates were read in a plate reader Victor V configured for HTRF (Perkin Elmer). The excitation was achieved at 340 nm and emission was measured at 665 nm. The inhibition curve was then plotted according to the fluorescence intensity value at 665 nm versus the inhibitor concentration.

The amount of inhibitor required for causing a 50% variation in the intensity of the signal corresponds to the $IC_{50}$ value of the inhibitor.

C.3. Results

The obtained results are indicated in the tables hereafter.

| No. | Species | Kinases ($IC_{50}$ in μM) | | | |
|---|---|---|---|---|---|
| | | PI3Kα | PI3Kγ | PI3Kδ | mTOR |
| 6 | 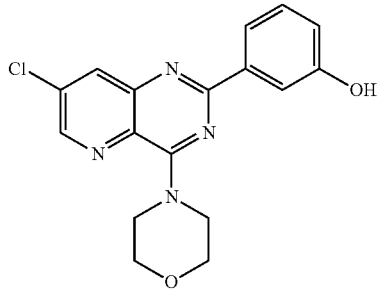 [SMILES: Oc1cccc(-c2nc(N3CCOCC3)c3ncc(Cl)cc3n2)c1] | 0.012 | 0.273 | 0.010 | 0.183 |
| 7 | 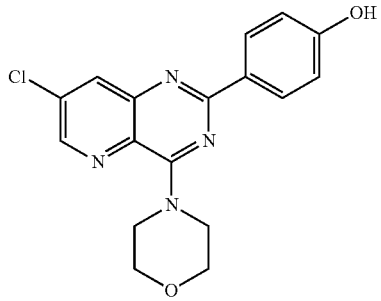 [SMILES: Oc1ccc(-c2nc(N3CCOCC3)c3ncc(Cl)cc3n2)cc1] | 15.2 | >50 | 1.5 | 0.184 |

-continued

| No. | Species | Kinases (IC 50 in μM) | | | |
|---|---|---|---|---|---|
| | | PI3Kα | PI3Kγ | PI3Kδ | mTOR |
| 8 | | 0.032 | 0.431 | 0.016 | >50 |
| 9 | | 6.2 | 3.1 | 0.363 | >50 |
| 14 | | 0.098 | 0.196 | 0.011 | 0.109 |
| 15 | | 0.021 | 0.248 | 0.008 | 0.37 |
| 16 | | 1.6 | 1.7 | 2.1 | 0.37 |

-continued

| No. | Species | Kinases (IC 50 in μM) | | | |
|---|---|---|---|---|---|
| | | PI3Kα | PI3Kγ | PI3Kδ | mTOR |
| 22 | | 0.082 | 0.344 | 0.041 | 0.46 |
| 20 | | 0.047 | >50 | 0.010 | 0.071 |
| 27 | | 0.109 | 0.428 | 0.011 | 0.249 |
| 28 | | 0.358 | 0.769 | 0.213 | 1.2 |
| 29 | | 0.043 | 1.3 | 0.041 | 0.286 |

-continued
| | | Kinases (IC 50 in μM) | | | |
|---|---|---|---|---|---|
| No. | Species | PI3Kα | PI3Kγ | PI3Kδ | mTOR |
| 30 | 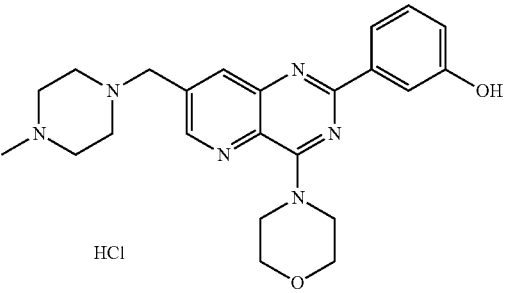 [SMILES: CN1CCN(Cc2cnc3c(N4CCOCC4)nc(-c4cccc(O)c4)nc3c2)CC1 ; Cl] HCl | 0.391 | 0.244 | 0.157 | 2.2 |
| 31 | 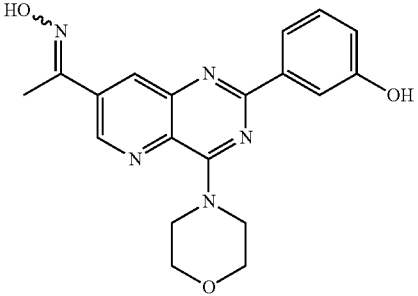 [SMILES: CC(=NO)c1cnc2c(N3CCOCC3)nc(-c3cccc(O)c3)nc2c1] | 0.050 | 0.039 | 0.047 | 0.064 |
| 32 | 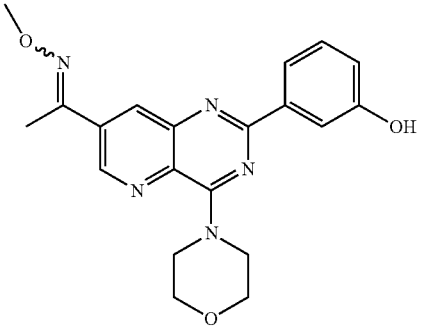 [SMILES: CON=C(C)c1cnc2c(N3CCOCC3)nc(-c3cccc(O)c3)nc2c1] | 0.0026 | 0.260 | 0.012 | 0.005 |
| 34 | 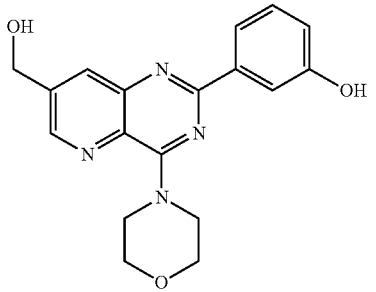 | 0.366 | 0.022 | 0.126 | 0.35 |
| 37 | 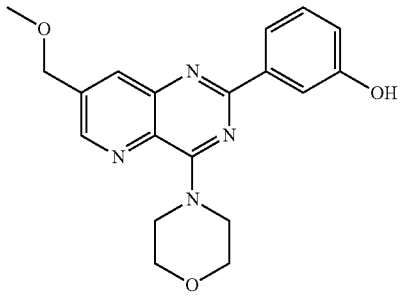 [SMILES: COCc1cnc2c(N3CCOCC3)nc(-c3cccc(O)c3)nc2c1] | 0.103 | 0.179 | 0.083 | 0.070 |

-continued

| No. | Species | Kinases (IC 50 in μM) | | | |
| --- | --- | --- | --- | --- | --- |
| | | PI3Kα | PI3Kγ | PI3Kδ | mTOR |
| 39 | | 0.010 | 0.043 | 0.022 | 0.055 |
| 43 | | 0.808 | 0.018 | 0.231 | 0.404 |
| 44 | | 0.0098 | 0.081 | 0.033 | 0.256 |
| 41 | | 0.051 | 0.127 | 0.34 | 0.82 |
| 42 | | 0.010 | 0.399 | 0.063 | 0.135 |

-continued

| No. | Species | Kinases (IC 50 in μM) | | | |
| --- | --- | --- | --- | --- | --- |
| | | PI3Kα | PI3Kγ | PI3Kδ | mTOR |
| 46 | | 0.057 | 0.563 | 0.081 | 1.9 |
| 51 | | 0.546 | 5.0 | 3.9 | 5.2 |
| 55 | | 0.056 | — | — | — |
| 56 | | 0.011 | — | — | — |
| 58 | | 0.038 | — | — | — |

-continued

| No. | Species | Kinases (IC 50 in μM) | | | |
| --- | --- | --- | --- | --- | --- |
| | | PI3Kα | PI3Kγ | PI3Kδ | mTOR |
| 59 | | 0.116 | — | — | — |
| 61 | | 0.391 | — | — | — |
| 62 | | 0.102 | — | — | — |
| 78 | | 0.023 | — | — | — |
| 81 | | 0.003 | — | — | — |

| No. | Species | Kinases (IC 50 in µM) | | | |
|---|---|---|---|---|---|
| | | PI3Kα | PI3Kγ | PI3Kδ | mTOR |
| 82 | (structure shown) | 0.018 | — | — | — |

The compounds according to the invention were also tested on the cell lines HuH7, CaCo-2, HCT116, PC3, NCl, HacaT and Fibroblasts. On cancer lines, $IC_{50}$s which may range up to 0.1 µM were evaluated under the described conditions (over 48 h).

Operating Procedure: The cells were cultivated according to the ECACC recommendations. The toxicity test of the compounds on these cells was conducted as follows: $4\times10^3$ cells/well were sown in 96 wells. 24 hours after sowing the cells, the cells were exposed to increased concentrations of the compounds (0.1 µM-0.3 µM-0.9 µM-2.7 µM-8.3 µM-25 µM). After 48 hours of treatment, the cells were washed in PBS and bound in a cold ethanol/acetic acid (90/5) mixture for 20 minutes. Next, the nuclei were coloured with Hoechst 3342 (Sigma). The acquisition of images and the analysis was carried out by means of a reader Cellomics ArrayScan VTI/HCS (Thermo Scientific).

The obtained results are grouped in the following table:

| | IC 50 µM | | | | | | | |
|---|---|---|---|---|---|---|---|---|
| Compounds | HUH7 | CaCo2 | MDA | HCT116 | PC3 | NCl | HacaT | Fibroblasts |
| 5 | >25 | >25 | >25 | >25 | >25 | >25 | — | >25 |
| 6 | 0.8 | 8 | >25 | 9 | >25 | >25 | 4 | >25 |
| 7 | 25 | 25 | 25 | >25 | 25 | >25 | — | >25 |
| 8 | 25 | 3 | 20 | 5 | 20 | >25 | — | 2 |
| 9 | >25 | >25 | >25 | >25 | >25 | >25 | >25 | >25 |
| 51 | >25 | 20 | >25 | >25 | >25 | >25 | >25 | >25 |
| 14 | 20 | 1.5 | 20 | 5 | 20 | 20 | — | >25 |
| 16 | >25 | >25 | >25 | >25 | >25 | >25 | >25 | >25 |
| 17 | 15 | 5 | >25 | 6 | 25 | >25 | 4 | >25 |
| 20 | 20 | 4 | 20 | 6 | 25 | >25 | — | >25 |
| 22 | >25 | 4 | 10 | 5 | 4 | >25 | — | >25 |
| 34 | 1 | 1.5 | 25 | 3 | 5 | >25 | — | 25 |
| 37 | 1.5 | 1.5 | 20 | 4 | 4 | 10 | 3 | >25 |
| 31 | 3 | 1.2 | >25 | 2 | 2 | >25 | 2 | >25 |
| 32 | 4 | 3 | 20 | 5 | 5 | 6 | 4 | 0.8 |
| 30 | 5 | 2 | 20 | 10 | 7 | 15 | 8 | >25 |
| 27 | >25 | 3 | >25 | 5 | 2 | >25 | >25 | >25 |
| 28 | 15 | 10 | >25 | 20 | 25 | 25 | 20 | >25 |
| 29 | >25 | 3 | >25 | 5 | 2 | >25 | 8 | >25 |
| 39 | 4 | 2 | >25 | 5 | 3 | 3 | 4 | >25 |
| 44 | 4 | 1 | 15 | 3 | 4 | 4 | 2 | >25 |
| 43 | 4 | 1 | 15 | 3 | 4 | 4 | 2 | >25 |
| 56 | 6 | 6 | 12 | 7 | 8 | 11 | 8 | 10 |
| 78 | 2 | 12 | 3 | 1 | 2 | 3 | 2 | >25 |
| 81 | 7 | 2 | 0.5 | 0.1 | 0.1 | 0.3 | 0.3 | >25 |

What is claimed is:

1. A compound of the following formula (I-3-1):

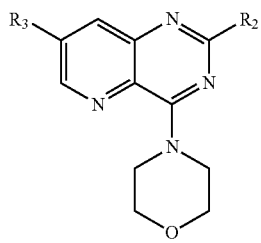

wherein:

-R$_2$ is an aryl group having the following formula:

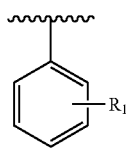
(E)

wherein R$_j$ is
  a group —NH—C(O)—NHR'λ, R'λ, being selected from aryl groups comprising from 5 to 30 carbon atoms, said aryl groups being optionally substituted; and -R$_3$ is selected from the group consisting of:
  halogen atoms selected from the group consisting of F, Cl and I,
  alkenyls consisting of from 2 to 20 carbon atoms, optionally substituted,
  groups —C(O)R$_c$, R$_c$ being selected from the group consisting of a hydrogen atom and an alkyl group consisting of from 1 to 10 carbon atoms, said alkyl group being optionally substituted,
  groups —C(O)OR'$_c$, R'$_c$ being selected from the group consisting of a hydrogen atom and an alkyl group consisting of from 1 to 10 carbon atoms, said alkyl group being optionally substituted,
  groups —C(R$_e$)=N-(OR$_d$), R$_d$ and R$_e$ being selected independently from the group consisting of a hydrogen atom and an alkyl group consisting of from 1 to 10 carbon atoms,
  heterocycloalkyls consisting of from 3 to 20 atoms, optionally substituted, and
  alkyls, consisting of from 1 to 20 carbon atoms, optionally substituted;
  as well as its pharmaceutically acceptable salts, its hydrates or its polymorphic crystalline structures, its racemates, diastereoisomers or enantiomers.

2. A compound selected from the group consisting of the following compounds:

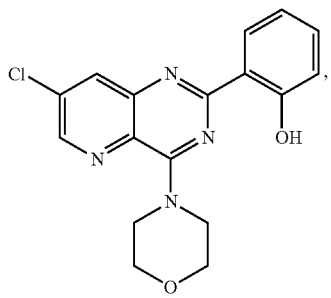

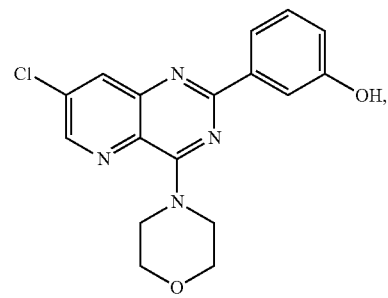

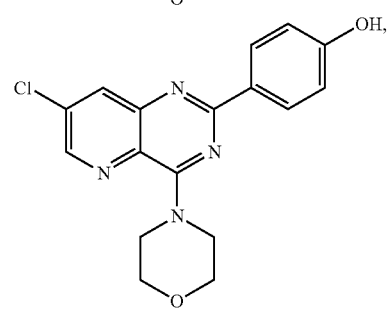

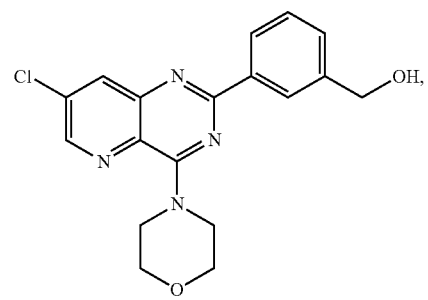

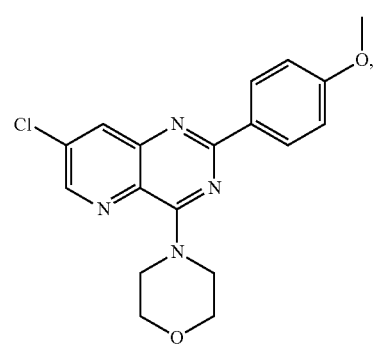

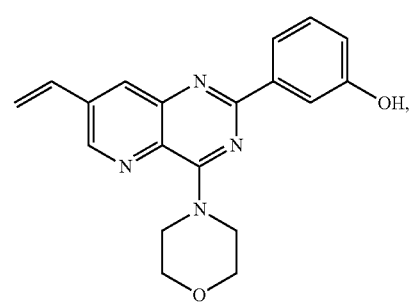

133
-continued
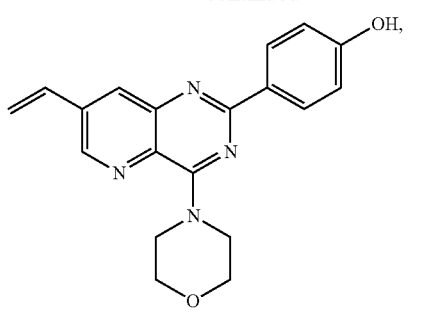
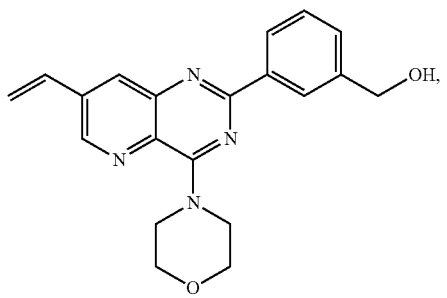
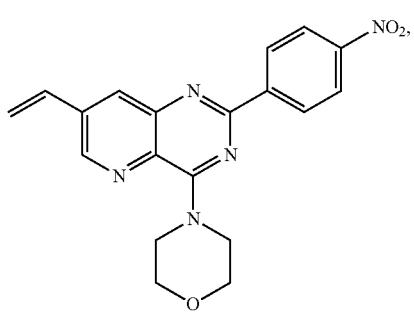
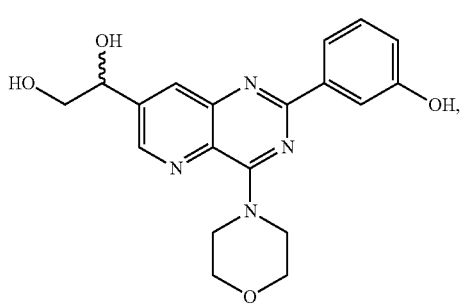
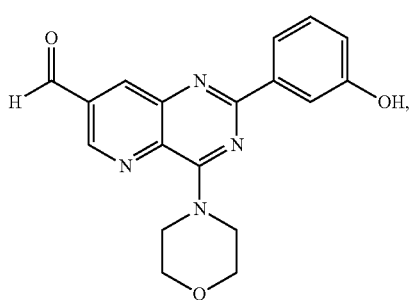
134
-continued
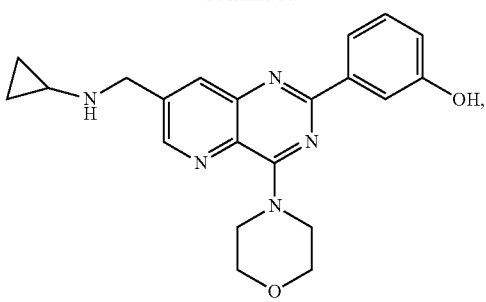
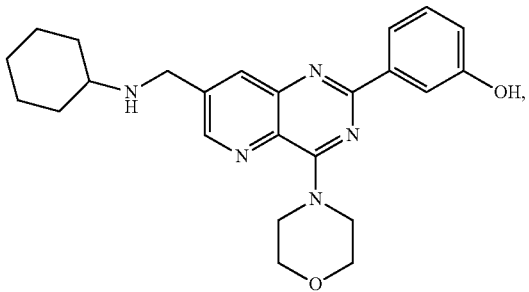
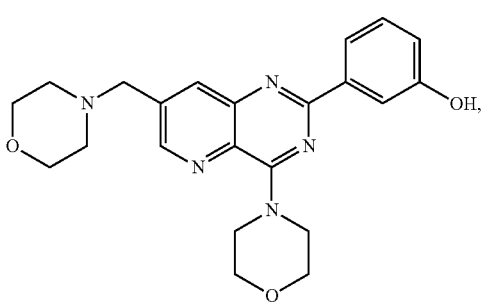
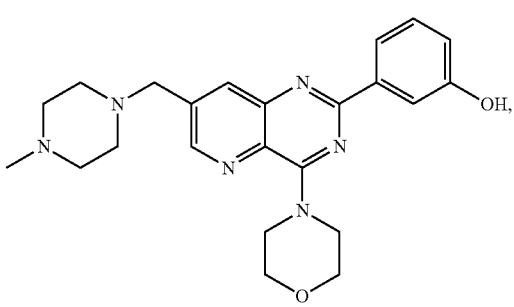
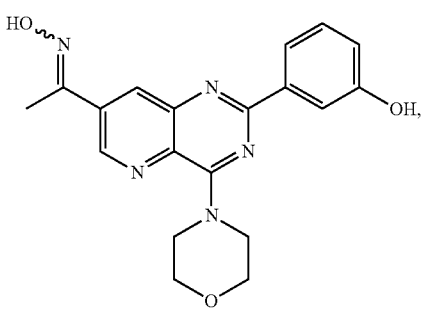

135
-continued
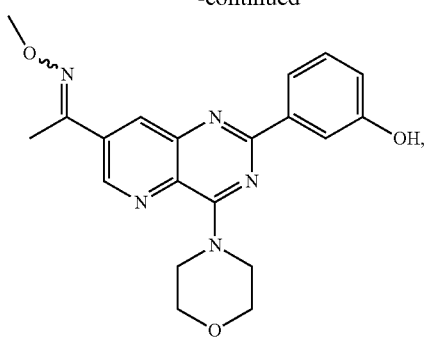
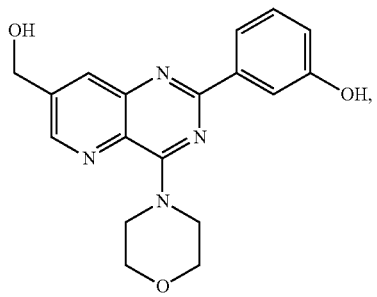
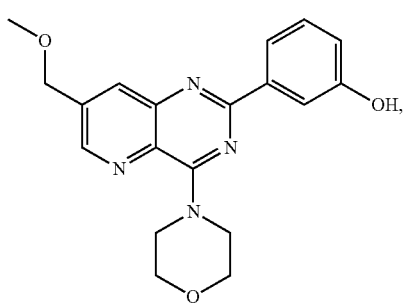
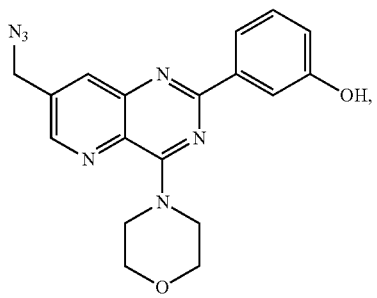
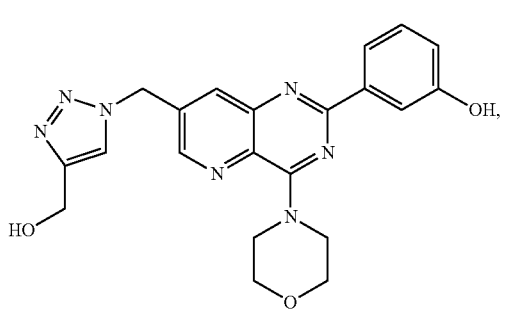
136
-continued
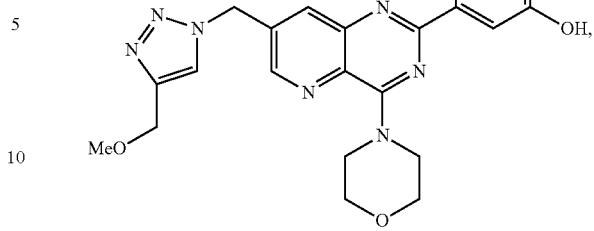
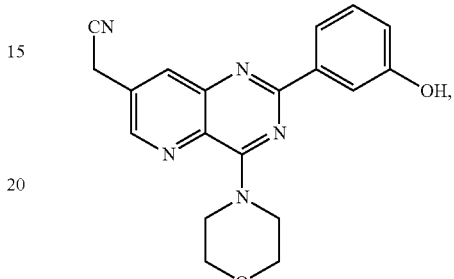
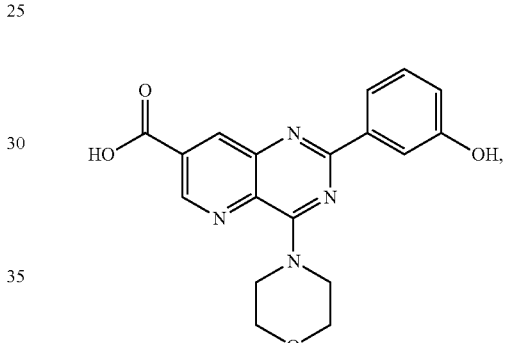
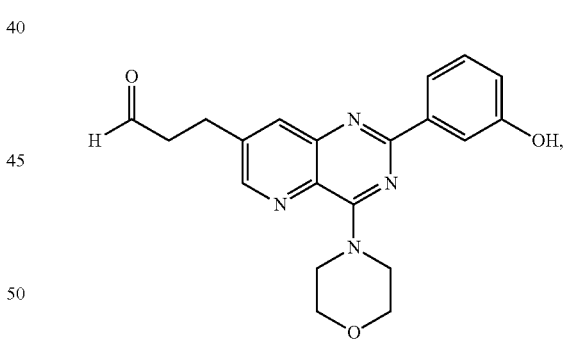
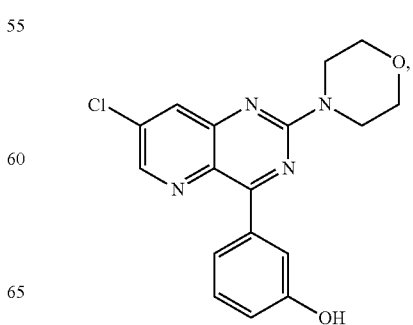

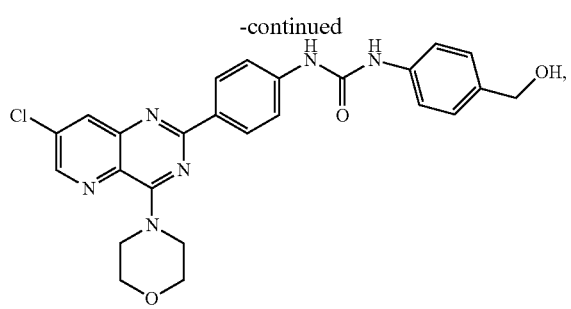
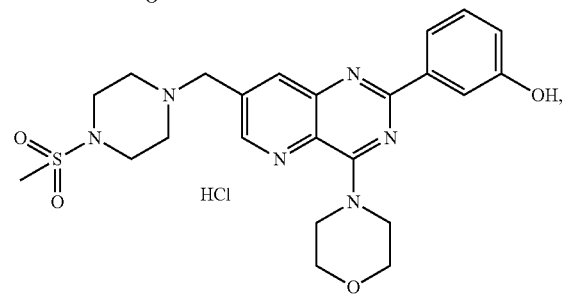
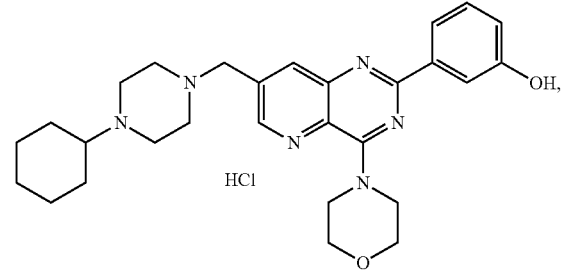
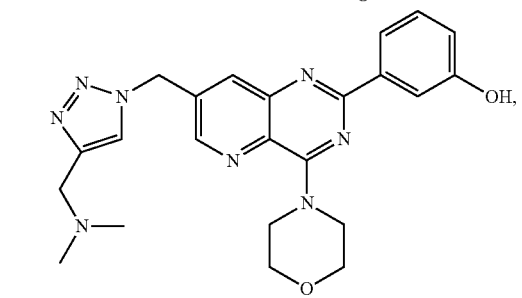
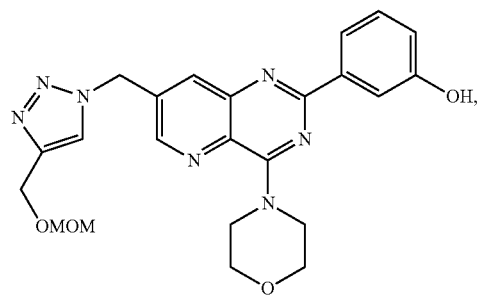
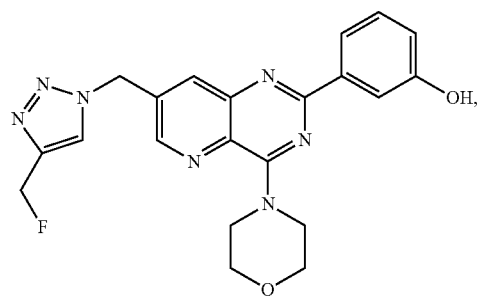

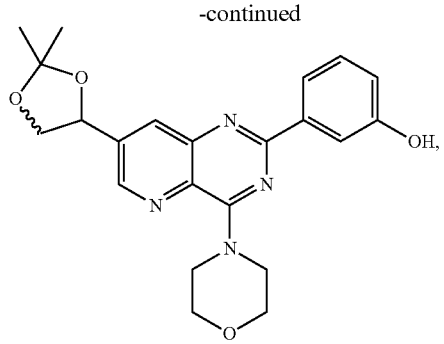
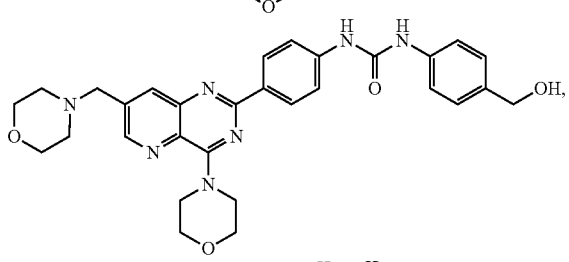
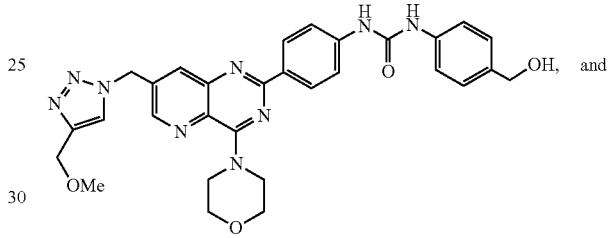
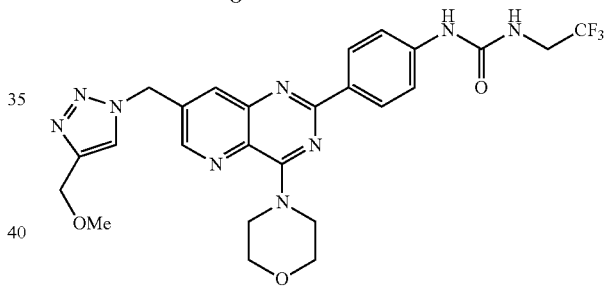

in a free or salified form.

3. A compound according to claim 2, wherein the compound is a hydrochloride form.

4. The compound of claim 1, wherein R'λ, is a phenyl group, said phenyl group being optionally substituted.

5. The compound of claim 1, wherein $R_3$ is selected from the alkyls, consisting of from 1 to 20 carbon atoms, optionally substituted.

6. The compound of claim 1, wherein $R_3$ represents an alkyl group comprising from 1 to 20 carbon atoms, said alkyl group being optionally substituted with at least one substituent selected from the (hetero)aryl groups comprising from 5 to 30 atoms, said (hetero)aryl group being optionally substituted with at least one substituent selected from the group consisting of: —CH$_2$OH, —CH$_2$OMe, —CH$_2$NMe$_2$, —CH$_2$F, and —CH$_2$OCH$_2$OMe.

7. The compound of claim 1, wherein $R_3$ represents an alkyl group comprising from 1 to 20 carbon atoms, said alkyl group being optionally substituted with at least one substituent selected from the heteroaryl groups comprising from 5 to 30 atoms, substituted with at least one substituent selected from the group consisting of: —CH$_2$OH, —CH$_2$OMe, —CH$_2$NMe$_2$, —CH$_2$F, and —CH$_2$OCH$_2$OMe.

8. The compound of claim 1, wherein $R_3$ represents an alkyl group comprising from 1 to 20 carbon atoms, said alkyl group being optionally substituted with at least one substituent selected from the isoxazoles or triazoles, substituted with at least one substituent selected from the group consisting of: —$CH_2OH$, —$CH_2OMe$, —$CH_2NMe_2$, —$CH_2F$, and —$CH_2OCH_2OMe$.

\* \* \* \* \*